(12) United States Patent
Alimi

(10) Patent No.: US 9,498,548 B2
(45) Date of Patent: Nov. 22, 2016

(54) METHOD OF USING OXIDATIVE REDUCTIVE POTENTIAL WATER SOLUTION IN DENTAL APPLICATIONS

(75) Inventor: Hojabr Alimi, Santa Rosa, CA (US)

(73) Assignee: Oculus Innovative Sciences, Inc., Petaluma, CA (US)

( * ) Notice: Subject to any disclaimer, the term of this patent is extended or adjusted under 35 U.S.C. 154(b) by 983 days.

(21) Appl. No.: 11/416,091

(22) Filed: May 2, 2006

(65) Prior Publication Data
US 2006/0253060 A1 Nov. 9, 2006

Related U.S. Application Data

(60) Provisional application No. 60/760,635, filed on Jan. 20, 2006, provisional application No. 60/760,567, filed on Jan. 20, 2006, provisional application No. 60/760,645, filed on Jan. 20, 2006, provisional application No. 60/760,557, filed on Jan. 20, 2006, provisional application No. 60/730,743, filed on Oct. 27, 2005, provisional application No. 60/676,883, filed on May 2, 2005.

(51) Int. Cl.
| | |
|---|---|
| *A61K 9/08* | (2006.01) |
| *A61K 33/00* | (2006.01) |
| *A61K 33/40* | (2006.01) |
| *A61L 2/18* | (2006.01) |
| *A61L 2/03* | (2006.01) |
| *A61K 33/20* | (2006.01) |
| *A61C 1/00* | (2006.01) |

(52) U.S. Cl.
CPC .............. *A61L 2/035* (2013.01); *A61K 33/20* (2013.01); *A61K 33/40* (2013.01); *A61L 2/183* (2013.01); *A61L 2/186* (2013.01); *A61C 1/0076* (2013.01); *A61L 2202/24* (2013.01)

(58) Field of Classification Search
CPC .... A61C 1/0076; A61K 33/20; A61K 33/40; A61L 2202/24; A61L 2/035; A61L 2/183; A61L 2/186
See application file for complete search history.

(56) References Cited

U.S. PATENT DOCUMENTS

| | | |
|---|---|---|
| 3,066,095 A | 11/1962 | Hronas |
| 3,975,246 A | 8/1976 | Eibl et al. |
| 4,048,032 A | 9/1977 | Eibl |
| 4,121,991 A | 10/1978 | Miller et al. |
| 4,236,992 A | 12/1980 | Themy |
| 4,242,446 A | 12/1980 | Madappally et al. |
| 4,296,103 A | 10/1981 | Laso |
| 4,615,937 A | 10/1986 | Bouchette |
| 4,666,621 A | 5/1987 | Clark et al. |
| 4,670,252 A | 6/1987 | Sampathkumar |
| 4,767,511 A | 8/1988 | Aragon |
| 4,781,974 A | 11/1988 | Bouchette et al. |
| 4,979,938 A | 12/1990 | Stephen et al. |
| 5,063,922 A | 11/1991 | Hakkinen |
| 5,079,010 A | 1/1992 | Natterer et al. |
| 5,084,011 A | 1/1992 | Grady |
| 5,244,768 A | 9/1993 | Inaba |
| 5,271,943 A | 12/1993 | Bogart et al. |
| 5,287,847 A | 2/1994 | Piper et al. |
| 5,312,281 A | 5/1994 | Takahashi et al. |
| 5,334,383 A | 8/1994 | Morrow |
| 5,376,242 A | 12/1994 | Hayakawa |
| 5,388,571 A | 2/1995 | Roberts et al. |
| 5,427,667 A | 6/1995 | Bakhir et al. |
| 5,445,722 A | 8/1995 | Yamaguti et al. |
| 5,474,662 A | 12/1995 | Miyamae |
| 5,507,932 A | 4/1996 | Robinson |
| 5,510,009 A | 4/1996 | Arai et al. |
| 5,543,030 A | 8/1996 | Shiramizu et al. |
| 5,560,816 A | 10/1996 | Robinson |
| 5,578,022 A | 11/1996 | Scherson et al. |
| 5,593,554 A | 1/1997 | Yamanaka et al. |
| 5,599,438 A | 2/1997 | Shiramizu et al. |
| 5,615,764 A | 4/1997 | Satoh |
| 5,616,221 A | 4/1997 | Aoki et al. |
| 5,620,587 A | 4/1997 | Nakamura |
| 5,622,725 A | 4/1997 | Kross |
| 5,622,848 A | 4/1997 | Morrow |
| 5,624,535 A | 4/1997 | Tsuchikawa et al. |
| 5,628,848 A | 5/1997 | Friese et al. |

(Continued)

FOREIGN PATENT DOCUMENTS

| | | |
|---|---|---|
| AL | WO 0076475 A1 | 12/2000 |
| CN | 1 231 994 A | 10/1999 |

(Continued)

OTHER PUBLICATIONS

International Preliminary Report on Patentability for PCT/US2006/016856, dated Nov. 6, 2007.
Annex to Form PCT/ISA/206, Communication Relating to the Results of the Partial International Search for PCT/US2006/016856 (Date of Mailing: Dec. 27, 2006).
International Search Report for PCT/US2006/016856, dated Mar. 21, 2007.
International Search Report for PCT/US2007/060854, dated Sep. 4, 2007.

(Continued)

*Primary Examiner* — Abigail Fisher
(74) *Attorney, Agent, or Firm* — Leydig, Voit & Mayer Ltd.

(57) ABSTRACT

Methods of using oxidative reduction potential (ORP) water solution that is stable for at least twenty-four hours in dental applications are provided. The ORP water solution can be administered to patients for the routine disinfection of the oral cavity as part of an on-going program of oral hygiene. The ORP water solution can further be used to irrigate and/or disinfect oral tissues and surfaces during dental procedures, oral surgery, or maxillo-facial surgery. Also, the ORP water solution can be administered to treat patients with damage to the oral tissues caused by disease or surgery.

10 Claims, 11 Drawing Sheets

(56) References Cited

U.S. PATENT DOCUMENTS

| | | | |
|---|---|---|---|
| 5,635,040 A | 6/1997 | Bakhir et al. |
| 5,635,053 A | 6/1997 | Aoki et al. |
| 5,662,625 A | 9/1997 | Westwood |
| 5,674,365 A | 10/1997 | Sano |
| 5,674,537 A | 10/1997 | Morrow |
| 5,720,869 A | 2/1998 | Yamanaka et al. |
| 5,728,274 A | 3/1998 | Kamitani et al. |
| 5,728,287 A | 3/1998 | Hough et al. |
| 5,731,008 A | 3/1998 | Morrow |
| 5,736,027 A | 4/1998 | Nakamura |
| 5,759,489 A | 6/1998 | Miura et al. |
| 5,762,779 A | 6/1998 | Shiramizu et al. |
| 5,783,052 A | 7/1998 | Bakhir et al. |
| 5,792,090 A | 8/1998 | Ladin |
| 5,798,028 A | 8/1998 | Tsuchikawa et al. |
| 5,833,831 A | 11/1998 | Kitajima et al. |
| 5,843,291 A | 12/1998 | Eki et al. |
| 5,858,201 A | 1/1999 | Otsuka et al. |
| 5,858,202 A | 1/1999 | Nakamura |
| 5,871,623 A | 2/1999 | Bakhir et al. |
| 5,888,357 A | 3/1999 | Mitsumori et al. |
| 5,897,757 A | 4/1999 | Sano |
| 5,900,257 A | 5/1999 | Breton et al. |
| 5,902,619 A | 5/1999 | Rubow et al. |
| 5,906,810 A | 5/1999 | Turner |
| 5,908,707 A | 6/1999 | Cabell et al. |
| 5,928,488 A | 7/1999 | Newman |
| 5,928,491 A | 7/1999 | Yu et al. |
| 5,932,171 A | 8/1999 | Malchesky |
| 5,938,915 A | 8/1999 | Morisawa |
| 5,938,916 A | 8/1999 | Bryson et al. |
| 5,944,978 A | 8/1999 | Okazaki |
| 5,948,220 A | 9/1999 | Kamitani et al. |
| 5,951,859 A | 9/1999 | Miura et al. |
| 5,963,435 A | 10/1999 | Biernson |
| 5,964,089 A | 10/1999 | Murphy et al. |
| 5,965,009 A | 10/1999 | Shimamune et al. |
| 5,985,110 A | 11/1999 | Bakhir et al. |
| 5,993,639 A | 11/1999 | Miyashita et al. |
| 5,997,717 A | 12/1999 | Miyashita et al. |
| 6,007,686 A | 12/1999 | Welch et al. |
| 6,007,693 A | 12/1999 | Silveri |
| 6,007,696 A | 12/1999 | Takayasu et al. |
| 6,033,539 A | 3/2000 | Gablenko |
| 6,056,866 A | 5/2000 | Maeda et al. |
| 6,059,941 A | 5/2000 | Bryson et al. |
| 6,093,292 A | 7/2000 | Akiyama |
| 6,106,691 A | 8/2000 | Nakamura et al. |
| 6,117,285 A | 9/2000 | Welch et al. |
| 6,121,317 A | 9/2000 | Wu et al. |
| 6,126,796 A | 10/2000 | Shimamune et al. |
| 6,126,810 A | 10/2000 | Fricker et al. |
| 6,139,876 A | 10/2000 | Kolta |
| 6,143,163 A | 11/2000 | Sawamoto et al. |
| 6,149,780 A | 11/2000 | Miyake |
| 6,171,551 B1 | 1/2001 | Malchesky et al. |
| 6,174,419 B1 | 1/2001 | Akiyama |
| 6,187,154 B1 | 2/2001 | Yamaguchi et al. |
| 6,200,434 B1 | 3/2001 | Shinjo et al. |
| 6,210,748 B1 | 4/2001 | Nagahara et al. |
| 6,228,251 B1 | 5/2001 | Okazaki |
| 6,231,747 B1 | 5/2001 | Fukuzuka et al. |
| 6,231,878 B1 | 5/2001 | Komatsu et al. |
| 6,251,259 B1 | 6/2001 | Satoh et al. |
| 6,258,225 B1 | 7/2001 | Yamaoka |
| 6,277,266 B1 | 8/2001 | Yamaoka |
| 6,280,594 B1 | 8/2001 | Yamaoka |
| 6,294,073 B1 | 9/2001 | Shirota et al. |
| 6,296,744 B1 | 10/2001 | Djeiranishvili et al. |
| 6,333,054 B1 | 12/2001 | Rogozinski |
| 6,340,663 B1 | 1/2002 | Deleo et al. |
| 6,342,150 B1 | 1/2002 | Sale et al. |
| 6,350,376 B1 | 2/2002 | Imaoka et al. |
| 6,358,395 B1 | 3/2002 | Schorzman et al. |
| 6,361,665 B1 | 3/2002 | Voracek |
| 6,368,592 B1 | 4/2002 | Colton et al. |
| 6,375,809 B1 | 4/2002 | Kato et al. |
| 6,384,363 B1 | 5/2002 | Hayakawa et al. |
| 6,391,169 B1 | 5/2002 | Hara et al. |
| 6,426,066 B1 | 7/2002 | Najafi et al. |
| 6,444,255 B2 | 9/2002 | Nagahara et al. |
| 6,462,250 B1 | 10/2002 | Kuriyama et al. |
| 6,464,845 B2 | 10/2002 | Shirota et al. |
| 6,475,371 B1 | 11/2002 | Shirahata et al. |
| 6,506,416 B1 | 1/2003 | Oakauchi et al. |
| 6,527,940 B1 | 3/2003 | Shimamune et al. |
| 6,544,502 B2 | 4/2003 | Heesch |
| 6,551,492 B2 | 4/2003 | Hanaoka |
| 6,565,736 B2 | 5/2003 | Park et al. |
| 6,585,867 B1 | 7/2003 | Asano |
| 6,585,868 B1 | 7/2003 | Chihara |
| 6,598,602 B1 | 7/2003 | Sjoholm |
| 6,620,315 B2 | 9/2003 | Martin |
| 6,623,615 B1 | 9/2003 | Morisawa et al. |
| 6,623,695 B2 | 9/2003 | Malchesky et al. |
| 6,624,135 B2 | 9/2003 | Takano |
| 6,632,347 B1 | 10/2003 | Buckley et al. |
| 6,638,364 B2 | 10/2003 | Harkins et al. |
| 6,638,413 B1 | 10/2003 | Weinberg et al. |
| 6,663,306 B2 | 12/2003 | Policicchio et al. |
| 6,716,335 B2 | 4/2004 | Takesako et al. |
| 6,723,226 B1 | 4/2004 | Takayasu et al. |
| 6,743,351 B1 | 6/2004 | Arai et al. |
| 6,752,757 B2 | 6/2004 | Muir et al. |
| 6,815,551 B2 | 11/2004 | Albiez et al. |
| 6,823,609 B2 | 11/2004 | Moretti |
| 6,827,849 B2 | 12/2004 | Kurokawa et al. |
| 6,833,206 B2 | 12/2004 | Erdle et al. |
| 6,833,207 B2 | 12/2004 | Joos et al. |
| 6,838,210 B2 | 1/2005 | Sawa |
| 6,843,448 B2 | 1/2005 | Parmley |
| 6,844,026 B2 | 1/2005 | Anthony et al. |
| 6,852,205 B1 | 2/2005 | Toyoshima et al. |
| 6,855,233 B2 | 2/2005 | Sawada |
| 6,855,490 B2 | 2/2005 | Sompuram et al. |
| 6,856,916 B2 | 2/2005 | Shyu |
| 6,866,756 B2 | 3/2005 | Klein |
| 6,867,048 B2 | 3/2005 | Kovacs |
| 6,874,675 B2 | 4/2005 | Kida et al. |
| 6,887,601 B2 | 5/2005 | Moulthrop et al. |
| 6,921,743 B2 | 7/2005 | Scheper et al. |
| 6,923,893 B2 | 8/2005 | Sano |
| 7,276,255 B2 | 10/2007 | Selkon |
| 8,147,444 B2 * | 4/2012 | Alimi et al. ............ 604/29 |
| 2001/0012544 A1 | 8/2001 | Nagahara et al. |
| 2001/0022273 A1 | 9/2001 | Popov et al. |
| 2002/0023847 A1 | 2/2002 | Natsume |
| 2002/0027070 A1 | 3/2002 | Oyokota et al. |
| 2002/0027079 A1 | 3/2002 | Hanaoka |
| 2002/0027084 A1 | 3/2002 | Park et al. |
| 2002/0032141 A1 | 3/2002 | Harkins |
| 2002/0036134 A1 | 3/2002 | Shirota et al. |
| 2002/0074237 A1 | 6/2002 | Takesako et al. |
| 2002/0112314 A1 | 8/2002 | Harkins |
| 2002/0134691 A1 | 9/2002 | Satoh et al. |
| 2002/0135220 A1 | 9/2002 | Yamaguchi et al. |
| 2002/0160053 A1 | 10/2002 | Yahagi et al. |
| 2002/0165220 A1 | 11/2002 | Heesch |
| 2002/0165431 A1 | 11/2002 | Muir et al. |
| 2002/0168418 A1 | 11/2002 | Lorenz et al. |
| 2002/0175085 A1 | 11/2002 | Harkins et al. |
| 2002/0176885 A1 | 11/2002 | Najafi et al. |
| 2002/0179884 A1 | 12/2002 | Hoshino et al. |
| 2002/0182262 A1 | 12/2002 | Selkon |
| 2003/0015418 A1 | 1/2003 | Tseng et al. |
| 2003/0019764 A1 | 1/2003 | Baldwin et al. |
| 2003/0024828 A1 | 2/2003 | Kondo et al. |
| 2003/0045502 A1 | 3/2003 | Kataoka et al. |
| 2003/0049163 A1 | 3/2003 | Malchesky et al. |
| 2003/0056805 A1 | 3/2003 | Sumita |
| 2003/0062068 A1 | 4/2003 | Ko et al. |
| 2003/0064427 A1 | 4/2003 | Felkner et al. |
| 2003/0087427 A1 | 5/2003 | Colton et al. |
| 2003/0089618 A1 | 5/2003 | Satoh et al. |

(56) References Cited

U.S. PATENT DOCUMENTS

| | | |
|---|---|---|
| 2003/0098283 A1 | 5/2003 | Katayose et al. |
| 2003/0141200 A1 | 7/2003 | Harada |
| 2003/0175220 A1* | 9/2003 | Wang et al. .................. 424/53 |
| 2003/0185704 A1 | 10/2003 | Bernard et al. |
| 2003/0219361 A1 | 11/2003 | Lee et al. |
| 2003/0230826 A1 | 12/2003 | Kawaguchi et al. |
| 2004/0004007 A1 | 1/2004 | Orolin et al. |
| 2004/0011665 A1 | 1/2004 | Koizumi et al. |
| 2004/0029761 A1 | 2/2004 | Wakamatsu et al. |
| 2004/0037737 A1 | 2/2004 | Marais et al. |
| 2004/0055896 A1 | 3/2004 | Anderson et al. |
| 2004/0060815 A1 | 4/2004 | Buckley et al. |
| 2004/0079791 A1 | 4/2004 | Kida et al. |
| 2004/0081705 A1 | 4/2004 | Gotou |
| 2004/0084325 A1 | 5/2004 | Weinberg et al. |
| 2004/0084326 A1 | 5/2004 | Weinberg et al. |
| 2004/0094406 A1 | 5/2004 | Sawada |
| 2004/0131695 A1 | 7/2004 | Hinze |
| 2004/0137078 A1 | 7/2004 | Najafi et al. |
| 2004/0154993 A1 | 8/2004 | Yanagihara et al. |
| 2004/0168909 A1 | 9/2004 | Larson |
| 2004/0168933 A1 | 9/2004 | Inoue |
| 2004/0171701 A1 | 9/2004 | Shaw |
| 2004/0172985 A1 | 9/2004 | Mamiya et al. |
| 2004/0177655 A1 | 9/2004 | Kodera et al. |
| 2004/0185311 A1 | 9/2004 | Muthuswamy et al. |
| 2004/0185313 A1 | 9/2004 | Halter et al. |
| 2004/0188248 A1 | 9/2004 | Sawa |
| 2004/0208940 A1 | 10/2004 | Selkon |
| 2004/0244537 A1 | 12/2004 | Runyon |
| 2004/0250323 A1 | 12/2004 | Arai et al. |
| 2004/0254744 A1 | 12/2004 | Shyu |
| 2004/0256317 A1 | 12/2004 | Yamada et al. |
| 2004/0265394 A1 | 12/2004 | Morris et al. |
| 2005/0000117 A1 | 1/2005 | Polegato |
| 2005/0054973 A1 | 3/2005 | Constantz et al. |
| 2005/0058013 A1 | 3/2005 | Warf et al. |
| 2005/0062289 A1 | 3/2005 | Cho et al. |
| 2005/0064259 A1 | 3/2005 | Coors |
| 2005/0067300 A1 | 3/2005 | Tremblay et al. |
| 2005/0074421 A1 | 4/2005 | Tanaka |
| 2005/0075257 A1 | 4/2005 | Scheper et al. |
| 2005/0101838 A1 | 5/2005 | Camillocci et al. |
| 2005/0109610 A1 | 5/2005 | Inamoto et al. |
| 2005/0121334 A1 | 6/2005 | Sumita |
| 2005/0126927 A1 | 6/2005 | Lindauer et al. |
| 2005/0126928 A1 | 6/2005 | Hung et al. |
| 2005/0129996 A1 | 6/2005 | Moulthrop et al. |
| 2005/0139465 A1 | 6/2005 | Kasuya et al. |
| 2005/0139808 A1 | 6/2005 | Alimi |
| 2005/0142157 A1 | 6/2005 | Alimi |
| 2005/0153858 A1 | 7/2005 | Anthony et al. |
| 2005/0155863 A1 | 7/2005 | Kovacs et al. |
| 2005/0161950 A1 | 7/2005 | Borden et al. |
| 2005/0178920 A1 | 8/2005 | Wilson |
| 2005/0183949 A1 | 8/2005 | Daly et al. |
| 2005/0183964 A1 | 8/2005 | Roberts et al. |
| 2005/0189234 A1 | 9/2005 | Gibson et al. |
| 2005/0189237 A1 | 9/2005 | Sano |
| 2005/0198963 A1 | 9/2005 | Wai et al. |
| 2005/0209518 A1 | 9/2005 | Sage et al. |
| 2010/0106079 A1* | 4/2010 | Alimi ............................ 604/24 |

FOREIGN PATENT DOCUMENTS

| | | |
|---|---|---|
| EP | 0 368 812 A1 | 5/1990 |
| EP | 0 601 891 A1 | 6/1994 |
| EP | 0 636 581 | 6/1994 |
| EP | 0 740 329 A | 10/1996 |
| EP | 0 889 007 A1 | 4/1997 |
| EP | 0 826 636 A1 | 3/1998 |
| EP | 0 841 305 A2 | 5/1998 |
| EP | 0 949 205 A1 | 10/1999 |
| EP | 1 038 993 A | 9/2000 |
| EP | 1 064 845 A1 | 1/2001 |
| EP | 1 065 265 A1 | 1/2001 |
| EP | 1 074 515 A2 | 2/2001 |
| EP | 1 103 264 A2 | 5/2001 |
| EP | 1 162 179 A1 | 12/2001 |
| EP | 1 293 481 A2 | 3/2003 |
| EP | 1 314 699 A1 | 5/2003 |
| EP | 1 386 887 A1 | 2/2004 |
| GB | 1 422 795 | 1/1976 |
| GB | 2253860 A | 9/1992 |
| GB | 2352728 A | 2/2001 |
| JP | 01-194993 | 8/1989 |
| JP | 01-218682 | 8/1989 |
| JP | 02-149395 | 6/1990 |
| JP | 05-339769 A | 12/1993 |
| JP | 06-182345 | 6/1994 |
| JP | 05-228474 | 9/1994 |
| JP | 05-228475 | 9/1994 |
| JP | 06-254567 | 9/1994 |
| JP | 06-312183 | 11/1994 |
| JP | 06-335685 | 12/1994 |
| JP | 07-000966 A | 1/1995 |
| JP | 07-031981 | 2/1995 |
| JP | 07-075784 A | 3/1995 |
| JP | 07-155760 | 6/1995 |
| JP | 07-214063 | 8/1995 |
| JP | 07-238640 | 12/1995 |
| JP | 07-323289 | 12/1995 |
| JP | 08-001160 A | 1/1996 |
| JP | 08-052476 | 2/1996 |
| JP | 08-061788 | 3/1996 |
| JP | 08-164192 | 6/1996 |
| JP | 08-326124 | 12/1996 |
| JP | 09-025236 | 1/1997 |
| JP | 09-157173 A2 | 1/1997 |
| JP | 09-290269 | 11/1997 |
| JP | 10-080686 | 3/1998 |
| JP | 10-113664 | 5/1998 |
| JP | 10-128331 A2 | 5/1998 |
| JP | 11-151493 A2 | 6/1999 |
| JP | 10-192860 | 3/2000 |
| JP | 2001/079548 | 3/2001 |
| JP | 2000/084559 | 4/2001 |
| JP | 2001/096275 A | 4/2001 |
| JP | 2001/113276 | 6/2001 |
| JP | 2001/191076 A2 | 7/2001 |
| JP | 03-236315 B2 | 12/2001 |
| JP | 03-247134 B2 | 1/2002 |
| JP | 2002/059164 A | 2/2002 |
| JP | 03-299250 B2 | 7/2002 |
| JP | 03-338435 B2 | 10/2002 |
| JP | 03-396853 B2 | 4/2003 |
| JP | 2003/236543 | 8/2003 |
| JP | 03-458341 B2 | 10/2003 |
| JP | 2004/049946 | 2/2004 |
| JP | 2004/216349 | 8/2004 |
| JP | 2004/223306 | 8/2004 |
| JP | 2004/223309 | 8/2004 |
| JP | 2004/223310 | 8/2004 |
| JP | 2004/232413 | 8/2004 |
| JP | 2005/013520 A2 | 1/2005 |
| JP | 2005/058848 A2 | 3/2005 |
| SU | 1296156 A | 3/1987 |
| WO | WO 95/01137 A1 | 1/1995 |
| WO | WO 96/02271 | 2/1996 |
| WO | WO 96/14835 A1 | 5/1996 |
| WO | WO 96/16555 | 6/1996 |
| WO | WO 97/40814 A1 | 11/1997 |
| WO | WO 97/49638 A | 12/1997 |
| WO | WO 9746489 A1 | 12/1997 |
| WO | WO 98/03713 A1 | 1/1998 |
| WO | WO 98/17588 A1 | 4/1998 |
| WO | WO 98/58880 A1 | 4/1998 |
| WO | WO 98/27013 | 6/1998 |
| WO | WO 98/42625 A1 | 10/1998 |
| WO | WO 99/00588 A1 | 12/1998 |
| WO | WO 99/28238 A1 | 6/1999 |
| WO | WO 0033757 A1 | 6/2000 |
| WO | WO 01/13926 | 3/2001 |
| WO | WO 01/54704 A1 | 3/2001 |

(56) References Cited

FOREIGN PATENT DOCUMENTS

| | | |
|---|---|---|
| WO | WO 01/56616 A2 | 8/2001 |
| WO | WO 01/056616 A2 | 8/2001 |
| WO | WO 02/04032 A2 | 1/2002 |
| WO | WO 03/000957 A1 | 6/2002 |
| WO | WO 03/024491 A2 | 3/2003 |
| WO | WO 03/042111 A2 | 5/2003 |
| WO | WO 03/048421 A1 | 6/2003 |
| WO | WO 03/076688 A2 | 9/2003 |
| WO | WO 03/103522 A1 | 12/2003 |
| WO | WO 2004/076721 A1 | 9/2004 |
| WO | WO 2004/078654 A2 | 9/2004 |
| WO | WO 2004/079051 A1 | 9/2004 |
| WO | WO 2004/081222 A2 | 9/2004 |
| WO | WO 2004/082690 A1 | 9/2004 |
| WO | WO 2004/092571 A1 | 10/2004 |
| WO | WO 2005/003848 A1 | 1/2005 |
| WO | WO 2005/011417 A2 | 2/2005 |
| WO | WO 2005/020896 A2 | 3/2005 |
| WO | WO 2005/030651 A1 | 4/2005 |
| WO | WO 2005/061394 A1 | 7/2005 |
| WO | WO 2005/065383 A2 | 7/2005 |
| WO | WO 2005/075581 A1 | 8/2005 |
| WO | WO 2005/080639 A1 | 9/2005 |
| WO | WO 2005/082176 A1 | 9/2005 |
| WO | WO 2006/014578 A2 | 2/2006 |
| WO | WO 2006/102680 A2 | 9/2006 |
| WO | WO 2006/102680 A3 | 9/2006 |
| WO | WO 2006/102681 A2 | 9/2006 |
| WO | WO 2006/119300 A2 | 11/2006 |

OTHER PUBLICATIONS

Written Opinion for PCT/US2007/060854, dated Sep. 4, 2007.
International Search Report for PCT/US2007/060856, dated Aug. 31, 2007.
Written Opinion for PCT/US2007/060856, dated Aug. 31, 2007.
International Search Report for PCT/US2007/060860, dated Sep. 4, 2007.
Written Opinion for PCT/US2007/060860, dated Sep. 4, 2007.
Kubota, et al., "Effectiveness of acidic oxidative potential water in peritoneal lavage for perforated appendicitis," *Asian Journal of Surgery*, Department of Surgery, University of Hong Kong, Hong Kong., 22(3), pp. 282-284 (Jul. 1999).
International Search Report for PCT/US02/38861, Mar. 20, 2003.
International Search Report in PCT/US2004/043961 (Nov. 25, 2005).
International Search Report for PCT/US2006/011251 (Sep. 14, 2006).
Written Opinion for PCT/US2006/011251 (Sep. 14, 2006).
International Search Report for PCT/US2006/011252 (Nov. 10, 2006).
Written Opinion for PCT/US2006/011252 (Nov. 10, 2006).
Office Action for U.S. Appl. 10/146,140 dated Mar. 3, 2006.
A communication from the International Searching Authority including the report of the partial international search report for PCT/US2004/043961 (Oct. 4, 2005).
Arrigo, et al., "Cytotoxic effects induced by oxidative stress in culture mammalian cells and protection provided by Hsp27 expression," (2005) (source unknown).
Ayliffe, "Working Party Report: Decontamination of minimally invasive surgical endoscopes and accessories," Journal of Hospital Infection, 45, 263-277 (2000).
Badia, et al., "Saline Wound Irrigation Reduces the Postoperative Infection Rate in Guinea Pigs." Journal of Surgical Research, 63, 457-459 (1996).
Bari, et al., "Chemical and irradiation treatments for killing *Escherichia coli* O157:H7 on alfalfa, radish, and mung bean seeds," *J Food Prot.*, 66(5), 767-74 (2003).
Bari, et al., "Effectiveness of electrolyzed acidic water in killing *Escherichia coli* O157:H7, *Salmonella enteritidis*, and *Listeria monocytogenes* on the surfaces of tomatoes," *J Food Prot.*, 66(4), 542-8 (2003).

Beckman, et al., "The free radical theory of aging matures," Physiol. Rev. 78, 547-581 (1998).
Boulton, *The Diabetic Foot*. "Diabetes: Clinical Management." Chapter 26, 293-306.
Carton, et al., "Hypotonicity induces membrane protrusions and actin remodeling via activation of small GTPases Rac and Cdc42 in Rat-1 fibroblast," *Am. J. Physiol. Cell. Physiol.*, 285, C935-C944 (2003).
Chernomorskii, "Diagram of electrochemical stability of water", *Zhurnal Fizicheskoi Khimii*, 51(4), 924-925 (1977).
Chisholm, "Wound Evaluation and Cleansing." Soft Tissue Emergencies, 10(4), 665-672 (1992).
De Grey, "Reactive oxygen species production in the mitochondrial matrix: implications for the mechanism of mitochondrial mutation accumulation," *Rejuvenation Res.*, 8(1), 13-17 (2005).
Dimri, et al., "A biomarker that identifies senescent human cell in culture and in aging skin in vivo," *Proc. Natl. Acad. Sci. USA*, 92, 9363-9667 (1995).
Dire, et al., "A Comparison of Wound Irrigation Solutions Used in the Emergency Department," Ann Emerg Med., 19(6), 704-8 (1998).
Dressler, "Standards and Histogram Interpretation in DNA Flow Cytometry," *Methods in Cell Biology*, 41, 241-262 (1994).
Dyson, et al., "Comparison of the Effects of Moist and Dry Conditions on Dermal Repair," Journal for Investigative Dermatology, 91(5), 434-439 (1988).
Erwin-Toth, et al., "Wound Care Selecting the Right Dressing," Am J Nurs., 95(2), 46-51 (1995).
Fabrizio, et al., "Comparison of electrolyzed oxidizing water with various antimicrobial interventions to reduce *Salmonella* species on poultry," *Poult. Sci.*, 81(10), 1598-605 (2002).
Field, et al., "Overview of Wound Healing in a Moist Environment," Am J Surg., 167(1A), 2S-6S (1994).
Flint, et al., "Virus cultivation, detection and genetics," Chapter 2, *Principles of Virology, Molecular Biology, Pathogenesis and Control*, ASM Press 2000; 32.
Fraise, "Choosing disinfectants," *J Hosp infect*, 43, 255-264 (1999).
Fraga, et al., "Ascorbic acid protects against endogenous oxidative DNA damage in human sperm," *Proc. Natl. Acad. Sci USA*, 88, 11003-11006 (1991).
Frippiat, et al., "Subcytotoxic $H_2O_2$ stress triggers a release of transforming growth factor-beta, which induces biomarkers of cellular senescence of human diploie fibroblast, "*J. Biol. Chem.* 276, 2531-2537 (2001).
Fomin, et al., "Participation of water [hydroxyl ions] in oxidation-reduction processes," *Sostoyanie Rol Vody Biol. Ob'ektakh, Simp., Tiflis*, 120-131 (1967).
Gao, et al., "Observation on the effect of disinfection to HBs Ag by electrolyzed oxidizing water, " Zhonghua Liu Xing Bing Xue Za Zhi, 22, 40-42 (2001).
Harada, "Behavior of hydrogen peroxide in electrolyzed anode water," *Biosci. Biotechnol Biochem.*, 66(9), 1783-91 (2002).
Hatto, et al., "The physiological property and function of the electrolyzed-ionized calcium Aquamax on water molecular clusters fractionization," *Artif. Organs*, 21(1), 439 (1997).
Hayashi, et al., "Successful treatment of mediastinitis after cardiovascular surgery using electrolyzed strong acid water aqueous solution," *Artif Organs*, 21, 39-42 (1997).
Higgins, et al., "Wound dressings and Topical Agents." *The Diabetic Foot*, 12(1), 31-40, (1995).
Hinman, et al., "Effect of Air Exposure and Occlusion on Experimental Human Skin Wounds," *Nature*, 200, 377-379 (1963).
Hollander, et al., "Laceration Management," *Annals of Emergency Medicine*, 34(3), 356-367 (1999).
Horiba, et al., "Bactericidal effect of electrolyzed neutral water on bacteria isolated from infected root canals," *Oral Surg Oral Med Oral Pathol Oral Radiol Endod*, 87, 83-87 (1999).
Horita, et al., "Healing of Fournier's gangrene of the scrotum in a haemodialysis patient after conservative therapy alone," *Nephrology Dialysis Transplantation*, 15 (3), 419-421 (2000).
Inoue, et al., "Trial of electrolyzed strong acid aqueous solution lavage in the treatment of peritonitis and intraperitoneal abscess," *Artif Organs*, 21, 28-31 (1997).

(56) References Cited

OTHER PUBLICATIONS

Ivanova, et al., "Mechanism of the extracellular antioxidant defend," *Experimental pathology and parasitology*, 4, 49-59 (2000).
Iwasawa, et al., "Bactericidal effect of acidic electrolyzed water—comparison of chemical acidic sodium hydrochloride (NaOCl) solution," *Kansenshogaku Zasshi*,; 70(9), 915-22 (1996).
Iwasawa, et al., "The influence of pH on bactericidal effects of strong acidic electrolyzed water," *Bokin Bobai*, 30(10), 635-643, (2002).
Jeter, et al., "Wound Dressings of the Nineties: Indications and Contraindications," *Wound Healing*, 8(4), 799-816 (1991).
Kaufman, "Preventing Diabetic Foot Ulcers," *Derm. Nurs.*, 6(5), 313-320 (1994).
Kiura, et al., "Bactericidal activity of electrolyzed acid water from solution containing sodium chloride at low concentration, in comparison with that at high concentration," *J Microbiol Methods*, 49(3), 285-93 (2002).
Kim, et al., "Efficacy of electrolyzed oxidizing water in inactivating *Salmonella* on alfalfa seeds and sprouts," *J Food Prot.*, 66(2), 208-14 (2003).
Kim, et al., "Roles of oxidation-reduction potential in electrolyzed oxidizing and chemically modified water for the inactivation of food-related pathogens," *J Food Prot*, 63, 19-24 (2000).
Kimbrough, et al., "Electrochemical removal of bromide and reduction of Thm formation potential in drinking water," *Water Res.*, 36(19), 4902-6 (2002).
Kitaoka, "On the electrolytic separation factor of tritium," *Radioisotopes*, 30(5), 247-52 (1981).
Koseki, et al., "Effect of nitrogen gas packaging on the quality and microbial growth of fresh-cut vegetables under low temperatures," *J Food Prot.*, 65(2), 326-32 (2002).
Koseki, et al., "Effect of mild heat pre-treatment with alkaline electrolyzed water on the efficacy of acidic electrolyzed water against *Escherichia coli* O157:H7 and *Salmonella* on lettuce," *Food Microbiology*, 21(5), 559-566 (2004).
Koseki, et al., "Decontaminative effect of frozen acidic electrolyzed water on lettuce," *J Food Prot.*, 65(2), 411-4 (2002).
Koseki, et al., "Decontamination of lettuce using acidic electrolyzed water," *J Food Prot.*, 64(5), 652-8 (2001).
Koseki, et al., "Prediction of microbial growth in fresh-cut vegetables treated with acidic electrolyzed water during storage under various temperature conditions," *J Food Prot.*, 64(12), 1935-42 (2001)..
Laing, "Diabetic Foot Ulcers," *Am J Surg*, 167, 31S-26S (1994).
Len, et al., "Ultraviolet spectrophotometric characterization and bactericidal properties of electrolyzed oxidizing water as influenced by amperage and pH," *J Food Prot*, 63, 1534-1537 (2000).
Len, et al., "Effects of storage conditions and pH on chlorine loss in electrolyzed oxidizing (EO) water," *J Agric Food Chem*, 50, 209-212 (2002).
Li, et al., "Preliminary study of microbiocide effect and its mechanism of electrolyzed oxidizing water, "Zhonghua Liu Xing Bing Xue Za Zhi, 7, 95-98 (1996).
Loshon, et al., "Analysis of the killing of spores of *Bacillus subtilis* by a new disinfectant, Sterilox," Journal of Applied Microbiology, 91, 1051-1058 (2001).
Madden, et al., "Application of Principles of Fluid Dynamics to Surgical Wound Irrigation," source unknown.
Mangram, et al., "Guideline for prevention of surgical site infection," *Infection Control and Hospital Epidemiology*, 1999, 20(4), 247-278 (1999).
Marnett, "Oxyradicals and DNA damage," Carcinogenesis, 21, 361-370 (2000).
Martinez, "Sterilant for Human Wounds is Changing Patients' Lives" Infection Control Today, (2004).
Middleton, et al., "Comparison of a solution of super-oxidized water (Sterilox) with glutaraldehyde for the disinfection of bronchoscopes, contaminated in vitro with *Mycobacterium tuberculosis* and *Mycobacterium avium-intracellulare* in sputum," *Journal of Hospital Infection*, 45, 278-282 (2000).
Minimal Access Therapy Decontamination Working Group, "Decontamination of minimally invasive surgical endoscopes and accessories," *J Hosp. Infect*, 45, 263-277 (2000).
Miranda-Altamirano et al., "Treatment of 2nd and 3rd Degree Burns in 48 Pediatric Patients Without Routine Antibiotics Routine Using New Super-oxidized Water Technology" Abstract for Meeting of the Texas Surgical Society, Apr. 1-3, 2005.
Miyamoto, et al., "Effectiveness of acidic oxidative potential water in preventing bacterial infection in islet transplantation," *Cell Transplant*, 8, 405-411 (1999).
Morita, et al., "Disinfection potential of electrolyzed solution containing sodium chloride at low concentrations," *J Virol Methods*, 85, 163-174 (2000).
Moscati, et al., "Comparison of Normal Saline with Tap Water for Wound Irrigation," American Journal of Emergency Medicine, 16(4), 379-385 (1998).
Moyer, et al., "Modulation of human fibroblast Gap junction intercellular communication by Hyaluronan," *J. Cell. Biol.* 196, 165-170 (2003).
Naderi, et al., "Oxidative stress-induced apoptosis in dividing fibroblast involves activation of p38 MAP kinase and over expression of Bax: Resistance of quiescent cells to oxidative stress," *Apoptosis*, 8, 91-100 (2003).
Nagamatsu, et al., "Application of electrolyzed acid water to sterilization of denture base part 1. Examination of sterilization effects on resin plate," *Dent. Mater J*, 20(2), 148-55, (2001).
Nagamatsu, et al., "Durability of bactericidal activity in electrolyzed neutral water by storage," *Dent Mater J*, 21, 93-104 (2002).
Nakae, et al., "Effectiveness of electrolyzed oxidized water irrigation in a burn-wound infection model," *J Trauma*, Sep.; 49(3): 511-4 (2000).
Nakagawa, et al., "Effect of rinsing hydrocolloid impressions using acidic electrolyzed water on surface roughness and surface hardness of stone models," *J Oral Sci.*, 44(34), 141-6 (2002).
Nakagawara, et al., "Spectroscopic characterization and the pH dependence of bactericidal activity of the aqueous chlorine solution," Analytical Sciences, 14(4), 691-698 (1998).
Nelson, "Newer technologies for endoscope disinfection: electrolyzed acid water and disposable-component endoscope systems," *Gasatrointest Endosc Clin N Am*, 10, 319-328 (2000).
Ogino, et al., "Treatment for abdominal aortic graft infection: irrigation with electrolyzed strong aqueous acid, in-situ grafting, and omentoplasty," *Thorac Cardiovasc Surg*, 48(1), 43-44 (2000).
Ohno, et al., "Mediastinal Irrigation with Superoxidized Water After Open-Heart Surgery: The Safety and Pitfalls of Cardiovascular Surgical Application," Surgery Today, 30, 1055-1056 (2000).
Okubo, et al., "Cytotoxicity and microbicidal activity of electrolyzed strong acid water and acidic hypochlorite solution under isotonic conditions," Kansenshogaku Zasshi, 73(10), 1025-31 (1999).
O'Neill, "Physiological significance of volume-regulatory transporters," *Am. J. Physiol.* 276, C995-C1001 (1999).
Oomori, et al., "The efficiency of disinfection of acidic electrolyzed water in the presence of organic materials," *Anal Sci*, 16, 265-369 (2000).
Ottender, et al., "Correlation of DNA adduct levels with tumor incidence: carcinogenic potency of DNA adducts," *Mutat. Res.*, 424, 237-247 (1999).
Park, et al., "Antimicrobial effect of electrolyzed water for inactivating Campylobacter jejuni during poultry washing," *International Journal of Food Microbiology*, 72(1-2), 7783 (2002).
Park, "Effectiveness of electrolyzed water as a sanitizer for treating different surfaces," J Food Prot., 65(8), 1276-80 (2002).
Park, et al., "Effects of chlorine and pH on efficacy of electrolyzed water for inactivating *Escherichia coli* O157:H7 and *Listeria monocytogenes*," *International Journal of Food Microbiology*, 91(1), 13-18 (2004).
Piaggesi, et al., "Sodium carboxyl-methyl-cellulose dressings in the management of deep ulcerations of diabetic foot," *Diabet Med.*, 18(4), 320-4 (2001).

(56) References Cited

OTHER PUBLICATIONS

Powis, et al., "Redox signaling and the control of cell growth and death," *Pharmacol Ther.*, 68, 149-173 (1995).
Rodeheaver, et al., "Identification of the Wound Infection-Potentiating Factors in Soil," American Journal of Surgery, 128(1), 8-14, (1974).
Ruddy, et al., "Decontamination in Practice: Endoscopic decontamination: an audit and practical review," Journal of Hospital Infection, 50, 261-268 (2002).
Russell, "The effect of electrolyzed oxidative water applied using electrostatic spraying on pathogenic and indicator bacteria on the surface of eggs," *Poult. Sci.*, 82(1), 158-62 (2003).
Rutala ,et al., "New Disinfection and Sterilization Methods," *Centers for Disease Control and Prevention (CDC): Emerging Infectious Diseases*, 7 (2), 348-353 (2001).
Sakai, "Development of ionic electrolyzed water and its utilities. The preparation of ionic electrolyzed water and its application to disinfection," Kurin Tekunoroji (1996), 6(3), 53-57 (1996).
Sanders, "Diabetes Mellitus: Prevention of AmPutation," *J Am Pod Med Assoc*, 84(7), 322-328 (1994).
Sawada, "Complete electrolysis using a microflow cell with an oil/water interface." *Anal Chem.*, 74(5), 1177-81 (2002).
Sekiya, et al., "Treatment of Infectious Skin Defects or Ulcers with Electrolyzed Strong Acid Aqueous Solution," *Artificial Organs*, 21 (1), 32-38 (1997).
Selkon,et al., "Evaluation of the antimicrobial activity of a new super-oxidized water, Sterilox®, for the disinfection of endoscopes," *Journal of Hospital Infection*, 41, 59-70 (1999).
Severino, et al., "Is β-galactosidase staining a marker of senescence in vitro and in vivo?" *Exp. Cell. Res.*, 257, 162-171 (2000).
Sharma, et al., "Treatment of *Escherichia coli* O157:H7 inoculated alfalfa seeds and sprouts with electrolyzed oxidizing water," *International Journal of Food Microbiology*, 86(3), 231-237 (2003).
Shen, et al., "Interactions of selenium compounds with other antioxidants in DNA damage and apoptosis in Human normal keratinocytes," *Cancer Epidemiol Biomarkders Prev.*, 10, 385-390 (2001).
Shetty, et al., "Evaluation of microbicidal activity of a new disinfectant: Sterilox® 2500 against *Clostridium difficile* spores, Helicobacter pylori, cancomycin resistant Enterococcus species, Candida albicans and several Mycobacterium species," *Journal of Hospital Infection*, 41, 101-105 (1999).
Shimmura, et al., "Acidic Electrolyzed Water in the Disinfection of the Ocular Surface," *Experimental Eye Research*, 70(1), 1-6 (2000).
Shirahata, et al., "Electrolyzed-reduced water scavenges active oxygen species and protects DNA from oxidative damage," *Biochem. Biophys. Res. Commun.*, 234(1), 26974 (1997).
Singer, et al., "Evaluation and Management of Traumatic Lacerations," *New England Journal of Medicine*, 1142-1148 (1997).
Smirnov, et al., "Electron exchangers and electron- and ion-exchangers and their use in a water treatment system," *Khim. Aktiv. Polim. Ikh Primen*, 259-262 (1969).
Solovyeva, et al., "Cleaning effectiveness of root canal irrigation with electrochemically activated anolyte and catholyte solutions: a pilot study," *International Endodontic Journal*, 33, 494-504 (2000).
Soto, et al., "Bacterial sulfate production by biodesulfurization of aromatic hydrocarbons, determined by ion chromatography," *J Chromatogr A*, 824(1), 45-52 (1998).
Stein, "SV-40-transformed human fibroblasts: evidence for cellular aging in pre-crises cells," *J Cell, Physiol*, 125, 36-44 (1985).
Stevenson, et al., "Cleansing the Traumatic Wound by High Pressure Syringe Irrigation." *JACEP*, 5(1), 17-21 (1976).
Sumita, "Characteristics and use of acidified water from redox water generator," Shokuhin Kogyo, 40(10), 29-36 (1997).
Suzuki, "Novel products generated from 2'-deoxyguanosine by hypochlorous acid or a myeloperoxidase —$H_2O_2$—Cl-system: identification of diimino-imidazole and aminoimidazolone nucleosides," *Nucleic Acids Res.*, 30, 2555-2564 (2002).
Tanaka, et al., "The use of electrolyzed solutions for the cleaning and disinfecting of dialyzers" *Artif. Organs*, 24(12), 921-8 (2000).
Tanaka, et al., "Molecular basis of antiapoptotic effect of immunophilin ligands on hydrogen peroxide-induced apoptosis in human glioma cells," *Neurochem Res.*, 29(8), 1529-36 (2004).
Tanaka, et al., "Antimicrobial activity of superoxidized water" *Journal of Hospital Infection*, 34, 43-49 (1996).
Takeshita, et al., "Influence of free residual chlorine concentration and pH on bactericidal effects of electrolyzed water," Bokin Bobai, 29(2), 69-72 (2001).
Takeyoshi, et al., "Primary eye irritation and 5-day cumulative skin irriation studies of super oxidized water in rabbits," Oyo Yakuri, 48(3), 173-177 (1994).
Tateno, et al., "MT-4 plaque formation can distinguish cytopathic subtypes of the human immunodeficiency virus (HIV)," *Virology*, 167, 299-301 (1988).
Upright, et al., "Evaluation of Mesalt dressings and continuous wet saline dressings in ulcerating metastatic skin lesions," *Cancer Nursing*, 17(2), 149-155 (1994).
Valko, et al., "Role of oxygen radicals in DNA damage and cancer incidence," *Mol Cell Biochem*, 266, 37-56 (2004).
Van Britsom, et al., "A rapid method for the detection of uranium in surface water," *Sci. Total Environ.*, 173-174, 83-9 (1995).
Venkitanarayanan, et al., "Efficacy of Electrolyzed Oxidizing Water for Inactivating *Escherichia coli* O157:H7, *Salmonella enteritidis*, and *Listeria monocytogenes*," *Applied and Environmental Microbiology*, 65 (9), 4276-4279 (1999).
Veves, et al., "A randomized, controlled trial of Promogran (a collagen/oxidized regenerated cellulose dressing) vs standard treatment in the management of diabetic foot ulcers," *Arch Surg.*, 137(7), 822-7 (2002).
Winter, "Formation of the Scab and the Rate of Epithelization of Superficial Wounds in the Skin of the Young Domestic Pig," *Nature*, 193, 293-294 (1962).
Xakellis, et al., "Hydrocolloid versus saline-gauze dressings in treating pressure ulcers: a cost-effectiveness analysis," *Arch Phys Med Rehabil.*, 73(5), 463-9 (1992).
Yahagi, et al.,"'Effect of Electrolyzed Water on Wound Healing," *Artificial Organs*, 24 (12), 984-987 (2000).
Yang, et al., "The effect of pH on inactivation of pathogenic bacteria on fresh-cut lettuce by dipping treatment with electrolyzed water," *Journal of Food Science*, 68(3), 1013-1017 (2003).
Yoshimoto, et al., "Virucidal effect of super oxidized water" Kagaku Ryoho no Ryoiki, 12(7), 1337-1342 (1996).
Young, et al., "Mechanisms of killing of *Bacillus subtilis* spores by hypochlorite and chlorine dioxide," *J Appl Microbiol*, 95, 54-67 (2003).
Zinkevich, et al., "The effect of super-oxidized water on *Escherichia coli*," *Journal of Hospital Infection*, 46, 153-156 (2000).
Zhang, et al., "Antioxidant superoxide dismutase attenuates increased endothelial permeability induced by platelet activating factor," *Soc Gynecol Investig*. 10, 5-10 (2003).
Sakashita et al., "Antimicrobial effects and efficacy on habitually hand-washing of strong acidic electrolyzed water—a comparative study of alcoholic antiseptics and soap and tap water", Kansenshogaku Zasshi 76, 373-377 (2002).
Supplementary European Search Report for EP 02 79 0029 Aug. 4, 2005.
Carlson, "Redox media as a factor in destroying germs," *Schriftenreihe des Vereins fuer Wasser-, Boden- and Lufthygiene*, 31, 21-39 (1970).
Gutierrez et al., "Produccion de agents biologicos par alas terapias genicas y celulares en humanos," *Diagnostico molecular en medicina*, 265-291 (2003).
Michida et al., "Biomimetic oxidation of diphenyl sulfide with electrochemical P-450 model system in CH2Cl2 treated with alkaline solution," Yakugaku Zasshi, 119(10), 780-5 (1999).
Nakae et al., "Effectiveness of electrolyzed oxidized water irrigation in a burn-wound infection," *J Trauma Injury, Infection, and Critical Care*, 49, 511-514 (2000).
European Search Report for EP 1 103 264.
European Search Report for EP 1 293 481.

\* cited by examiner

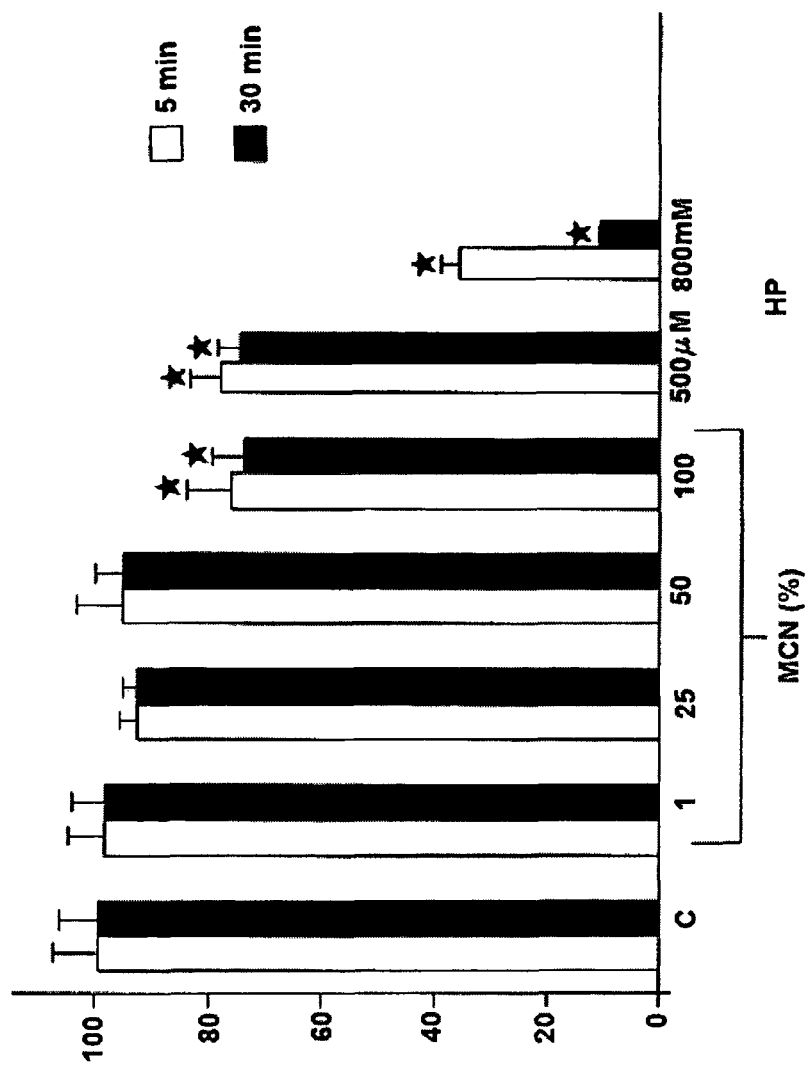

FIG. 6A
MCN
HP
40X

ORP Water Solution-Treated

METHOD OF USING OXIDATIVE REDUCTIVE POTENTIAL WATER SOLUTION IN DENTAL APPLICATIONS

CROSS-REFERENCE TO RELATED APPLICATIONS

This patent application claims the benefit of U.S. Provisional Patent Application Nos. 60/760,635 filed Jan. 20, 2006; 60/760,567 filed Jan. 20, 2006; 60/760,645 filed Jan. 20, 2006; 60/760,557 filed Jan. 20, 2006; 60/730,743 filed Oct. 27, 2005; and 60/676,883 filed May 2, 2005; each of which is hereby incorporated herein in their entirety by reference.

FIELD OF THE INVENTION

This invention pertains to a method of treating periodontal disease and other dental conditions by administration of oxidative reductive potential water solutions.

BACKGROUND OF THE INVENTION

Periodontal (gum) diseases, including gingivitis and periodontitis, are serious infections that, left untreated, can lead to tooth loss. Periodontal disease can affect one tooth or many teeth. Periodontal disease begins when the bacteria in "plaque," a sticky, colorless film that constantly forms on teeth, causes the gums to become inflamed. In the mildest form of the disease, gingivitis, the gums redden, swell and bleed easily. Gingivitis is often caused by inadequate oral hygiene. Gingivitis is reversible with professional treatment and good oral home care.

Untreated gingivitis can advance to periodontitis. With time, plaque can spread and grow below the gum line. Toxins produced by the bacteria in plaque irritate the gums. Gums can then separate from the teeth, forming spaces between the teeth and gums that become infected. As the disease progresses, gum tissue and bone are destroyed. Eventually, teeth can become loose and may have to be removed by periodontal surgery.

The main cause of periodontal disease is bacterial plaque. However, factors such as genetics, pregnancy, puberty, poor nutrition, stress, smoking, diabetes and other systemic diseases, and medications can contribute to periodontal disease. Antibiotics are often used in combination with mechanical plaque removal (scaling) in the treatment of more advanced periodontal disease. Nevertheless periodontal disease remains the cause of significant morbidity and expense to society. Accordingly, there is a need for additional novel effective treatments for periodontal disease.

In particular, root canal infection, an infectious disease of bacterial etiology, is an important cause of tooth loss in the world. Current therapeutic modalities include scaling and root plaining of the surfaces of the teeth to eliminate bacterial plaque and calculus, and the use of antiseptic solutions to combat the infectious process caused by a wide spectrum of oral micro-organisms. These antiseptics, however, have high toxicity and consequently cannot be used for prolonged periods. In addition, some of the commonly used antiseptics have adverse side effects such as distortion of taste and staining of teeth.

Oxidative reductive potential (ORP) water, also known as super-oxidized water, can be used as a non-toxic disinfectant to eradicate microorganisms, including bacteria, viruses and spores, in variety of settings. For example, ORP water may be applied in the healthcare and medical device fields to disinfect surfaces and medical equipment. Advantageously, ORP water is environmentally safe and, thus, avoids the need for costly disposal procedures. ORP water also has application in wound care, medical device sterilization, food sterilization, hospitals, consumer households and anti-bioterrorism.

Although ORP water is an effective disinfectant, it has an extremely limited shelf-life, usually only a few hours. As a result of this short lifespan, the production of ORP water must take place in close proximity to where ORP water is to be used as a disinfectant. This means that a healthcare facility, such as a hospital, must purchase, house and maintain the equipment necessary to produce ORP water. Additionally, prior manufacturing techniques have not been able to produce sufficient commercial-scale quantities of ORP water to permit its widespread use as a disinfectant at healthcare facilities.

Accordingly, a need exists for an ORP water that is stable over an extended period of time and methods of using such an ORP water. A need also exists for cost-effective methods of preparing commercial-scale quantities of ORP water. The present invention provides such an ORP water and methods of preparing and using such an ORP water.

ORP water has also been used as a tissue cell growth promoter in patients as described in U.S. Patent Application Publication 2002/0160053 A1. However, the application of water that quickly loses contact with tissue does not maximize the effectiveness of the treatment. Accordingly, a need exists for compositions containing ORP water that remain in contact with the tissue being treated and that are stable over an extended period of time. These and other advantages of the invention, as well as additional inventive features, will be apparent from the description of the invention provided herein.

BRIEF SUMMARY OF THE INVENTION

The present invention provides a method of treating periodontal disease in a patient by administering an oxidative reductive potential (ORP) water solution, wherein the solution is stable for at least twenty-four hours. The invention also is directed to a method of treating periodontal disease in a patient by administering an oxidative reductive potential water solution, wherein the solution comprises anode water and cathode water. In one embodiment, the ORP water solution used in the method of the invention comprises hydrogen peroxide and one or more chlorine species.

The present invention additionally provides a method of treating damaged oral tissue, which method comprises contacting the impaired or damaged tissue with a therapeutically effective amount of an ORP water solution, wherein the solution is stable for at least twenty-four hours. The method includes treating tissue, which has been impaired or damaged by oral surgery or which has been impaired or damaged by causes that are not necessarily related to surgery, e.g., burns, cuts, abrasions, scrapes, rashes, ulcers, puncture wounds, infections, and the like.

The present invention also relates to a method of using an ORP water solution as an irrigant in an oral or maxillo-facial dental procedure by administering an ORP water solution to a patient in an amount sufficient to irrigate the site.

The present invention further provides a method of disinfecting a surface, which method comprises contacting the surface with an anti-infective amount of an ORP water solution, wherein the solution is stable for at least twenty-four hours. The surface can be biological, inanimate, or a combination of such surfaces can be disinfected in accordance with the present invention. Biological surfaces include, e.g., muscle tissue, bone tissue, organ tissue, mucosal tissue, and combinations thereof, can be disinfected in accordance with the present invention. Inanimate surfaces include, e.g., surgically implantable devices, prosthetic devices, and medical devices.

Another aspect of the present invention includes a formulation for topical administration comprising an oxidative reductive potential water solution and a thickening agent, wherein the formulation is stable for at least twenty-four hours.

The invention also pertains to a pharmaceutical dosage form comprising (1) a formulation for topical administration comprising an oxidative reductive potential water solution and a thickening agent and (2) a sealed container, wherein the formulation is stable for at least twenty-four hours.

Additionally, the invention is directed to a method for treating a condition in a patient comprising topically administering to a patient a therapeutically effective amount of a formulation comprising an oxidative reductive potential solution and a thickening agent, wherein the formulation is stable for at least about twenty-four hours.

The invention further provides a method for promoting wound healing in a patient comprising applying to a wound a formulation comprising an oxidative reductive potential water solution and a thickening agent, wherein the formulation is administered in an amount sufficient to promote wound healing, and wherein the formulation is stable for at least about twenty-four hours.

The invention additionally provides a method for preventing a condition in a patient comprising topically administering to a patient a therapeutically effective amount of a formulation comprising an oxidative reductive potential water solution and a thickening agent, wherein the formulation is stable for at least about twenty-four hours.

BRIEF DESCRIPTION OF THE DRAWINGS

FIG. 4A-4C depicts a graphical comparison of cell viability, apoptosis and necrosis in human dermal fibroblasts (HDFs) treated with an exemplary ORP water solution (MCN) versus hydrogen peroxide (HP).

FIG. 6A-6B illustrate the expression of a senescence associated with β-galactosidase in HDFs after chronic exposure to low concentrations of an exemplary ORP water solution (MCN) versus hydrogen peroxide (HP).

DETAILED DESCRIPTION OF THE INVENTION

Figure 1:
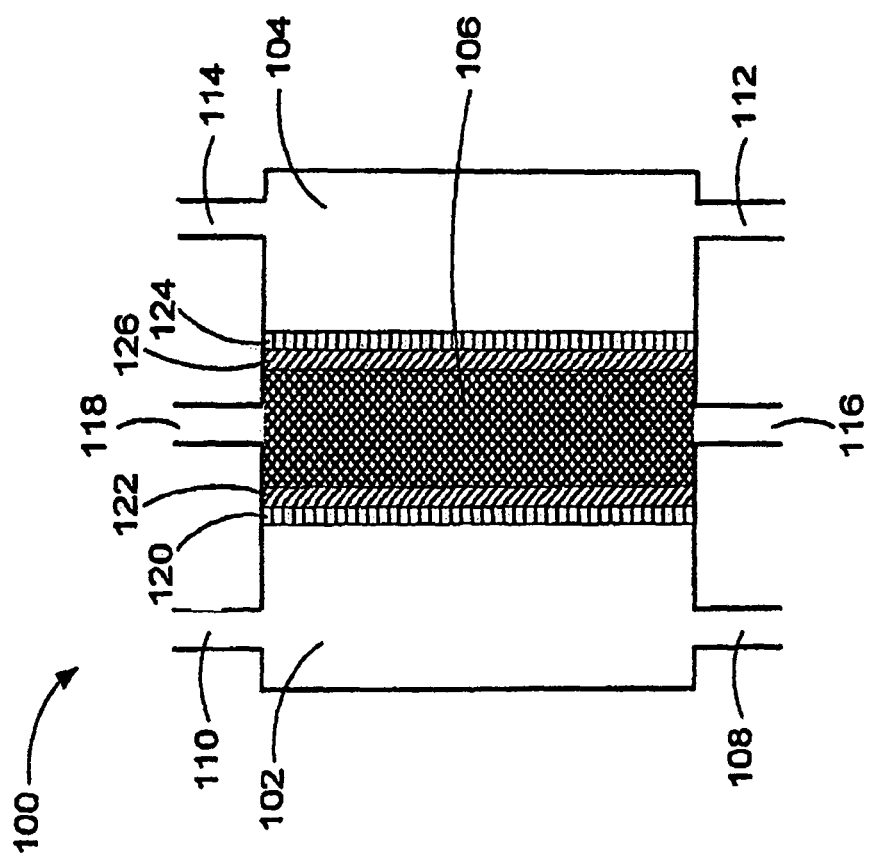
FIG. 1 is a schematic diagram of a three-chambered electrolysis cell for producing an oxidative reductive potential water solution of the present invention.

The present invention provides a method of preventing or treating a condition in a patient, which method comprises administering to the patient a therapeutically effective amount of an oxidative reductive potential (ORP) water solution, wherein the solution is stable for at least twenty-four hours. The condition can include, e.g., medical conditions, illnesses, injuries, allergies, and the like, which are treatable with the ORP water solution of the present invention.

The therapeutically effective amount administered to the patient, e.g., an animal, particularly a human, in the context of the present invention should be sufficient to effect a therapeutic or prophylactic response in the patient over a reasonable time frame. The dose can be readily determined using methods that are well known in the art. One skilled in the art will recognize that the specific dosage level for any particular patient will depend upon a variety of factors. For example, the dose can be determined based on the strength of the particular ORP water solution employed, the severity of the condition, the body weight of the patient, the age of the patient, the physical and mental condition of the patient, general health, sex, diet, and the like. The size of the dose also can be determined based on the existence, nature, and extent of any adverse side effects that might accompany the administration of a particular ORP water solution. It is desirable, whenever possible, to keep adverse side effects to a minimum.

Factors, which can be taken into account for a specific dosage can include, for example, bioavailability, metabolic profile, time of administration, route of administration, rate of excretion, pharmacodynamics associated with a particular ORP water solution in a particular patient, and the like. Other factors can include, e.g., the potency or effectiveness of the ORP water solution with respect to the particular condition to be treated, the severity of the symptoms presented prior to or during the course of therapy, and the like. In some instances, what constitutes a therapeutically effective amount also can be determined, in part, by the use of one or more of the assays, e.g., bioassays, which are reasonably clinically predictive of the efficacy of a particular ORP water solution for the treatment or prevention of a particular condition.

The ORP water solution of the present invention can be administered therapeutically, alone or in combination with one or more other therapeutic agents, to a patient, e.g., a human, e.g., to treat an existing condition. The ORP water solution of the present invention also can be administered prophylactically, alone or in combination with one or more other therapeutic agents, to a patient, e.g., a human, that has been exposed to one or more causative agents associated with the condition. For example, the ORP water solution of the invention can be suitably administered to a patient that has been exposed to one or more infection-causing microorganisms (e.g., viruses, bacteria and/or fungi) prophylactically to inhibit or decrease the likelihood of infection in a patient, or decrease the severity of an infection that develops as a result of such exposure.

One skilled in the art will appreciate that suitable methods of administering the ORP water solution of the present invention are available, and, although more than one route of administration can be used, a particular route can provide a more immediate and more effective reaction than another route. The therapeutically effective amount can be the dose necessary to achieve an "effective level" of the ORP water solution in an individual patient. The therapeutically effective amount can be defined, for example, as the amount required to be administered to an individual patient to achieve a blood level, tissue level, and/or intracellular level of the ORP water of the present invention to prevent or treat the condition in the patient.

When the effective level is used as a preferred endpoint for dosing, the actual dose and schedule can vary depending, for example, upon interindividual differences in pharmacokinetics, distribution, metabolism, and the like. The effective level also can vary when the ORP water solution of the present invention is used in combination with one or more therapeutic agents other than the ORP water solution of the present invention, e.g., one or more anti-infective agents, one or more "moderating," "modulating" or "neutralizing agents," e.g., as described in U.S. Pat. Nos. 5,334,383 and 5,622,848, one or more anti-inflammatory agents, and the like.

An appropriate indicator can be used for determining and/or monitoring the effective level. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, by direct or indirect observations such as, e.g., the concentration of urinary metabolites, changes in markers associated with the condition (e.g., viral count in the case of a viral infection), decrease in the symptoms associated with the conditions, and the like.

The ORP water of the present invention can be administered using any suitable method of administration known in the art. The ORP water of the present invention can be administered in combination with one or more pharmaceutically acceptable carriers, vehicles, adjuvants, excipients, or diluents, which are known in the art. One skilled in the art can easily determine the appropriate formulation and method of administration for administering the ORP water in accordance with the present invention. Any necessary adjustments in dose can be readily made by a skilled practitioner to address the nature or severity of the condition being treated in view of other factors, such as, e.g., side effects, changes in the patient's overall condition, and the like.

In one embodiment, the condition is an upper respiratory condition, which is treatable by the ORP water solution of the present invention. Any suitable method of administration can be employed for the treatment or prevention of an upper respiratory condition in accordance with the present invention. Preferably, the ORP solution is administered to the upper airway, e.g., so as to contact one or more upper airway tissues associated with the upper respiratory condition. The ORP solution of the present invention can be administered to the upper airway as a steam or a spray. In addition, the ORP water solution of the present invention can be administered by aerosolization, nebulization or atomization. When the ORP water solution of the invention is administered by aerosolization, nebulization or atomization, it is preferably administered in the form of droplets having a diameter in the range of from about 1 micron to about 10 microns.

Methods and devices, which are useful for aerosolization, nebulization and atomization, are well known in the art. Medical nebulizers, for example, have been used to deliver a metered dose of a physiologically active liquid into an inspiration gas stream for inhalation by a recipient. See, e.g., U.S. Pat. No. 6,598,602. Medical nebulizers can operate to generate liquid droplets, which form an aerosol with the inspiration gas. In other circumstances medical nebulizers may be used to inject water droplets into an inspiration gas stream to provide gas with a suitable moisture content to a recipient, which is particularly useful where the inspiration gas stream is provided by a mechanical breathing aid such as a respirator, ventilator or anaesthetic delivery system.

An exemplary nebulizer is described, for example, in WO 95/01137, which describes a hand held device that operates to eject droplets of a medical liquid into a passing air stream (inspiration gas stream), which is generated by a recipient's inhalation through a mouthpiece. Another example can be found in U.S. Pat. No. 5,388,571, which describes a positive-pressure ventilator system which provides control and augmentation of breathing for a patient with respiratory insufficiency and which includes a nebulizer for delivering particles of liquid medication into the airways and alveoli of the lungs of a patient. U.S. Pat. No. 5,312,281 describes an ultrasonic wave nebulizer, which atomizes water or liquid at low temperature and reportedly can adjust the size of mist. In addition, U.S. Pat. No. 5,287,847 describes a pneumatic nebulizing apparatus with scalable flow rates and output volumes for delivering a medicinal aerosol to neonates, children and adults. Further, U.S. Pat. No. 5,063,922 describes an ultrasonic atomizer.

The method of the present invention can be used for preventing or treating an upper respiratory condition, which affects one or more upper respiratory airway tissues, particularly nasal tissue, sinus tissue, and lung tissue. Such upper respiratory conditions can include, for example, a sinusitis (e.g., a rhinosinusitis, an acute sinusitis, a chronic sinusitis, and the like), a pharyngitis, an asthma, and the like, which are preventable or treatable with the ORP solution of the present invention.

Chronic sinusitis typically refers to inflammation of the sinuses that continues for at least 3 weeks, but often continues for months or even years. Allergies are frequently associated with chronic sinusitis. In addition, patients with asthma have a particularly high frequency of chronic sinusitis. Inhalation of airborne allergens (substances that provoke an allergic reaction), such as dust, mold, and pollen, often set off allergic reactions (allergic rhinitis) that, in turn, may contribute to sinusitis. People who are allergic to fungi can develop a condition called "allergic fungal sinusitis." Damp weather or pollutants in the air and in buildings also can affect people subject to chronic sinusitis.

Like acute sinusitis, chronic sinusitis is more common in patients with immune deficiency or abnormalities of mucus secretion or movement (e.g., immune deficiency, HIV infection, cystic fibrosis, Kartagener's syndrome). In addition, some patients have severe asthma, nasal polyps, and severe asthmatic responses to aspirin and aspirin-like medications (so-called non-steroidal anti-inflammatory drugs, or NSAIDs). These latter patients have a high frequency of chronic sinusitis.

A doctor can diagnose sinusitis by medical history, physical examination, X-rays, and if necessary, MRIs or CT scans (magnetic resonance imaging and computed tomography). After diagnosing sinusitis and identifying a possible cause, a doctor can prescribe a course of treatment that will reduce the inflammation and relieve the symptoms. Treating acute sinusitis typically requires re-establishing drainage of the nasal passages, controlling or eliminating the source of the inflammation, and relieving the pain. Doctors generally recommend decongestants to reduce the congestion, antibiotics to control a bacterial infection, if present, and pain relievers to reduce the pain.

When treatment with drugs fails, surgery may be the only alternative for treating chronic sinusitis, e.g., removal of adenoids, removal of nasal polyps, repair of a deviated septum, endoscopic sinus surgery, and the like. It is believed that the administration of ORP water in accordance with the method of the present invention can be used for treating chronic sinusitis as an alternative to potentially avoid more aggressive therapies, such as antibiotics and surgery.

With regard to pharyngitis, it is estimated that worldwide, 1 to 2% of all visits to doctors' offices, clinics and emergency rooms are because of pharyngitis. In the United States and Mexico, pharyngitis/tonsillitis accounts for a reported 15 and 12 million consultations per year, respectively. It has been established that these cases are caused by various bacteria and viruses. On the one hand we know that pharyngitis and tonsillitis caused by group A β-hemolytic *Streptococcus* significantly raise the risk of rheumatic fever in poor populations. On the other hand, it is believed that only 5 to 15% of pharyngitis cases are caused by this bacterium, and that the rest of the acute cases are due to bacteria and viruses of little epidemiological relevance. The latter cases tend to be self-limiting in a few days and do not leave sequelae.

It has been verified that a great number of doctors worldwide prescribe antibiotics indiscriminately for acute pharyngitis. This occurs in a daily practice, often because patients tend to request powerful antibiotics. Unfortunately, it is difficult to establish an accurate diagnosis of streptococcal pharyngitis/tonsillitis clinically and the cost/benefit ratio of treating acute pharyngitis/tonsillitis with antibiotics is questionable. In some countries, such as Mexico, the waste of government resources to cover the cost of antibiotics, in addition to working days missed, represent a significant loss with respect to the national budget.

It is believed that the administration of ORP water in accordance with the method of the present invention can be useful for the adjuvant treatment of acute pharyngitis/tonsillitis. The empirical treatment of acute pharyngitis/tonsillitis may begin with administering an ORP water solution in accordance with the present invention, and, depending on evolution or the result of the rapid test for *Streptococcus*, antibiotics may be initiated from 48-72 hours thereafter only if needed. The method of the present invention may thus alow the use of antibiotics to be deferred, and, at the same time, reduce the symptomatology of the patient and accelerate the patient's recovery if the pharyngitis/tonsillitis is not from group A *Streptococcus*. The adjuvant use of an ORP water solution of the present invention with antibiotics for the treatment of streptococcal pharyngitis/tonsillitis also may shorten the period of clinical response and decrease the incidence of recurrences.

The method of the present invention also can be used for the prevention or treatment of an infection, which is treatable with the ORP water solution of the present invention. The infection can be caused by one or more infectious pathogens such as, for example, infectious microorganisms. Such microorganisms can include, for example, viruses, bacteria, and fungi. The viruses can include, e.g., one or more viruses selected from the group consisting of adenoviruses, HIV, rhinoviruses, and flu viruses. The bacteria can include, e.g., one or more bacteria selected from the group consisting of *Escherichia coli, Pseudomonas aeruginosa, Staphylococcus aureus*, and *Mycobaterium tuberculosis*. The fungi can include, e.g., one or more fungi selected from the group consisting of *Candida albicans, Bacillus subtilis* and *Bacillus athrophaeus*. The method of the present invention also can be used for the prevention or treatment of inflammatory conditions or allergic reactions, which are treatable with the ORP water solution of the invention.

In addition, organisms that can be controlled, reduced, killed or eradicated by treatment with the ORP water solution used in accordance with the invention include, e.g., *Pseudomonas aeruginosa, Escherichia coli, Enterococcus hirae, Acinetobacter baumannii, Acinetobacter* species, *Bacteroides fragilis, Enterobacter aerogenes, Enterococcus faecalis*, Vancomycin resistant-*Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, Streptococcus pyogenes, Salmonella choleraesuis, Shigella dysenteriae*, and other susceptible bacteria, as well as yeasts, e.g., *Trichophyton mentagrophytes, Candida albicans* and *Candida tropicalis*. The ORP water solution can also be used in accordance with the invention to control, reduce, kill or eradicate viruses including, e.g., adenovirus, human immunodeficiency virus (HIV), rhinovirus, influenza (e.g., influenza A), hepatitis (e.g., hepatitis A), coronavirus (responsible for, e.g., Severe Acute Respiratory Syndrome (SARS)), rotavirus, avian flu virus, respiratory syncytial virus, herpes simplex virus, varicella zoster virus, rubella virus, and other susceptible viruses.

In another embodiment, the method of the present invention comprises parenterally administering the ORP water solution of the invention. Parenteral administration can include administering the ORP water solution of the invention intravenously, subcutaneously, intramuscularly, or intraperitoneally. In a preferred embodiment, the ORP water solution of the present invention is administered intravenously to prevent or treat a condition in accordance with the method of the present invention. Suitable conditions can include, e.g., viral myocarditis, multiple sclerosis, and AIDS. See, e.g., U.S. Pat. Nos. 5,334,383 and 5,622,848, which describe methods of treating viral myocarditis, multiple sclerosis, and AIDS via intravenous administration of ORP water solutions.

The present invention additionally provides a method of treating impaired or damaged tissue, which method comprises contacting the impaired or damaged tissue with a therapeutically effective amount of the ORP water solution of the present invention. Any suitable method can be used for contacting the impaired or damaged tissue, so as to treat the impaired or damaged tissue in accordance with the present invention. For example, the impaired or damaged tissue can be treated in accordance with the invention by irrigating the tissue with the ORP water solution of the invention, so as to contact the impaired or damaged tissue with the ORP water. Alternatively (and additionally), the ORP water solution of the present invention can be administered as a steam or a spray, or by aerosolization, nebulization or atomization, as described herein, so as to contact the impaired or damaged tissue with the ORP water.

The method of the present invention can be used in the treatment of tissues, which have been impaired or damaged, e.g., by surgery. For instance, the method of the present invention can be used for treating tissues, which have been impaired or damaged by an incision. In addition, the method of the present invention can be used for treating tissues, which have been impaired or damaged by oral surgery, graft surgery, implant surgery, transplant surgery, cauterization, amputation, radiation, chemotherapy, and combinations thereof. The oral surgery can include, for example, dental surgery such as, e.g., root canal surgery, tooth extraction, gum surgery, and the like.

The method of the present invention also includes treating tissues, which have been impaired or damaged by one or more burns, cuts, abrasions, scrapes, rashes, ulcers, puncture wounds, combinations thereof, and the like, which are not necessarily caused by surgery. The method of the present invention also can be used for treating impaired or damaged tissue, which is infected, or tissue impaired or damaged due to infection. Such infection can be caused by one or more infectious pathogens, such as, e.g., one or more microorganisms selected from the group consisting of viruses, bacteria, and fungi, as described herein.

The present invention further provides a method of disinfecting a surface, which method comprises contacting the surface with an anti-infective amount of the ORP water solution of the present invention. In accordance with the method of the present invention, the surface can be contacted using any suitable method. For example, the surface can be contacted by irrigating the surface with the ORP water solution of the invention, so as to disinfect the surface in accordance with the invention, for example during a root canal procedure. Additionally, the surface can be contacted by applying the ORP water solution of the present invention to the surface as a steam or a spray, or by aerosolization, nebulization or atomization, as described herein, so as to disinfect the surface in accordance with the invention. Further, the ORP water solution of the present invention can be applied to the surface with a cleaning wipe, as described herein. By disinfecting a surface in accordance with the present invention, the surface may be cleansed of infectious microorganisms. Alternatively (or additionally), the ORP water solution of the present invention can be applied to the surface to provide a barrier to infection, thereby disinfecting a surface in accordance with the present invention.

The method of the present invention can be used for disinfecting a surface, which is biological, inanimate, or a combination thereof. Biological surfaces can include, for example, tissues within one or more body cavities such as, for example, the oral cavity, the sinus cavity, the cranial cavity, the abdominal cavity, and the thoracic cavity. Tissues within the oral cavity include, e.g., mouth tissue, gum tissue, tongue tissue, and throat tissue. The biological tissue also can include muscle tissue, bone tissue, organ tissue, mucosal tissue, and combinations thereof. Inanimate surfaces include, for example, surgically implantable devices, prosthetic devices, and medical devices. In accordance with the method of the present invention, the surfaces of internal organs, viscera, muscle, and the like, which may be exposed during surgery, can be disinfected, e.g., to maintain sterility of the surgical environment.

The present invention also provides formulations for topical administration comprising an oxidative reductive potential (ORP) water solution and a thickening agent which are prepared to provide enhanced efficacy and stability.

The amount of water present the formulations of the invention is generally from about 10% by weight to about 95% by weight, based on the weight of the formulation. Preferably, the amount of water present is from about 50% by weight to about 90% by weight.

The formulations of the invention preferably include an ORP water solution comprising anode water and cathode water. Anode water is produced in the anode chamber of the electrolysis cell used in the present invention. Cathode water is produced in the cathode chamber of the electrolysis cell.

The formulation for topical administration according to the present invention further comprises a thickening agent. Any suitable thickening agent may be used to produce a formulation having the desired viscosity which is generally greater than the ORP water solution alone. The thickening agent utilized is compatible with the ORP water solution and other optional components in the formulation. Suitable thickening agents include, but are not limited to, polymers and hydroxyethylcellulose. Suitable polymers may be homopolymers or copolymers and are optionally crosslinked. Other suitable thickening agents are generally known in art (see, e.g., *Handbook of Cosmetic and Personal Care Additives,* 2nd ed., Ashe et al. eds. (2002), and *Handbook of Pharmaceutical Excipients,* 4th ed., Rowe et al. eds. (2003)).

Preferred thickening agents are acrylic acid-based polymers. More preferably, the thickening agents are high molecular weight, crosslinked, acrylic acid-based polymers. These polymers have the following general structure:

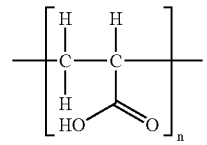

Such polymers are sold under the tradename Carbopol® by Noveon. Carbopol® polymers are generally supplied as rheology modifiers for use thickeners, suspending agents, and stabilizers in a variety of personal care products, pharmaceuticals, and household cleaners. Carbopol® polymers may be used in either solid (e.g., powder) or liquid form.

The acrylic acid-based polymers suitable for use in the invention may be homopolymers or copolymers. Suitable homopolymers may be crosslinked, preferably with allyl sucrose or allylpentaerythritol. Suitable copolymers of acrylic acid are modified by long chain ($C_{10}$-$C_{30}$) alkyl acrylates and may be crosslinked, preferably with allylpentaerythritol.

Carbopol® polymers are neutralized in order to achieve maximum viscosity. As supplied, Carbopol® polymers are dry, tightly coiled acidic molecules, held in a coiled structure by hydrogen bonds. Once dispersed in water, or another solvent, they begin to hydrate and partially uncoil. The most common way to achieve maximum thickening from Carbopol® polymers is by converting the acidic polymer into a salt. This is easily achieved by neutralizing with a common base such as sodium hydroxide (NaOH) or triethanolamine (TEA). This neutralization "uncoils" the long chain polymer, swelling the molecule into an effective thickening form.

Suitable thickening agents will yield the desired viscosity for the formulation, as well as other characteristics, such as appearance, shear resistance, ion resistance, and thermal stability. For example, Carbopol® 934 is preferred for a formulation that is either a suspension or emulsion (rather than a clear gel) with a viscosity greater than 3000 centipoise (cps). Carbopol® 974P may alternatively be used for its advantageous bioadhesive properties.

Any suitable amount of a thickening agent is present in the formulation of the invention to yield the desired viscosity for the formulation. Generally, the amount of thickening agent is from about 0.1% by weight to about 50% by weight, based on the weight of the formulation. Preferably, the amount of thickening agent is from about 0.1% to about 10% by weight.

In other terms, the amount of thickening agent based on the volume of the ORP water solution is generally from about 0.1% weight/volume (mg/mL) to about 50% weight/volume (mg/mL). Preferably, the amount of thickening agent is from about 0.1% w/v to about 10% w/v.

The amount of thickening agent generally is from about 0.1 g/250 mL to about 50 mg/250 mL of the ORP water solution. Preferably, the amount of thickening agent present is from about 1 mg/250 mL to about 20 mg/250 mL of the ORP water solution and, most preferably, from about 3 mg/250 mL to about 15 mg/250 mL.

When acrylic acid-based polymers are used at low concentrations, the formulation flows easily with a slippery feel. At higher concentrations, the formulation of the invention has a high viscosity and is pseudoplastic and resistant to flow. When shear force is applied by a mixer or pump, the apparent viscosity is reduced, and the formulation may be pumped.

The formulation of the invention may optionally include a neutralizing agent. Any suitable neutralizing agent may be used to yield the desired pH of the formulation. Suitable neutralizing agents include, for example, sodium hydroxide, triethanolamine, ammonia, potassium hydroxide, L-arginine, AMP-95, Neutrol TE, Tris Amino, Ethomeen, di-isopropanolamine, and tri-isopropanolamine. Other neutralizing agents are generally known in the art (see, e.g., *Handbook of Cosmetic and Personal Care Additives*, 2nd ed., Ashe et al. eds. (2002), and *Handbook of Pharmaceutical Excipients*, 4th ed., Rowe et al. eds. (2003)). Suitable neutralizing agents may be either in liquid or solid form.

Preferably, the neutralizer triethanolamine used when the thickening agent is an acrylic acid-based polymer such as Carbopol®. The neutralizing agent converts the formulation into a gel.

Any suitable amount of neutralizing agent may be included in the formulation of the invention. Generally, the amount of neutralizing agent is from about 0.1% by weight to about 50% by weight, based on the weight of the formulation. Preferably, the amount of neutralizing agent is from about 0.1% to about 10% by weight, based on the weight of the formulation. On a volume basis, the amount of neutralizing agent is present in an amount of about 1% to about 50% by volume, based on the volume of the ORP water solution.

When added in liquid form, the neutralizing may be added in an amount of from about 1 mL/250 mL to about 100 mL/250 mL of the ORP water solution. Preferably, the amount of neutralizing agent is from about 10 mL/250 mL to about 90 mg/250 mL of the ORP water solution.

The formulation may further contain additional components such as colorants, fragrances, buffers, physiologically acceptable carriers and/or excipients, and the like. Examples of suitable colorants include, but are not limited to, titanium dioxide, iron oxides, carbazole violet, chromium-cobalt-aluminum oxide, 4-Bis[(2-hydroxyethyl)amino]-9,10-anthracenedione bis(2-propenoic)ester copolymers, and the like. Any suitable fragrance can be used.

The formulation of the invention may be prepared by any suitable means. The components of the formulation, such as the ORP water solution and thickening agent, may be mixed together in any manner to yield a homogenous mixture. Preferably, the components are mixed together for several minutes using an electric mixture or other suitable device to ensure uniformity. The components of the formulation are generally mixed from about 400 rpm to about 1000 rpm, preferably from about 500 rpm to about 800 rpm, and more preferably from about 500 rpm to about 600 rpm.

The formulation is mixed for a sufficient period of time to yield a homogenous mixture, generally from about 1 minute to about 10 minutes after all of the components have been combined.

When the thickening agent is in the form of a power, it may first be sieved to break up large agglomerates to allow for the preparation of a homogenous formulation.

A neutralizing agent, such as triethanolamine, may subsequently be added to the formulation containing the ORP water solution and thickening agent. As noted above, the addition of triethanolamine may allow the thickening agent, such as Carbopol®, to uncoil and, thus, yield a formulation having the desired viscosity.

A colorant or fragrance may also be added to the mixture either before or after the thickening agent, such as Carbopol®, is dissolved into the ORP water, but before the neutralization step.

The physical properties of the formulation of the invention are typically the same as those of the ORP water solution present in the formulation. The properties of the ORP water solution remain even after the addition of a thickening agent and optional neutralizing agent. For example, the stability and pH of the ORP water solution itself and the formulation containing the ORP water solution are generally the same. Accordingly, all of the characteristics of the ORP water solution described herein apply to the formulation of the invention.

For example, the formulation of the invention is generally stable for at least twenty-hours, and typically at least two days. More typically, the formulation is stable for at least one week (e.g., one week, two weeks, three weeks, four weeks, etc.), and preferably at least two months. More preferably, the formulation is stable for at least six months after its preparation. Even more preferably, the formulation is stable for at least one year, and most preferably for at least three years.

The pH of the formulation is generally from about 6 to about 8. Preferably, the pH of the formulation is from about 6.2 to about 7.8, more preferably from about 7.2 to about 7.5, and most preferably from about 7.4 to about 7.6.

The formulation of the invention may be used any form suitable for topical administration to a patient. A suitable form includes, but is not limited to, gel, lotion, cream, paste, ointment, and the like, which forms are known in the art (see, e.g., *Modern Pharmaceutics*, 3rd ed., Banker et al. ed. (1996)). Gels are typically a semisolid emulsion or suspension that has a three-dimensional structure. Preferably, the formulation is in the form of a gel.

Pastes are generally semisolid suspensions that often contain a large portion of solids (e.g., 20% to 50%) dispersed in an aqueous or fatty vehicle. Lotions are typically liquid emulsions containing a water-based vehicle and volatiles (more than 50%) and that have a sufficiently low viscosity (less than 30,000 cps) to be poured. Ointments and creams are generally semisolid emulsions or suspensions that may contain hydrocarbons or polyethylene glycols as part of the carrier along with other volatile components.

When the formulation of the invention is in the form of a gel, the viscosity of the gel is in the range of from about 10,000 to about 100,000 centipoise (cps) (e.g., about 15,000 cps, about 20,000 cps, about 25,000 cps, about 30,000 cps, about 35,000 cps, about 40,000 cps, about 45,000 cps, about 50,000 cps, about 55,000 cps, about 60,000 cps, about 65,000 cps, about 70,000 cps, about 75,000 cps, about 80,000 cps, about 85,000 cps, about 90,000 cps, about 95,000 cps, or ranges thereof) when measured at room temperature (about 25° C.).

The pH of the gel is typically in the range of from about 6.0 to about 8.0. Above this pH, the viscosity of the thickening agent, such as the Carbopol® polymer, may decrease leading to an unsatisfactory topical formulation. Preferably, the pH of the gel is from about 6.4 to about 7.8, more preferably from about 7.2 to about 7.5, and more preferably, from about 7.4 to about 7.6.

The formulation of the invention is suitable for topical administration to a patient, including a human and/or animal, to treat a variety of conditions. Specifically, the formulation may be applied to animals (e.g., mice, rats, pigs, cows, horses, dogs, cats, rabbits, guinea pigs, hamsters, birds) and humans. Topical administration includes application to the skin as well as oral, intranasal, intrabronchial, and rectal routes of administration.

In another embodiment, the invention is directed to a method for treating a condition in a patient by topically administering a formulation comprising an ORP water solution and a thickening agent.

Conditions in a patient that may be treated according to the invention include, for example, the following: surgical/open wound cleansing agent; skin pathogen disinfection (e.g., for bacteria, mycoplasmas, virus, fungi, prions); wound disinfection (e.g., battle wounds); wound healing promotion; burn healing promotion; treatment of skin fungi; psoriasis; athlete's foot; ear infections (e.g., swimmer's ear); traumatic wounds; acute, subchronic and chronic infections (e.g. diabetic foot infections being an example of the latter), pressure ulcers, derma-abrasion, debrided wounds, laser re-surfacing, donor sites/grafts, exuding partial and full thickness wounds, superficial injuries (lacerations, cuts, abrasions, minor skin irritations) and other medical applications on or in the human or animal body. Ulcers treated according to the invention may or may not have abscesses or necrotic tissue present.

Additionally, the invention is directed to a method for promoting wound healing in a patient by applying to a wound a formulation comprising an oxidative reductive potential water solution and a thickening agent. The wound to be treated may be caused by any surgery, ulcer or other means. Ulcers that may be treated include, for example, diabetic foot ulcers.

The invention further relates to a method for preventing a condition in a patient by topically administering a formulation comprising an ORP water solution and a thickening agent. For example, the formulation (e.g., in the form of a gel) can be used as a barrier on open wounds to prevent infection. Specifically, the formulation (e.g., in the form of a gel) can be applied to the surface of a wound, such as a foot ulceration in a diabetic, who is prone to neurological and vascular complications. The formulation applied thusly can provide a barrier to infection, since these wounds are the principal portal for infection for diabetic patients.

The formulation may be used to prevent sexually transmitted diseases in a patient including, for example, infections. Such infections that may be prevented include herpes, human immunodeficiency virus (HIV) and vaginal infections. When the formulation is in the form of a gel, it may be used as a spermicide.

The formulation of the invention may be used or applied in a therapeutically effective amount to provide the desired therapeutic effect on bacteria, viruses, and/or germs. As used herein, a therapeutically effective amount refers to an amount of the formulation that results in an improvement of the condition being treated or to be prevented. For example, when used to treat an infection, a therapeutically effective amount of the formulation reduces the extent of the infection and/or prevents further infection. As is appreciated by one skilled in the art, the efficacy of the formulation of the invention resulting from administering the formulation may be short-term (i.e., a few days) and/or long-term (e.g., months).

The formulation may further be applied over a sufficient period of time, for example, about one, about two, several days, one week, or several weeks, until the desired effect on the patient is observed.

The formulation may be applied in any suitable manner. For example, a quantity of the formulation may be applied to the surface of the patient to be treated and then evenly spread using the patient's own fingers. Alternatively, a health care provider may apply the formulation to the patient's tissue. A suitable implement, for example, a disposable wipe or cloth, may be used to apply the formulation.

The ORP water of the present invention is produced by an oxidation-reduction process, which can be referred to as an electrolytic or redox reaction, in which electrical energy is used to produce chemical change in an aqueous solution. Electrical energy is introduced into and transported through water by the conduction of electrical charge from one point to another in the form of an electrical current. In order for the electrical current to arise and subsist there must be charge carriers in the water, and there must be a force that makes the carriers move. The charge carriers can be electrons, as in the case of metal and semiconductors, or they can be positive and negative ions in the case of solutions.

A reduction reaction occurs at the cathode while an oxidation reaction occurs at the anode in the process for preparing an ORP water solution according to the invention. The specific reductive and oxidative reactions that occur are described in International Application WO 03/048421 A1.

As used herein, water produced at an anode is referred to as anode water and water produced at a cathode is referred to as cathode water. Anode water contains oxidized species produced from the electrolytic reaction while cathode water contains reduced species from the reaction.

Anode water generally has a low pH typically of from about 1 to about 6.8. Anode water generally contains chlorine in various forms including, for example, chlorine gas, chloride ions, hydrochloric acid and/or hypochlorous acid. Oxygen in various forms is optionally present including, for example, oxygen gas, peroxides, and/or ozone. Cathode water generally has a high pH typically of from about 7.2 to about 11. Cathode water generally contains hydrogen gas, hydroxyl radicals, and/or sodium ions.

The ORP water solution of the invention may be acidic, neutral or basic, and generally has a pH of from about 1 to about 14. At this pH, the ORP water solution can safely be applied in suitable quantities to hard surfaces without damaging the surfaces or harming objects, such as human skin, that comes into contact with the ORP water solution. Typically, the pH of the ORP water solution is from about 3 to about 8. More preferably, the pH of the ORP water solution is from about 6.4 to about 7.8, even more preferably from about 7.2 to about 7.5, and most preferably, the pH is from about 7.4 to about 7.6.

The ORP water solution of the present invention generally has an oxidation-reduction potential of from about −1000 millivolts (mV) to about +1350 millivolts (mV). This potential is a measure of the tendency (i.e., the potential) of a solution to either accept or transfer electrons that is sensed by a metal electrode and compared with a reference electrode in the same solution. This potential may be measured by standard techniques including, for example, by measuring the electrical potential in millivolts of the ORP water solution relative to standard reference silver/silver chloride electrode. The ORP water generally has a potential from about −400 mV to +1150 mV. Preferably, the ORP water solution has a potential from about 0 mV to about +1250 mV, and more preferably from about +500 mV to about +1250 mV. Even more preferably, the ORP water of the present invention has a potential from about +800 mV to about +1100 mV, even more preferably from about +800 mV to about +1000 mV, and most preferably from about +850 mV to about +1000 mV.

Various ionic and other species may be present in the ORP water solution of the invention. For example, the ORP water solution may contain chlorine (e.g., free chlorine and bound chlorine), and optionally, ozone and peroxides (e.g., hydrogen peroxide). The presence of one or more of these species is believed to contribute to the disinfectant ability of the ORP water solution to kill a variety of microorganisms, such as bacteria and fungi, as well as viruses.

Free chlorine typically includes, but is not limited to, hypochlorous acid (HClO), hypochlorite ions (ClO$^-$), sodium hypochlorite (NaOCl), chloride ion (Cl$^-$), chlorite ions (ClO$_2^-$), dissolved chlorine gas (Cl$_2$), and other radical chlorine species. The ratio of hypochlorous acid to hypochlorite ion is dependent upon pH. At a pH of 7.4, hypochlorous acid levels are from about 25 ppm to about 75 ppm. Temperature also impacts the ratio of the free chlorine component.

Bound chlorine is chlorine in chemical combination with ammonia or organic amines (e.g., chloramines). Bound chlorine is generally present in an amount up to about 20 ppm.

Chlorine, and, optionally ozone and hydrogen peroxide may present in the ORP water solution of the invention in any suitable amount. The levels of these components may be measured by methods known in the art.

Typically, the total chlorine content, which includes both free chlorine and bound chlorine, is from about 50 parts per million (ppm) to about 200 ppm. Preferably, the total chlorine content is about 80 ppm to about 150 ppm.

The chlorine content may be measured by methods known in the art, such as the DPD colorimeter method (Lamotte Company, Chestertown, Md.) or other known methods established by the Environmental Protection Agency. In the DPD colorimeter method, a yellow color is formed by the reaction of free chlorine with N,N-diethyl-p-phenylenediamine (DPD) and the intensity is measured with a calibrated calorimeter that provides the output in parts per million. Further addition of potassium iodide turns the solution a pink color to provide the total chlorine value. The amount of bound chlorine present is then determined by subtracting free chlorine from the total chlorine.

Typically, chlorine dioxide is present in an amount of from about 0.01 ppm to about 5 ppm, preferably from about 1.0 ppm to about 3.0 ppm, and more preferably from about 1.0 ppm to about 1.5 ppm.

Ozone is optionally present in an amount of from about 0.03 ppm to about 0.2 ppm, and preferably from about 0.10 ppm to about 0.16 ppm. Hydrogen peroxide levels in the ORP water solution are optionally in the range of about 0.01 ppm to about 200 ppm, and preferably between about 0.05 ppm and about 100 ppm. More preferably, hydrogen peroxide is present in an amount between about 0.1 ppm and about 40 ppm, and most preferably between about 1 ppm and 4 ppm. Peroxides (e.g., $H_2O_2$, $H_2O_2^-$ and $HO_2^-$) are generally present in a concentration of less than 0.12 milliMolar (mM).

The total amount of oxidizing chemical species present in the ORP water solution is in the range of about 2 millimolar (mM) which includes the aforementioned chlorine species, oxygen species, and additional species that may be difficult to measure such as Cl$^-$, ClO$_3$, Cl$_2^-$, and ClO$_x$. The level of oxidizing chemical species present may also be measured by ESR spectroscopy (using Tempone H as the spin trap molecule).

The ORP water solution of the invention is generally stable for at least about twenty-four hours, and typically at least about two days. More typically, the water solution is stable for at least about one week (e.g., about one week, about two weeks, about three weeks, about four weeks, etc.), and preferably at least about two months. More preferably, the ORP water solution is stable for at least about six months after its preparation. Even more preferably, the ORP water solution is stable for at least about one year, and most preferably for at least about three years.

As used herein, the term stable generally refers to the ability of the ORP water solution remain suitable for its intended use, for example, in decontamination, disinfection, sterilization, anti-microbial cleansing, and wound cleansing, for a specified period of time after its preparation under normal storage conditions (i.e., room temperature).

The ORP water solution of the invention is also stable when stored under accelerated conditions, typically about 30° C. to about 60° C., for at least about 90 days, and preferably about 180 days.

The concentrations of ionic and other species present solution are generally maintained during the shelf-life of the ORP water solution. Typically, the concentrations of free chlorine, and, optionally, ozone and hydrogen peroxides are maintained at about 70% or great from their initial concentration for at least about two months after preparation of the ORP water solution. Preferably, these concentrations are maintained at about 80% or greater of their initial concentration for at least about two months after preparation of the ORP water solution. More preferably, these concentrations are at about 90% or greater of their initial concentration for at least about two months after preparation of the ORP water solution, and most preferably, about 95% or greater.

The stability of the ORP water solution of the invention may be determined based on the reduction in the amount of organisms present in a sample following exposure to the ORP water solution. The measurement of the reduction of organism concentration may be carried out using any suitable organism including bacteria, fungi, yeasts, or viruses. Suitable organisms include, but are not limited to, *Escherichia coli, Staphylococcus aureus, Candida albicans*, and *Bacillus athrophaeus* (formerly *B. subtilis*). The ORP water solution is useful as both a low-level disinfectant capable of an about four log ($10^4$) reduction in the concentration of live microorganisms and a high-level disinfectant capable of an about six log ($10^6$) reduction in concentration of live microorganisms.

In one aspect of the invention, the ORP water solution is capable of yielding at least an about four log ($10^4$) reduction in total organism concentration following exposure for one minute, when measured at least two months after preparation of the solution. Preferably, the ORP water solution is capable of such a reduction of organism concentration when measured at least about six months after preparation of the solution. More preferably, the ORP water solution is capable of such a reduction of organism concentration when measured at least about one year after preparation of the ORP water solution, and most preferably when measured at least three years after preparation of the ORP water solution.

In another aspect of the invention, the ORP water solution is capable of at least an about six log ($10^6$) reduction in the concentration of a sample of live microorganisms selected from the group consisting of *Escherichia coli, Pseudomonas aeruginosa, Staphylococcus aureus* and *Candida albicans* within one minute of exposure, when measured at least two months after preparation of the ORP water solution. Preferably, the ORP water solution is capable of achieving this reduction of *Escherichia coli, Pseudomonas aeruginosa, Staphylococcus aureus* or *Candida albicans* organisms when measured at least about six months after preparation, and more preferably at least about one year after preparation. Preferably, the ORP water solution is capable of at least an about seven log ($10^7$) reduction in the concentration of such live microorganism within about one minute of exposure, when measured at least about two months after preparation.

The ORP water solution of the invention is generally capable of reducing a sample of live microorganisms including, but not limited to, *Escherichia coli, Pseudomonas aeruginosa, Staphylococcus aureus* and *Candida albicans*, from an initial concentration of from about $1\times10^6$ to about $1\times10^8$ organisms/ml to a final concentration of about zero organisms/ml within about one minute of exposure, when measured at least about two months after preparation of the ORP water solution. This is from an about six log ($10^6$) to an about eight log ($10^8$) reduction in organism concentration. Preferably, the ORP water solution is capable of achieving this reduction of *Escherichia coli, Pseudomonas aeruginosa, Staphylococcus aureus* or *Candida albicans* organisms when measured at least about six months after preparation, and more preferably at about least one year after preparation.

Alternatively, the ORP water solution is capable of an about six log ($10^6$) reduction in the concentration of a spore suspension of *Bacillus athrophaeus* spores within about five minutes of exposure, when measured at least about two months after preparation of the ORP water solution. Preferably, the ORP water solution is capable of achieving this reduction in the concentration of *Bacillus athrophaeus* spores when measured at least about six months after preparation, and more preferably at least about one year after preparation.

The ORP water solution is further capable of an about four log ($10^4$) reduction in the concentration of a spore suspension of *Bacillus athrophaeus* spores within about thirty (30) seconds of exposure, when measured at least about two months after preparation of the ORP water solution. Preferably, the ORP water solution is capable of achieving this reduction in the concentration of *Bacillus athrophaeus* spores when measured at least six months after preparation, and more preferably at least one year after preparation.

The ORP water solution is also capable of an about six log ($10^6$) reduction in the concentration of fungal spores, such as *Aspergillis niger* spores, within about five to about ten minutes of exposure, when measured at least two months after preparation of the ORP water solution. Preferably, the ORP water solution is capable of achieving this reduction in the concentration of fungal spores when measured at least about six months after preparation, and more preferably at about least one year after preparation.

In one embodiment, the ORP water solution of the invention optionally comprises hydrogen peroxide ($H_2O_2$) and one or more chlorine species. Preferably, the chlorine species present is a free chlorine species. The free chlorine species may be selected from the group consisting of hypochlorous acid (HOCl), hypochlorite ions ($OCl^-$), sodium hypochlorite (NaOCl), chlorite ions ($ClO_2^-$), chloride ion ($Cl^-$), dissolved chlorine gas ($Cl_2$), and mixtures thereof.

Hydrogen peroxide is optionally present in the ORP water solution generally in the range of from about 0.01 ppm to about 200 ppm, and preferably from about 0.05 ppm to about 100 ppm. More preferably, hydrogen peroxide when optionally, is present in an amount from about 0.1 ppm and to about 40 ppm, and most preferably from about 1 ppm to about 4 ppm.

The total amount of free chlorine species is generally from about 10 ppm to about 400 ppm, preferably from about 50 ppm to about 200 ppm, and most preferably from about 50 ppm to about 80 ppm. The amount of hypochlorous acid is in the generally from about 15 ppm to about 35 ppm. The amount of sodium hypochlorite is generally in the range from about 25 ppm to about 50 ppm.

The ORP water solution comprising one or more chlorine species is stable as described herein. Generally, the ORP water solution is stable for at least about one week. Preferably, the ORP water solution is stable for at least about two months, more preferably, the ORP water solution is stable for at least about six months after its preparation. Even more preferably, the ORP water solution is stable for at least about one year, and most preferably for at least about three years.

The pH of the ORP water solution in this embodiment is generally from about 6 to about 8. Preferably, the pH of the ORP water solution is from about 6.2 to about 7.8, and most preferably from about 7.4 to about 7.6. An exemplary ORP water solution of the present invention can comprise, e.g., from about 15 ppm to about 35 ppm hypochlorous acid, from about 25 ppm to about 50 ppm sodium hypochlorite, a pH of from about 6.2 to about 7.8, and is stable for at least about one week.

While in no way limiting the present invention, it is believed that the control of pH permits a stable ORP water solution in which hydrogen peroxide and chlorine species, such as, by way of example, hypochlorous acid and hypochlorite ions, coexist.

Following its preparation, the ORP water solution or the formulation of the invention may be transferred to a sealed container for distribution and sale to end users such as, for example, health care facilities including hospitals, nursing homes, doctor offices, outpatient surgical centers, dental offices, and the like. The pharmaceutical dosage form according to the present invention comprises the formulation for topical administration as described herein and a sealed container into which the formulation is placed.

Any suitable sealed container may be used that maintains the sterility and stability of the ORP water solution or formulation held by the container. The container may be constructed of any material that is compatible with the ORP water solution or the components of the formulation, for example, the ORP water solution and the thickening agent. The container should be generally non-reactive so that the ions present in the ORP water solution do not react with the container to any appreciable extent.

Preferably, the container is constructed of plastic or glass. The plastic may be rigid so that the container is capable of being stored on a shelf. Alternatively, plastic may be flexible, such as a flexible bag.

Suitable plastics include polypropylene, polyester terephthalate (PET), polyolefin, cycloolefin, polycarbonate, ABS resin, polyethylene, polyvinyl chloride, and mixtures thereof. Preferably, the container comprises polyethylene selected from the group consisting of high-density polyethylene (HDPE), low-density polyethylene (LDPE), and linear low-density polyethylene (LLDPE). Most preferably, the container is high density polyethylene.

The container has an opening to permit dispensing of the ORP water solution or formulation for administration to a patient. The container opening may be sealed in any suitable manner. For example, the container may be sealed with a twist-off cap or stopper. Optionally, the opening may be further sealed with a foil layer.

The headspace gas of the sealed container may be air or other suitable gas that does not react with the ORP water solution or other components of a formulation containing the ORP water solution. Suitable headspace gases included nitrogen, oxygen, and mixtures thereof.

The invention further provides an ORP water solution comprising anode water and cathode water. Anode water is produced in the anode chamber of the electrolysis cell used in the present invention. Cathode water is produced in the cathode chamber of the electrolysis cell.

Cathode water is generally present in the ORP water solution of the solution in an amount of from about 10% by volume to about 90% by volume of the solution. Preferably, cathode water is present in the ORP water solution in an amount of from about 10% by volume to about 50% by volume, more preferably of from about 20% by volume to about 40% by volume of the solution, and most preferably of from about 20% by volume to about 30% by volume of the solution. Additionally, anode water may be present in the ORP water solution in an amount of from about 50% by volume to about 90% by volume of the solution.

As noted herein, the ORP water solution containing both anode water and cathode water can be acidic, neutral or basic, and generally has a pH of from about 1 to about 14. Typically, the pH of the ORP water solution is from about 3 to about 8. Preferably, the pH is about 6.4 to about 7.8, and more preferably from about 7.4 to about 7.6.

The ORP water solution of the invention has a wide variety of uses as a disinfectant, cleanser, cleaner, antiseptic and the like to control the activity of unwanted or harmful substances present in the environment. Substances that may be treated with the ORP water solution include, for example, organisms and allergens.

The ORP water solution may be used as a disinfectant, sterilization agent, decontaminant, antiseptic and/or cleanser. The ORP water solution of the invention is suitable for use in the following representative applications: medical, dental and/or veterinary equipment and devices; food industry (e.g., hard surfaces, fruits, vegetables, meats); hospitals/health care facilities (e.g., hard surfaces); cosmetic industry (e.g., skin cleaner); households (e.g., floors, counters, hard surfaces); electronics industry (e.g., cleaning circuitry, hard drives); and bio-terrorism (e.g., anthrax, infectious microbes).

The ORP water solution may also be applied to humans and/or animals to treat various conditions including, for example, the following: surgical/open wound cleansing agent; skin pathogen disinfection (e.g., for bacteria, mycoplasmas, virus, fungi, prions); battle wound disinfection; wound healing promotion; burn healing promotion; treatment of stomach ulcers; wound irrigation; skin fungi; psoriasis; athlete's foot; pinkeye and other eye infections; ear infections (e.g., swimmer's ear); lung/nasal/sinus infections; and other medical applications on or in the human or animal body. The use of ORP water solutions as a tissue cell growth promoter is further described in U.S. Patent Application Publication 2002/0160053 A1.

While in no way limiting the present invention, it is believed that the ORP water solution eradicates the bacteria with which it contacts as well as destroying the bacterial cellular components including proteins and DNA.

For instance, the ORP water solution is capable of at least about five log ($10^5$) reduction in the concentration of a sample of live microorganism selected from the group consisting of *Pseudomonas aeruginosa, Escherichia coli, Enterococcus hirae, Acinetobacter baumannii, Acinetobacter* species, *Bacteroides fragilis, Enterobacter aerogenes, Enterococcus faecalis*, Vancomycin Resistant-*Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, Streptococcus pyogenes, Candida albicans* and *Candida tropicalis*, within 30 seconds of exposure, when measured at least two months after preparation of the ORP water solution.

In one embodiment, the ORP water solution administered in accordance with the invention can reduce a sample of live microorganisms including, but not limited to, *Escherichia coli, Pseudomonas aeruginosa, Staphylococcus aureus* and *Candida albicans*, from an initial concentration of from about $1 \times 10^6$ to about $1 \times 10^8$ organisms/ml to a final concentration of about zero organisms/ml within about one minute of exposure when measured at least about two months after preparation of the ORP water solution. This corresponds to from about a six log ($10^6$) to about an eight log ($10^8$) reduction in organism concentration. Preferably, the ORP water solution is capable of achieving an about $10^6$-about $10^8$ reduction of *Escherichia coli, Pseudomonas aeruginosa, Staphylococcus aureus* or *Candida albicans* organisms when measured at least about six months after preparation, and more preferably when measured at least about one year after preparation.

Alternatively, the ORP water solution administered in accordance with the present invention can produce about a six log ($10^6$) reduction in the concentration of a spore suspension of *Bacillus athrophaeus* spores within about five minutes of exposure when measured at least about two months after preparation of the ORP water solution. Preferably, the ORP water solution administered in accordance with the invention can achieve about a $10^6$ reduction in the concentration of *Bacillus athrophaeus* spores when measured at least about six months after preparation, and more preferably when measured at least about one year after preparation. The ORP water solution is further capable of an about four log ($10^4$) reduction in the concentration of a spore suspension of *Bacillus athrophaeus* spores within about thirty (30) seconds of exposure, when measured at least two months after preparation of the ORP water solution. Preferably, the ORP water solution is capable of achieving this reduction in the concentration of *Bacillus athrophaeus* spores when measured at least about six months after preparation, and more preferably at least one about year after preparation.

The ORP water solution is also capable of an about six log ($10^6$) reduction in the concentration of fungal spores, such as *Aspergillis niger* spores, within about five to about ten minutes of exposure, when measured at least two months after preparation of the ORP water solution. Preferably, the ORP water solution is capable of achieving this reduction in the concentration of fungal spores when measured at least six months after preparation, and more preferably at least one year after preparation.

The ORP water solution administered in accordance with the invention further can produce more than 3 log ($10^3$) reduction in the concentration of viruses, such as Human Immunodeficiency Virus (HIV) and adenovirus, after from an about five to an about ten minutes exposure when measured at least about two months after preparation of the ORP water solution. Preferably, the ORP water solution can achieve a $>10^3$ reduction in the concentration of viruses when measured at least about six months after preparation, and more preferably when measured at least about one year after preparation.

The ORP water solution administered in accordance with the invention further can completely inhibit the growth of *Mycobacterium bovis* with an about five minutes exposure when measured at least about two months after preparation of the ORP water solution. Preferably, the ORP water solution can achieve the total inhibition in the concentration of *Mycobacteria* when measured at least about six months after preparation, and more preferably when measured at least about one year after preparation.

Accordingly, organisms that can be controlled, reduced, killed or eradicated by treatment with the ORP water solution include, but are not limited to, bacteria, fungi, yeasts, and viruses. Susceptible bacteria include, but are not limited to, *Escherichia coli, Staphylococcus aureus, Bacillus athrophaeus, Streptococcus pyogenes, Salmonella choleraesuis, Pseudomonas aeruginosa, Shingella dysenteriae*, and other susceptible bacteria. Fungi and yeasts that may be treated with the ORP water solution include, for example, *Candida albicans* and *Trichophyton mentagrophytes*. The ORP water solution may also be applied to viruses including, for example, adenovirus, human immunodeficiency virus (HIV), rhinovirus, influenza (e.g., influenza A), hepatitis (e.g., hepatitis A), coronavirus (responsible for Severe Acute Respiratory Syndrome (SARS)), rotavirus, respiratory syncytial virus, herpes simplex virus, varicella zoster virus, rubella virus, and other susceptible viruses.

In a preferred embodiment, the ORP water solution of the invention can be utilized in a variety of dental applications. First, the ORP water solution can be administered to patients for the routine disinfection of the oral cavity as part of an on-going program of oral hygiene. Second, the ORP water solution can be used to irrigate and/or disinfect oral tissues, tooth surfaces, cavities, or a tooth canal during oral or maxillo-facial procedures. Third, the ORP water solution can be administered to treat patients with damage to the oral tissues caused by, for example, oral or maxillo-facial procedures or disease. Finally, the ORP water solution can be used to disinfect objects related to dentistry, including, for example, dental instruments, irrigation lines of a dental office irrigation system, and dentures.

The use of antiseptic solutions, such as chlorhexidine, hydrogen peroxide, and bleach, in dental applications is known in the art. Current oral antiseptic solutions suffer from several disadvantages. Significantly, these oral antiseptics have high toxicity and can damage healthy tissue, resulting in a delay in healing time. Also, due to high toxicity, these oral antiseptics cannot be used for prolonged periods of time. Other adverse side affects include distortion of taste and staining of teeth. Conversely, ORP water solution is neither toxic or irritating and offers a improved approach to treatment and disinfection with oral antiseptic solutions.

In one embodiment, the ORP water solution can be administered to patients for the routine disinfection of the oral cavity as part of an on-going program of oral hygiene. The ORP water solution reduces levels of a wide spectrum of oral micro-organisms present in the oral cavity, thereby decreasing the occurrence of infectious diseases. The ORP water solution is administered to patients in any suitable manner. Preferably, the ORP water solution is administered as a mouthrinse or mouthwash. Preferably, patients rinse for at least about 30 seconds, more preferably for at least about one minute, and most preferably for at least about two minutes. Patients rinse daily, for example, or twice a day, or three times a day. Preferably, patients should rinse with ORP water solution after meals. Patients should brush and floss their teeth daily in combination with rinsing with ORP water solution. Patients can, for example, brush and floss their teeth before rinsing with the ORP water solution.

The reduction in oral microbial flora upon rinsing with the ORP water solution can be monitored. Oral microbioal flora levels are measured by culturing bacteriological swabs taken from the buccal mucosa. First, a baseline bacteriological swab is taken. The immediate reduction in oral microbial flora upon rinsing with ORP water solution can be determined by taking bacteriological swabs about ten minutes after rinsing and about fifteen minutes after rinsing. The long term reduction in oral microbial flora after a regimen of rinsing can also determined. For example, bacteriological swabs can be taken after one month of rinsing with the ORP water solution.

In a second embodiment, the ORP water solution can also be used as an irrigant and/or disinfectant during oral or maxillo-facial procedures. The ORP water solution can be used as the irrigant in ultrasonic scaling. Ultrasonic scaling is a procedure for the treatment of periodontal disease that removes plaque above and below the gum line. The ultrasonic scaler is operated in conjunction with a coolant or irrigant, and the cavitational activity within the solution contributes to the disruption and removal of plaque. Typically, the irrigant is water. The use of ORP water solution instead of water can slow the recolonization of microbes after removal of plaque. The treatment can be monitored with an assessment of inflammation, bleeding and pocket depths. The ultrasonic scaling with ORP water solution as the irrigant can be combined with other follow up treatments. The patient should brush and floss teeth daily. Preferably, the ultrasonic scaling is combined with the outpatient administration of ORP water solution in the form of a rinse. The patient rinses with ORP water solution for at least about two months or preferably at least about three months after the ultrasonic scaling procedure.

The ORP water solution is used an irrigant to cleanse and disinfect a cavity or a tooth canal during tooth restoration. Treatment for tooth decay or cavities consists of removing the decayed material and replacing it with restorative, or filling, material. First, the decayed material is removed by drilling. Next, the tooth is prepared for filling, including the steps of cleaning and disinfecting the dentin surface and/or enamel. The ORP water solution can be used as an irrigating solution to wash away debris such as debrided tooth material. Alternatively, the ORP water solution can be used to disinfect the dentin surface and/or enamel prior to filling. The ORP water solution can be applied by spraying the surface or moistening the surface with a brush or sponge. Similarly, the ORP water solution can be used as an irrigating solution during endodontic, or root canal, therapy. Endodontic therapy is required if the patient has a bacterial infection in a tooth's nerve tissue. Endodontic therapy consists of making an access hole to the pulp chamber with a drill, cleaning out the interior of the tooth, filling and sealing the interior of the tooth with root canal filling material, and filling in the access hole. As part of the cleaning step, irrigants are used to dissolve and flush out debris. The ORP water solution can be used as the irrigant during endodontic therapy. Alternatively, the ORP water solution can be used to disinfect the interior tooth after cleaning and prior to filling.

The ORP water solution is used as an irrigant and/or antiseptic during tooth extraction. After the tooth is extracted, the socket is irrigated with the ORP water solution to dissolve and flush out debris. The socket can be irrigated for at least about 30 seconds, or at least about one minute, or at least about two minutes, or longer if required. Preferably, the ORP water solution is used when the tooth is extracted due to an abscess or periodontal disease.

The ORP water solution is used as an irrigant and/or intraoperative antiseptic during maxillo-facial surgeries. Two recurrent problems in maxillo-facial surgery are bleeding and infection. The ORP water solution reduces bleeding in the surgical field. The ORP water solution also decreases post-operative healing time.

The ORP water solution is administered to patients undergoing maxillo-facial surgeries in any suitable manner. The ORP water solution can be administered immediately before, during, or immediately after the surgery. For example, the entire oral cavity can be rinsed once, twice, or three times prior to an incision. Preferably, the oral cavity is rinsed twice. The ORP water solution can be used to irrigate the operation site. Preferably, the ORP water solution is used to the flush operation site prior to suturing. The operation site can be irrigated for at least one minute, or at least two minutes, or at least three minutes, or longer if required.

In a third embodiment, the ORP water solution may be administered to patients with oral tissues damaged by disease or an oral or maxillo-facial procedure. Preferably, the ORP water solution is administered to patients suffering from periodontal diseases. Periodontal disease is a chronic bacterial infection that affects the gums and bone supporting the teeth and is one of the leading causes of tooth loss. Disease causing bacteria are present in the plaque above and below the gum line. Examples of periodontal diseases include gingivitis, or inflammation of the gingival tissues, and periodontitis, an inflammatory disease of the periodontium. Treatment with ORP water solution results in arresting the infection. There is also a reduction or elimination of inflammation and bleeding. Furthermore, in many cases, treatment with ORP water solution results in bone regeneration, halting the loss of periodontal attachment.

The ORP water solution is administered to patients suffering from periodontal diseases in any suitable manner. Preferably, the ORP water solution is administered as a mouthrinse or mouthwash. Preferably, patients rinse for at least about 30 seconds, more preferably for at least about one minute, and most preferably for at least about two minutes. Patients rinse daily, or twice a day, or preferably three times a day. Preferably, patients should rinse with ORP water solution after meals. Patients should brush and floss their teeth daily in combination with rinsing with ORP water solution. The treatment of periodontal disease using the ORP water solution may continue until the disease is resolved. Depending on the progression of the disease, the ORP water solution can be administered for at least about one month, or preferably about two months, or more preferably about three months, or longer. The administration of the ORP water solution can be combined with other treatments for periodontal diseases. Such treatments include mechanical removal of plaque and calculus and administration of antibiotics. Preferably, administration of the ORP water solution is combined with mechanical removal of plaque and calulus. Preferably, administration of the ORP water solution is not combined with antibiotics.

The ORP water solution can also be administered to patients with oral mucosal lesions or ulcers. Lesions are accompanied by pain and redness, and can impair chewing and swallowing. The lesions or ulcers have many causes. For example, denture stomatitis are lesions caused by wearing dentures. Patients who are immuno-compromised are also more likely to develop oral mucosal lesions or ulcers. Oral candidiasis, a fungal infection of the mucous membrane, causes lesions around the mouth. Oral mucositis is a common side effect experienced by patients undergoing cancer treatment, such as chemotherapy, radiation, or bone marrow transplant.

The ORP water solution is administered to patients suffering from oral mucosal lesions or ulcers in any suitable manner. Preferably, the ORP water solution is administered as a mouthrinse or mouthwash. Preferably, patients rinse for at least about 30 seconds, more preferably for at least about one minute, and most preferably for at least about two minutes. Patients rinse daily, or twice a day, or more preferably three times a day. The treatment of oral mucosal lesions or ulcers using the ORP water solution may continue until the lesions or ulcers are healed. Depending on the progression of the disease, the ORP water solution can be administered for about two weeks, for example, or about three weeks, or about four weeks, or about two months, or longer. The administration of the ORP water solution may be prophylactic in patients who are susceptible to oral mucosal lesions or ulcers.

The ORP water solution can be administered to patients to promote healing of oral tissues injured, for example, by dental procedures, oral surgery, or maxillo-facial surgery. The ORP water solution can be administered as post-operative follow up to such procedures or surgeries. Patients exhibit decreased healing time as compared to standard treatment without ORP water solution.

The ORP water solution is administered to patients after undergoing an oral or maxillo-facial procedure in any suitable manner. Preferably, the ORP water solution is administered as a mouthrinse or mouthwash. Preferably, patients rinse for at least about 30 seconds, more preferably for at least about one minute, and most preferably for at least about two minutes. Patients rinse daily, or preferably twice a day, or more preferably three times a day. The ORP water solution can be administered for about one week, or for about two weeks, or for about one month, or for about three months, or longer if necessary. The ORP water solution can be administered in combination with NSAID. The ORP water solution can also be administered in combination with antibiotics. Preferably, no antibiotic is administered.

The ORP water solution may be applied to disinfect and sterilize dental equipment. For example, to disinfect and sterilize dental instruments, the instrument is maintained in contact with the ORP water solution for a sufficient period of time to reduce the level of organisms present on the equipment to a desired level. To disinfect and sterilize dental office irrigation lines, for example, the irrigation lines are flushed with the ORP water solution. The reduction in bacteria levels can be measured by taking bacterial cultures before and after flushing the lines.

The ORP water solution may be applied to disinfect and sterilize dentures. For example, to disinfect and sterilize dental dentures, the dentures are maintained in contact with the ORP water solution for a sufficient period of time to reduce the level of organisms present on the equipment to a desired level. The dentures are maintained in contact with the ORP water solution in any suitable manner. For example, the dentures can be soaked in the ORP water solution. Alternatively, the dentures can be scrubbed with ORP water solution and a brush.

The ORP water solution administered in accordance with the present invention also can be used as the irrigation solution for hydrosurgery devices that are used to debride oral lesions. Suitable hydrosurgery devices can include, for example, the VersaJet devices sold in the United States by Smith and Nephew, Debritom in Europe by Medaxis, JetOx in the United States and Europe by DeRoyal or PulsaVac in Italy. It is believed that the ORP water solution can act synergistically with the device by reducing the microbial load in the oral lesions and by avoiding the formation of infectious mists during the debridement procedure. Thus the device may be used to debride an oral lesion with continuous irrigation, reduce the infection process and avoid the formation of infectious mists in accordance with the present invention.

The ORP water solution administered in accordance with the present invention also can be used as the irrigation solution for negative pressure devices that are used to reduce edema and increase the blood flow. Suitable negative pressure devices can include, e.g., one or more vacuum assisted wound closure devices such as, e.g., the V.A.C.® and V.A.C.® Instill™ devices sold in the United States by Kinetic Concepts, Inc. It is believed that the ORP water solution can act synergistically with the device by controlling the inflammatory-allergic process while reducing the microbial load. Thus the device may be applied to an open oral lesion with intermittent or continuous irrigation to treat or prevent tissue infection or necrosis in accordance with the present invention.

The administration of ORP solution can optionally be combined with the administration of topical and/or systemic antibiotics. Suitable antibiotics can include, without limitation, penicillin, cephalosporins or other β-lactams, macrolides (e.g., erythromycin, 6-O-methylerythromycin, and azithromycin), fluoroquinolones, sulfonamides, tetracyclines, aminoglycosides, clindamycin, quinolones, metronidazole, vancomycin, chloramphenicol, antibacterially effective derivatives thereof, and combinations thereof. Suitable anti-infective agents also can include antifungal agents such as, for example, amphotericin B, fluconazole, flucytosine, ketoconazole, miconazole, derivatives thereof, and combinations thereof. Suitable anti-inflammatory agents can include, e.g., one or more anti-inflammatory drugs, e.g., one or more anti-inflammatory steroids or one or more non-steroidal anti-inflammatory drugs (NSAIDs). Exemplary anti-inflammatory drugs can include, e.g., cyclophilins, FK binding proteins, anti-cytokine antibodies (e.g. anti-TNF), steroids, and NSAIDs.

It has been found that the ORP water solution administered in accordance with the invention is virtually free of toxicity to normal tissues and normal mammalian cells. The ORP water solution administered in accordance with the invention causes no significant decrease in the viability of eukaryotic cells, no significant increase in apoptosis, no significant acceleration of cell aging and/or no significant oxidative DNA damage in mammalian cells. The non-toxicity is particularly advantageous, and perhaps even surprising, given that the disinfecting power of the ORP water solution administered in accordance with the invention is roughly equivalent to that of hydrogen peroxide, yet is significantly less toxic than hydrogen peroxide is to normal tissues and normal mammalian cells. These findings demonstrate that the ORP water solution administered in accordance with the present invention is safe for use, e.g., in mammals, including humans.

For the ORP water solution administered in accordance with the invention, the cell viability rate is preferably at least about 65%, more preferably at least about 70%, and still more preferably at least about 75% after an about 30 minute exposure to the ORP water solution. In addition, the ORP water solution administered in accordance with the invention preferably causes only up to about 10% of cells, more preferably only up to about 5% of cells, and still more preferably only up to about 3% of cells to expose Annexin-V on their cellular surfaces when contacted with the ORP water solution for up to about thirty minutes or less (e.g., after about thirty minutes or after about five minutes of contact with the ORP water solution). Further, the ORP water solution administered in accordance with the invention preferably causes less than about 15% of cells, more preferably less than about 10% of cells, and still more preferably less than about 5% of cells to express the SA-β-galactosidase enzyme after chronic exposure to the OPR water solution. The ORP water solution administered in accordance with the invention preferably causes caused the same fraction of the oxidative DNA adduct formation caused by saline solution, e.g., less than about 20% of the oxidative DNA adduct formation, less than about 10% of the oxidative DNA adduct formation, or about 5% or less of the oxidative DNA adduct formation normally caused by hydrogen peroxide in cells treated under equivalent conditions.

The ORP water solution administered in accordance with the invention produces no significant RNA degradation. Accordingly, RNA extracted from human cell cultures after an about 30 minutes exposure to the ORP water solution or r at about 3 hours after an about 30 minute-exposure, and analyzed by denaturing gel electrophoresis, will typically show no significant RNA degradation and will typically exhibit two discreet bands corresponding to the ribosomal eukaryotic RNAs (i.e. 28S and 18S) indicating that the ORP water solution administered in accordance with the invention leaves the RNA substantially intact. Similarly, RNA extracted from human cell cultures after about 30 minutes of exposure to the ORP water solution or after about 3 hours of exposure, can be subjected reverse transcription and amplification (RT-PCR) of the constitutive human GAPDH (Glyceraldehyde-3-phosphate dehydrogenase) gene and result in a strong GAPDH band on gel electrophoresis of the RT-PCR products. By contrast, cells treated with HP for a similar period show significant RNA degradation and little if any GAPDH RT-PCR product.

The ORP water of the invention is also suitable for use in controlling the activity of allergens present in the environment. As used herein, allergens include any substance other than bacteria, fungi, yeasts, or viruses that can trigger an adverse immune response, or allergy, in susceptible people or animals. Asthma is a common physiological response following exposure to one or more allergens. Allergens may be either viable (i.e., from living or dead organisms) or non-viable (e.g., non-living such as textiles), and may be present in the environment, for example, in households and/or workplaces.

Protein-based household allergens that may be treated with the ORP water include, for example, animal fur, skin, and feces, household dust, weeds, grasses, trees, mites, and pollens. Animal allergens include, for example, cat epithelium, dog epithelium, horse dander, cow dander, dog dander, guinea pig epithelium, goose feathers, mouse epithelium, mouse urine, rat epithelium and rat urine.

Occupational allergens include, for example, high-molecular-weight agents, such as natural proteins generally derived from plant or animal proteins, and low-molecular-weight chemicals, such as diisocyanates, and other material found in some textiles. Other chemical allergens that may be present in the workplace include, for example, anhydrides, antibiotics, wood dust and dyes. Numerous proteins may be occupational allergens including vegetable gums, enzymes, animal proteins, insects, plant proteins, and legumes.

Additional allergens suitable for treatment by the ORP water solution are described in Korenblat and Wedner, Allergy Theory and Practice (1992) and Middleton, Jr., Allergy Principles and Practice (1993).

The ORP water solution of the invention may be used or applied in any suitable amount to provide the desired bactericidal, virucidal, germicidal and/or anti-allergenic effect.

The ORP water solution may be applied to disinfect and sterilize in any suitable manner. For example, to disinfect and sterilize medical or dental equipment, the equipment is maintained in contact with the ORP water solution for a sufficient period of time to reduce the level of organisms present on the equipment to a desired level.

For disinfection and sterilization of hard surfaces, the ORP water solution may be applied to the hard surface directly from a container in which the ORP water solution is stored. For example, the ORP water solution may be poured, sprayed or otherwise directly applied to the hard surface. The ORP water solution may then be distributed over the hard surface using a suitable substrate such as, for example, cloth, fabric or paper towel. In hospital applications, the substrate is preferably sterile. Alternatively, the ORP water solution may be first be applied to a substrate such as cloth, fabric or paper towel. The wetted substrate is then contacted with the hard surface. Alternatively, the ORP water solution may be applied to hard surfaces by dispersing the solution into the air as described herein. The ORP water solution may be applied in a similar manner to humans and animals.

An implement may optionally be used to apply the ORP water solution to hard surfaces such as floors, walls, and ceilings. For example, the ORP water solution may be dispensed onto a mop head for application to floors. Other suitable implements for applying the ORP water solution to hard surfaces are described in U.S. Pat. No. 6,663,306.

The invention further provides a cleaning wipe comprising a water insoluble substrate and the ORP water solution as described herein, wherein the ORP water solution is dispensed onto the substrate. The ORP water solution may be impregnated, coated, covered or otherwise applied to the substrate. Preferably, the substrate is pretreated with the ORP water solution before distribution of the cleaning wipes to end users.

The substrate for the cleaning wipe may be any suitable water-insoluble absorbent or adsorbent material. A wide variety of materials can be used as the substrate. It should have sufficient wet strength, abrasivity, loft and porosity. Further, the substrate must not adversely impact the stability of the ORP water solution. Examples include non woven substrates, woven substrates, hydroentangled substrates and sponges.

The substrate may have one or more layers. Each layer may have the same or different textures and abrasiveness. Differing textures can result from the use of different combinations of materials or from the use of different manufacturing processes or a combination thereof. The substrate should not dissolve or break apart in water. The substrate provides the vehicle for delivering the ORP water solution to the surface to be treated.

The substrate may be a single nonwoven sheet or multiple nonwoven sheets. The nonwoven sheet may be made of wood pulp, synthetic fibers, natural fibers, and blends thereof. Suitable synthetic fibers for use in the substrate include, without limitation, polyester, rayon, nylon, polypropylene, polyethylene, other cellulose polymers, and mixtures of such fibers. The nonwovens may include nonwoven fibrous sheet materials which include meltblown, coform, air-laid, spun bond, wet laid, bonded-carded web materials, hydroentangled (also known as spunlaced) materials, and combinations thereof. These materials can comprise synthetic or natural fibers or combinations thereof. A binder may optionally be present in the substrate.

Examples of suitable nonwoven, water insoluble substrates include 100% cellulose Wadding Grade 1804 from Little Rapids Corporation, 100% polypropylene needlepunch material NB 701-2.8-W/R from American Nonwovens Corporation, a blend of cellulosic and synthetic fibres-Hydraspun 8579 from Ahlstrom Fibre Composites, and 70% Viscose/30% PES Code 9881 from PGI Nonwovens Polymer Corp. Additional examples of nonwoven substrates suitable for use in the cleaning wipes are described in U.S. Pat. Nos. 4,781,974, 4,615,937, 4,666,621, and 5,908,707, and International Patent Application Publications WO 98/03713, WO 97/40814, and WO 96/14835.

The substrate may also be made of woven materials, such as cotton fibers, cotton/nylon blends, or other textiles. Regenerated cellulose, polyurethane foams, and the like, which are used in making sponges, may also be suitable for use.

The liquid loading capacity of the substrate should be at least about 50%-1000% of the dry weight thereof, most preferably at least about 200%-800%. This is expressed as loading ½ to 10 times the weight of the substrate. The weight of the substrate varies without limitation from about 0.01 to about 1,000 grams per square meter, most preferably 25 to 120 grams/$m^2$ (referred to as "basis weight") and typically is produced as a sheet or web which is cut, die-cut, or otherwise sized into the appropriate shape and size. The cleaning wipes will preferably have a certain wet tensile strength which is without limitation about 25 to about 250 Newtons/m, more preferably about 75-170 Newtons/m.

The ORP water solution may be dispensed, impregnated, coated, covered or otherwise applied to the substrate by any suitable method. For example, individual portions of substrate may be treated with a discrete amount of the ORP water solution. Preferably, a mass treatment of a continuous web of substrate material with the ORP water solution is carried out. The entire web of substrate material may be soaked in the ORP water solution. Alternatively, as the substrate web is spooled, or even during creation of a nonwoven substrate, the ORP water solution is sprayed or metered onto the web. A stack of individually cut and sized portions of substrate may be impregnated or coated with the ORP water solution in its container by the manufacturer.

The cleaning wipes may optionally contain additional components to improve the properties of the wipes. For example, the cleaning wipes may further comprise polymers, surfactants, polysaccharides, polycarboxylates, polyvinyl alcohols, solvents, chelating agents, buffers, thickeners, dyes, colorants, fragrances, and mixtures thereof to improve the properties of the wipes. These optional components should not adversely impact the stability of the ORP water solution. Examples of various components that may optionally be included in the cleaning wipes are described in U.S. Pat. Nos. 6,340,663, 6,649,584 and 6,624,135.

The cleaning wipes of the invention can be individually sealed with a heat-sealable or glueable thermoplastic overwrap (such as polyethylene, Mylar, and the like). The wipes can also be packaged as numerous, individual sheets for more economical dispensing. The cleaning wipes may be prepared by first placing multiple sheets of the substrate in a dispenser and then contacting the substrate sheets with the ORP water solution of the invention. Alternatively, the cleaning wipes can be formed as a continuous web by applying the ORP water solution to the substrate during the manufacturing process and then loading the wetted substrate into a dispenser.

The dispenser includes, but is not limited to, a canister with a closure, or a tub with closure. The closure on the dispenser is to seal the moist wipes from the external environment and to prevent premature volatilization of the liquid ingredients.

The dispenser may be made of any suitable material that is compatible with both the substrate and the ORP water solution. For example, the dispenser may be made of plastic, such as high density polyethylene, polypropylene, polycarbonate, polyethylene terephthalate (PET), polyvinyl chloride (PVC), or other rigid plastics.

The continuous web of wipes may be threaded through a thin opening in the top of the dispenser, most preferably, through the closure. A means of sizing the desired length or size of the wipe from the web would then be needed. A knife blade, serrated edge, or other means of cutting the web to desired size may be provided on the top of the dispenser, for non-limiting example, with the thin opening actually doubling in duty as a cutting edge. Alternatively, the continuous web of wipes may be scored, folded, segmented, perforated or partially cut into uniform or non-uniform sizes or lengths, which would then obviate the need for a sharp cutting edge. Further, the wipes may be interleaved, so that the removal of one wipe advances the next.

The ORP water solution of the invention may alternatively be dispersed into the environment through a gaseous medium, such as air. The ORP water solution may be dispersed into the air by any suitable means. For example, the ORP water solution may be formed into droplets of any suitable size and dispersed into a room.

For small scale applications, the ORP water solution may be dispensed through a spray bottle that includes a standpipe and pump. Alternatively, the ORP water solution may be packaged in aerosol containers. Aerosol containers generally include the product to be dispensed, propellant, container, and valve. The valve includes both an actuator and dip tube. The contents of the container are dispensed by pressing down on the actuator. The various components of the aerosol container are compatible with the ORP water solution. Suitable propellants may include a liquefied halocarbon, hydrocarbon, or halocarbon-hydrocarbon blend, or a compressed gas such as carbon dioxide, nitrogen, or nitrous oxide. Aerosol systems typically yield droplets that range in size from about 0.10 µm to about 100 µm, preferably from about 0.15 µm to about 5 µm.

The ORP water solution may be dispensed in aerosol form as part of an inhaler system for treatment of infections in the lungs and/or air passages or for the healing of wounds in such parts of the body.

For larger scale applications, any suitable device may be used to disperse the ORP water solution into the air including, but not limited to, humidifiers, misters, foggers, vaporizers, atomizers, water sprays, and other spray devices. Such devices permit the dispensing of the ORP water solution on a continuous basis. An ejector which directly mixes air and water in a nozzle may be employed. The ORP water solution may be converted to steam, such as low pressure steam, and released into the air stream. Various types of humidifiers may be used such as ultrasonic humidifiers, stream humidifiers or vaporizers, and evaporative humidifiers.

The particular device used to disperse the ORP water solution may be incorporated into a ventilation system to provide for widespread application of the ORP water solution throughout an entire house or healthcare facility (e.g., hospital, nursing home, etc.).

The ORP water solution may optionally contain a bleaching agent. The bleaching agent may be any suitable material that lightens or whitens a substrate. The ORP water solution containing a bleaching agent can be used in home laundering to disinfect and sterilize bacteria and germs as well as brighten clothing. Suitable bleaching agents include, but are not limited to, chlorine-containing bleaching agents and peroxide-containing bleaching agents. Mixtures of bleaching agents may also be added to the ORP water solution. Preferably, the bleaching agent is added in the form of an aqueous solution to the ORP water solution.

Chlorine-containing bleaching agents useful in the present invention include chlorine, hypochlorites, N-chloro compounds, and chlorine dioxide. Preferably, the chlorine-containing bleaching agent added to the ORP water solution is sodium hypochlorite or hypochlorous acid. Other suitable chlorine-containing bleaching agents include chlorine, calcium hypochlorite, bleach liquor (e.g., aqueous solution of calcium hypochlorite and calcium chloride), bleaching powder (e.g., mixture of calcium hypochlorite, calcium hydroxide, calcium chloride, and hydrates thereof), dibasic magnesium hypochlorite, lithium hypochlorite, chlorinated trisodium phosphate. Mixtures of chlorine-containing bleaching agents may be used.

The addition of a bleaching agent to the ORP water solution may be carried out in any suitable manner. Preferably, an aqueous solution containing the bleaching agent is first prepared. The aqueous solution containing the bleaching agent may be prepared using household bleach (e.g., Clorox® bleach) or other suitable source of chlorine-containing bleaching agent or other bleaching agent. The bleaching agent solution is then combined with the ORP water solution.

The bleaching agent may be added to the ORP water solution in any suitable amount. Preferably, the ORP water solution containing a bleaching agent is non-irritating to human or animal skin. Preferably, the total chloride ion content of the ORP water solution containing a chlorine-containing bleaching agent is from about 1000 ppm to about 5000 ppm, and preferably from about 1000 ppm to about 3000 ppm. The pH of the ORP water solution containing a chlorine-containing bleaching agent is preferably from about 8 to about 10, and the oxidative-reductive potential is from about +700 mV to about +800 mV.

The ORP water solution may optionally contain additives suitable for the household and workplace cleaning environment. Suitable additives include surfactants, such as detergents and cleaning agents. Perfumes or other scent-producing compounds may also be included to enhance consumer reception of the ORP water solution.

The present invention further provides a process for producing an ORP water solution using at least one electrolysis cell comprising an anode chamber, cathode chamber and salt solution chamber located between the anode and cathode chambers, wherein the ORP water solution comprises anode water and cathode water. A diagram of a typical three chamber electrolysis cell useful in the invention is shown in FIG. 1.

The electrolysis cell 100 has an anode chamber 102, cathode chamber 104 and salt solution chamber 106. The salt solution chamber is located between the anode chamber 102 and cathode chamber 104. The anode chamber 102 has an inlet 108 and outlet 110 to permit the flow of water through the anode chamber 102. The cathode chamber 104 similarly has an inlet 112 and outlet 114 to permit the flow of water through the cathode chamber 104. The salt solution chamber 106 has an inlet 116 and outlet 118. The electrolysis cell 100 preferably includes a housing to hold all of the components together.

The anode chamber 102 is separated from the salt solution chamber by an anode electrode 120 and an anion ion exchange membrane 122. The anode electrode 120 may be positioned adjacent to the anode chamber 102 with the membrane 122 located between the anode electrode 120 and the salt solution chamber 106. Alternatively, the membrane 122 may be positioned adjacent to the anode chamber 102 with the anode electrode 120 located between the membrane 122 and the salt solution chamber 106.

The cathode chamber 104 is separated from the salt solution chamber by a cathode electrode 124 and a cathode ion exchange membrane 126. The cathode electrode 124 may be positioned adjacent to the cathode chamber 104 with the membrane 126 located between the cathode electrode 124 and the salt solution chamber 106. Alternatively, the membrane 126 may be positioned adjacent to the cathode chamber 104 with the cathode electrode 124 located between the membrane 126 and the salt solution chamber 106.

The electrodes are generally constructed of metal to permit a voltage potential to be applied between the anode chamber and cathode chamber. The metal electrodes are generally planar and have similar dimensions and cross-sectional surface area to that of the ion exchange membranes. The electrodes are configured to expose a substantial portion of the surface of the ion exchange members to the water in their respective anode chamber and cathode chamber. This permits the migration of ionic species between the salt solution chamber, anode chamber and cathode chamber. Preferably, the electrodes have a plurality of passages or apertures evenly spaced across the surface of the electrodes.

A source of electrical potential is connected to the anode electrode 120 and cathode electrode 124 so as to induce an oxidation reaction in the anode chamber 102 and a reduction reaction in the cathode chamber 104.

The ion exchange membranes 122 and 126 used in the electrolysis cell 100 may be constructed of any suitable material to permit the exchange of ions between the salt solution chamber 106 and the anode chamber 102 such as chloride ions ($Cl^-$) and between the salt solution salt solution chamber 106 and the cathode chamber 104 such as sodium ions ($Na^+$). The anode ion exchange membrane 122 and cathode ion exchange membrane 126 may be made of the same or different material of construction. Preferably, the anode ion exchange membrane comprises a fluorinated polymer. Suitable fluorinated polymers include, for example, perfluorosulfonic acid polymers and copolymers such as perfluorosulfonic acid/PTFE copolymers and perfluorosulfonic acid/TFE copolymers. The ion exchange membrane may be constructed of a single layer of material or multiple layers.

The source of the water for the anode chamber 102 and cathode chamber 104 of the electrolysis cell 100 may be any suitable water supply. The water may be from a municipal water supply or alternatively pretreated prior to use in the electrolysis cell. Preferably, the pretreated water is selected from the group consisting of softened water, purified water, distilled water, and deionized water. More preferably, the pretreated water source is ultrapure water obtained using reverse osmosis purification equipment.

The salt water solution for use in the salt solution chamber 106 may be any aqueous salt solution that contains suitable ionic species to produce the ORP water solution. Preferably, the salt water solution is an aqueous sodium chloride (NaCl) salt solution, also commonly referred to as a saline solution. Other suitable salt solutions include other chloride salts such as potassium chloride, ammonium chloride and magnesium chloride as well as other halogen salts such as potassium and bromine salts. The salt solution may contain a mixture of salts.

The salt solution may have any suitable concentration. The salt solution may be saturated or concentrated. Preferably, the salt solution is a saturated sodium chloride solution.

Figure 2:
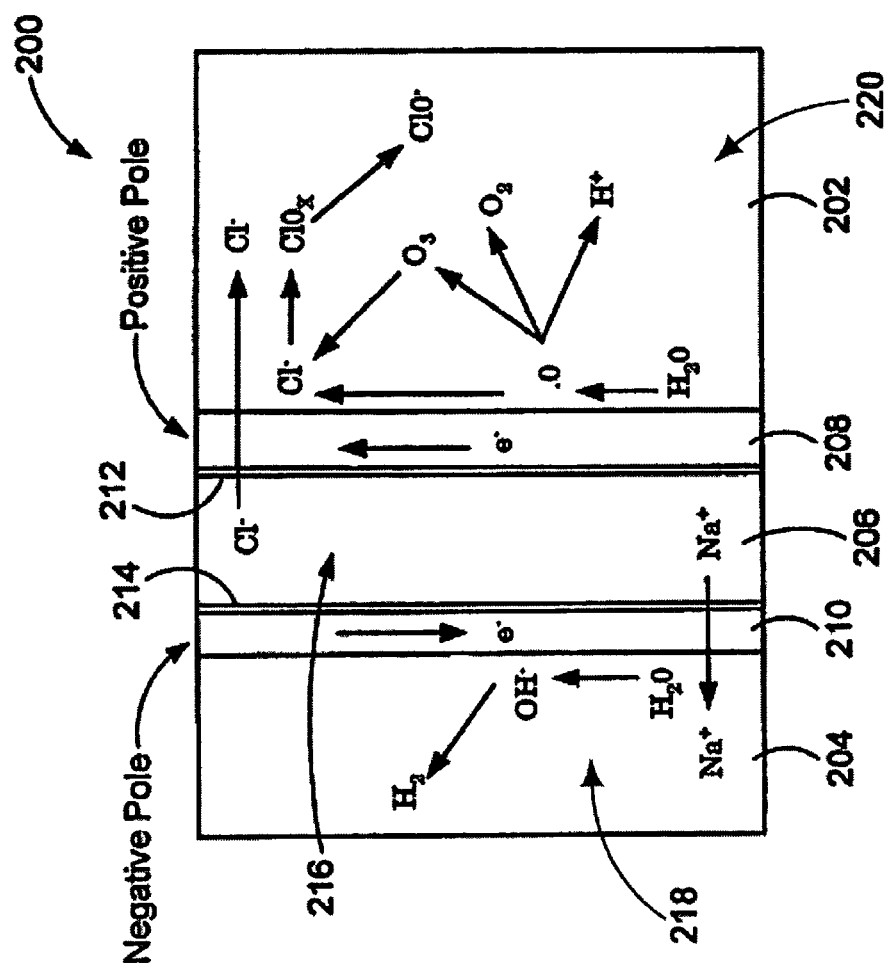
FIG. 2 illustrates a three-chambered electrolysis cell and depicts ionic species generated therein.

The various ionic species produced in the three chambered electrolysis cell useful in the invention are illustrated in FIG. 2. The three chambered electrolysis cell 200 includes an anode chamber 202, cathode chamber 204, and a salt solution chamber 206. Upon application of a suitable electrical current to the anode 208 and cathode 210, the ions present in the salt solution flowing through the salt solution chamber 206 migrate through the anode ion exchange membrane 212 and cathode ion exchange membrane 214 into the water flowing through the anode chamber 202 and cathode chamber 204, respectively.

Positive ions migrate from the salt solution 216 flowing through the salt solution chamber 206 to the cathode water 218 flowing through the cathode chamber 204. Negative ions migrate from the salt solution 216 flowing through the salt solution chamber 206 to the anode water 220 flowing through the anode chamber 202.

Preferably, the salt solution 216 is aqueous sodium chloride (NaCl) that contains both sodium ions ($Na^+$) and chloride ions ($Cl^-$) ions. Positive $Na^+$ ions migrate from the salt solution 216 to the cathode water 218. Negative $Cl^-$ ions migrate from the salt solution 216 to the anode water 220.

The sodium ions and chloride ions may undergo further reaction in the anode chamber 202 and cathode chamber 204. For example, chloride ions can react with various oxygen ions and other species (e.g., oxygen free radicals, $O_2$, $O_3$) present in the anode water 220 to produce ClOn- and $ClO^-$. Other reactions may also take place in the anode chamber 202 including the formation of oxygen free radicals, hydrogen ions ($H^+$), oxygen (as $O_2$), ozone ($O_3$), and peroxides. In the cathode chamber 204, hydrogen gas ($H_2$), sodium hydroxide (NaOH), hydroxide ions ($OH^-$), ClOn- ions, and other radicals may be formed.

Figure 3:
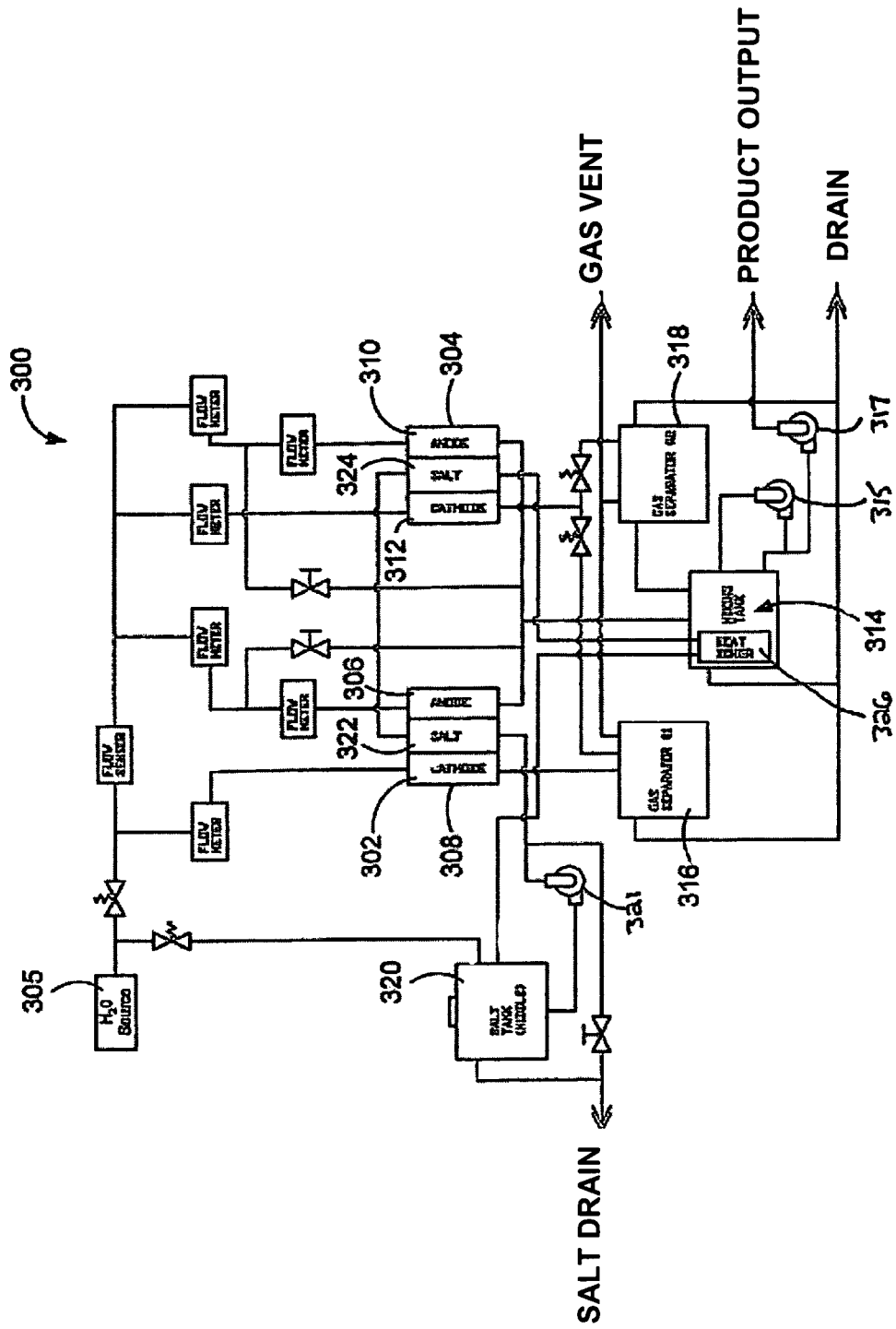
FIG. 3 is a schematic flow diagram of a process for producing an oxidative reductive potential water of the present invention.

The invention further provides for a process and apparatus for producing an ORP water solution using at least two three chambered electrolysis cells. A diagram of a process for producing an ORP water solution using two electrolysis cells of the invention is shown in FIG. 3.

The process 300 includes two three-chambered electrolytic cells, specifically a first electrolytic cell 302 and second electrolytic cell 304. Water is transferred, pumped or otherwise dispensed from the water source 305 to anode chamber 306 and cathode chamber 308 of the first electrolytic cell 302 and to anode chamber 310 and cathode chamber 312 of the second electrolytic cell 304. Typically, the process of the invention can produce from about 1 liter/minute to about 50 liters/minute of ORP water solution. The production capacity may be increased by using additional electrolytic cells. For example, three, four, five, six, seven, eight, nine, ten or more three-chambered electrolytic cells may be used to in increase the output of the ORP water solution of the invention.

The anode water produced in the anode chamber 306 and anode chamber 310 is collected are collected in the mixing tank 314. A portion of the cathode water produced in the cathode chamber 308 and cathode chamber 312 is collected in mixing tank 314 and combined with the anode water. The remaining portion of cathode water produced in the process is discarded. The cathode water may optionally be subjected to gas separator 316 and/or gas separator 318 prior to addition to the mixing tank 314. The gas separators remove gases such as hydrogen gas that are formed in cathode water during the production process.

The mixing tank 314 may optionally be connected to a recirculation pump 315 to permit homogenous mixing of the anode water and portion of cathode water from electrolysis cells 302 and 304. Further, the mixing tank 314 may optionally include suitable devices for monitoring the level and pH of the ORP water solution. The ORP water solution may be transferred from the mixing tank 314 via pump 317 for application in disinfection or sterilization at or near the location of the mixing tank. Alternatively, the ORP water solution may be dispensed into suitable containers for shipment to a remote site (e.g., warehouse, hospital, etc.).

The process 300 further includes a salt solution recirculation system to provide the salt solution to salt solution chamber 322 of the first electrolytic cell 302 and the salt solution chamber 324 of the second electrolytic cell 304. The salt solution is prepared in the salt tank 320. The salt solution is transferred via pump 321 to the salt solution chambers 322 and 324. Preferably, the salt solution flows in series through salt solution chamber 322 first followed by salt solution chamber 324. Alternatively, the salt solution may be pumped to both salt solution chambers simultaneously.

Before returning to the salt tank 320, the salt solution may flow through a heat exchanger 326 in the mixing tank 314 to control the temperature of the ORP water solution as needed.

The ions present in the salt solution are depleted over time in the first electrolytic cell 302 and second electrolytic cell 304. An additional source of ions may periodically be added to the mixing tank 320 to replace the ions that are transferred to the anode water and cathode water. The additional source of ions may be used to maintain a constant pH of the salt solution which tends to drop (i.e., become acidic) over time. The source of additional ions may be any suitable compound including, for example, salts such as sodium chloride. Preferably, sodium hydroxide is added to the mixing tank 320 to replace the sodium ions ($Na^+$) that are transferred to the anode water and cathode water.

In another embodiment, the invention provides an apparatus for producing an oxidative reductive potential water solution comprising at least two three-chambered electrolytic cells. Each of the electrolytic cells includes an anode chamber, cathode chamber, and salt solution chamber separating the anode and cathode chambers. The apparatus includes a mixing tank for collecting the anode water produced by the electrolytic cells and a portion of the cathode water produced by one or more of the electrolytic cells. Preferably, the apparatus further includes a salt recirculation system to permit recycling of the salt solution supplied to the salt solution chambers of the electrolytic cells.

The following examples further illustrate the invention but, of course, should not be construed as in any way limiting in its scope.

EXAMPLES 1-3

These examples demonstrate the unique features of the ORP water solution of the invention. The samples of the ORP water solution in Examples 1-3 were analyzed in accordance with the methods described herein to determine the physical properties and levels of ionic and other chemical species present in each sample. The results obtained for chlorine dioxide, ozone and hydrogen peroxide are based on standard tests used to measure such species; however, the results may be indicative of different species, which can also generate positive test results. Further, it has been reported that chlorine dioxide, ozone and hydrogen peroxide can react with hypochlorite resulting in their consumption and the production of other species (e.g., HCl and $O_2$). The pH, oxidative-reductive potential (ORP) and ionic species present are set forth in Table 1 for each sample of the ORP water solution.

TABLE 1

Physical Characteristics and Ion Species Present for the ORP Water Solution Sample

|  | EXAMPLE 1 | EXAMPLE 2 | EXAMPLE 3 |
| --- | --- | --- | --- |
| pH | 7.45 | 7.44 | 7.45 |
| ORP (mV) | +879 | +881 | +874 |
| Total $Cl^-$ (ppm) | 110 | 110 | 120 |
| Bound $Cl^-$ (ppm) | 5 | 6 | 6 |

The ORP water solution has suitable physical characteristics for use in disinfection, sterilization and/or cleaning.

EXAMPLES 4-10

These examples demonstrate the addition of a bleaching agent to the ORP water solution according to the invention in various amounts. In particular, these examples demonstrate the antimicrobial activity and fabric bleaching ability of the compositions.

A 10% Clorox® bleach solution was prepared using distilled water. The following solutions were then prepared using the 10% bleach solution: 80% ORP water solution/20% bleach (Example 4); 60% ORP water solution/40% bleach (Example 5); 40% ORP water solution/60% bleach (Example 6); 20% ORP water solution/80% bleach (Example 7); and 0% ORP water solution/100% bleach (Example 8). Two control solutions were also used for comparison including 100% ORP water solution/0% bleach (Example 9) and an ORP water solution with 0.01% Tween 20 detergent (Example 10). The physical characteristics of these samples were determined, specifically pH, oxidative-reductive potential (ORP), total chlorine ($Cl^-$) content, hypochlorous acid ($HClO^-$) content, chlorine dioxide content and peroxide content, and are set forth in Table 2.

TABLE 2

Physical Characteristics of ORP Water Solution/Bleach Compositions

|  | pH | ORP (mV) | Total $Cl^-$ (ppm) | $HClO^-$ (ppm) |
| --- | --- | --- | --- | --- |
| Ex. 4 | 8.92 | +789 | 1248 | 62 |
| Ex. 5 | 9.20 | +782 | 2610 | 104 |
| Ex. 6 | 9.69 | +743 | 4006 | 80 |
| Ex. 7 | 9.86 | +730 | 4800 | 48 |
| Ex. 8 | 9.80 | +737 | 5000 | 50 |
| Ex. 9 | 7.06 | +901 | 64 | 32 |
| Ex. 10 | 6.86 | +914 | 51 | 26 |

The large bolus of chlorine ions added as part of the bleaching agent prevented the accurate measurement of the chlorine dioxide and peroxide levels as indicated with the n.d. designations. Also, the results obtained for chlorine dioxide and peroxide are based on standard tests used to measure such species; however, the results may be indicative of different species which can also generate positive test results. Further, it has been reported that chlorine dioxide, ozone and hydrogen peroxide can react with hypochlorite resulting their consumption and the production of other species (e.g., HCl and $O_2$). As these examples demonstrate, the hypochlorous acid levels of the ORP water solution with and without the addition of a bleaching agent are similar.

The samples of Examples 4-10 were subjected to a high spore count test using *Bacillus subtilis* var. *niger* spores (ATCC #9372 obtained from SPS Medical of Rush, N.Y.). Spore suspensions were concentrated (by evaporation in a sterile hood) to $4 \times 10^6$ spores per 100 microliters. A 100 microliter sample of the spore suspension were mixed with 900 microliters of each of the samples in Examples 4-10. The samples were incubated at room temperature for periods of 1 to 5 minutes as set forth in Table 3. At the indicated times, 100 microliters of the incubated samples were plated onto individual TSA plates and incubated for 24 hours at 35° C.±2° C., after which the number of resulting colonies on each plate was determined. The control plates demonstrated that the starting spore concentrations were $>1 \times 10^6$ spores/100 microliters. The concentration of *Bacillus* spores for the various samples at the various incubation times (as the average of two determinations) is set forth in Table 3.

TABLE 3

*Bacillus* Spore Concentrations (spores/100 microliters)

| | 1 minute | 2 minutes | 3 minutes | 4 minutes | 5 minutes |
|---|---|---|---|---|---|
| Ex. 4 | >>1000 | 411 | 1 | 0 | 2 |
| Ex. 5 | >>1000 | 1000 | 1 | 0 | 0 |
| Ex. 6 | >>1000 | >>1000 | >1000 | 22 | 0 |
| Ex. 7 | >>1000 | >>1000 | >1000 | 15 | 0 |
| Ex. 8 | >>1000 | >>1000 | >1000 | 3 | 1 |
| Ex. 9 | >>1000 | 74 | 0 | 0 | 0 |
| Ex 10 | >>1000 | 239 | 3 | 0 | 0 |

As these results demonstrate, as the concentration of bleach (as 10% aqueous bleach solution) increases, the amount of *Bacillus* spores killed is reduced for the samples incubated for 2-3 minutes. However, for samples incubated for 5 minutes, the bleach concentration does not impact *Bacillus* spore kill. Further, the results demonstrate that the addition of 0.01% detergent to the ORP water solution does not reduce spore kill.

The samples of Examples 4-10 were subjected to a fabric bleaching test. The fabric upon which the samples were tested was a 100% rayon children's t-shirt with dark blue dye patches. Two inch square pieces of dyed fabric were placed into 50 mL plastic tubes. Each fabric piece was covered by a sample of the solution in Examples 4-10. The elapsed time until complete bleaching was obtained, as determined by the whitening of the fabric, is set forth in Table 4.

TABLE 4

Time Until Complete Bleaching of Fabric Sample

| Example | Time |
|---|---|
| Ex. 4 | 39 minutes |
| Ex. 5 | 23 minutes |
| Ex. 6 | 18 minutes |
| Ex. 7 | 19 minutes |
| Ex. 8 | 10 minutes |
| Ex. 9 | >6 hours |
| Ex. 10 | >6 hours |

As demonstrated by these examples, as the concentration of the ORP water solution increases in the composition, the time until complete bleaching is achieved increases.

EXAMPLE 11

This example relates to the toxicological profile of on an ORP water solution of the present invention. Microcyn 60 (or M60), an exemplary ORP water solution of the present invention, was used in these studies.

In terms of safety, M60 was not an irritant to the skin or conjuctiva of rabbits as tested in compliance with international standards (AAMI 1997; NV SOP 16G-44; PFEUM 2000). Furthermore, an acute inhalation toxicity study in rats demonstrated that administration of Microcyn 60 by this route is safe.

The potential irritant effects of Microcyn 60 were evaluated in a primary ocular irritation study in rabbits. A volume of 0.1 mL of Microcyn 60 was instilled in the right eye of three New Zealand white rabbits. The left eye of each animal was left untreated as a control. The eyes were observed and scored at 1, 24, 48 and 72 hours for corneal ulceration or opacity, inflammation of the iris, and redness or chemosis of the conjunctiva. All animals were also observed once daily for mortality and signs of ill health.

No signs of ocular irritation were observed in any of the treated or control eyes at any time during the study. All animals appeared clinically healthy for the duration of the study. These findings indicate that Microcyn 60 does not cause a positive irritation response.

An acute inhalation toxicity study was also performed in rats to determine the potential inhalation toxicity of Microcyn 60. Ten Sprauge-Dawley albino rats were exposed to an aerosol generated from undiluted Microcyn 60 for 4 hours. The concentration of the Microcyn 60 was determined to be 2.16 mg/L. All animals were observed frequently on the day of exposure and once daily for 14 days thereafter for mortality and clinical/behavioral signs of toxicity. All animals were euthanized on Day 14 and gross necropsies were performed.

All animals showed very slight to slight piloerection and very slight decreased activity at 4½ and 6 hours after exposure began but were asymptomatic by the following day and appeared clinically normal for the duration of the study. One male failed to gain weight between Day 0 and Day 7. There was no mortality and the gross necropsies revealed no observable abnormalities. The estimated acute inhalation LD50 from this study is greater than 2.16 mg/L.

Additional toxicological studies were performed in the rabbit. Aerosol superoxidized water (1 mL) will be delivered to the right nostril via a positive-pressure device to 20 New Zealand rabbits, three times a day for 15, 30, 45 and 60 days. The left-control nostril will be left without any treatment. Nasomucosa biopsies from the non treated- and M60 treated-nostrils will be obtained from five animals at each time point. These tissues will then be observed under optical and electron microscopy. A complete medical exam will be conducted in each animal every other day to document nasal obstruction, facial pain, pressure, mucopurulent rhinorrhea, and malaise. Side effects will be reported as infrequent, mild, and transient.

Changes to the nasal mucosa appeared after applying intranasal M60 for 60 days. There was mild destruction of the epithelia, discrete inflammatory infiltration of the subepithelia region and hyperplasia of glands and blood vessels in all samples on day 60. Under ultrastructral observation, we found that varying cyst-like changes within epithelial cells appeared; the mitochondria were condensed and deformed and part of the membrane was dissolved. Some epithelial cells were detached; epithelial cilia almost disappeared, and its membrane was dissolved and intercellular spaces were widened. Some cells had detached from the basement membrane. The tunica propria was mildly edematous.

This study demonstrates that M60 can mildly irritate the nasal mucosa after intranasal administration for sixty days. However, this damage was minimum and reversible, so the intranasal route of M60 administration could be considered safe. This is based on the fact that although the nasal mucosa can be seriously injured after applying vasoconstrictors for several years, it is still restored to normal after stopping these drugs. This is possible due to the process of regeneration in the nasal mucosa that depends on whether the basal cells and basement membrane remain intact after injury. Neighboring basal cells can move to the lesion along the basement membrane and cover the lesion. Therefore, even in the presence of mild detachment of the epithelial cells in some regions after M60 treatment, the basement membrane survived, and the surviving epithelial cells near the pathological region grew toward the region lacking the epithelia. Furthermore, topical steroids could have also been applied to promote recovery of the structure and function of the nasal mucosa.

In conclusion, M60 intranasal administration for five days was safe in this cohort. Pathological mucosa changes were mild and reversible. Therefore, the intranasal administration of M60 could be widely used.

EXAMPLE 12

This example illustrates the activity, stability, and lack of toxicity of an exemplary ORP water.

One such ORP water solution for use in this study is known as "Microcyn," recently introduced on the Mexican market as an antiseptic. Microcyn is a superoxidized solution of neutral pH with germicidal, sterilizing and wound antiseptic activity in accordance with certifications obtained from the Secretariat of Health of Mexico. Microcyn is prepared from pure water and salt (NaCl), has a small concentration of sodium (<55 ppm) and chlorine (<80 ppm), a pH in the range of 7.2 to 7.8, and oxidation-reduction potential in the range of 840 mV to 960 mV. Microcyn is produced in one concentration only, and need not be activated or diluted.

This solution is produced from water obtained by reverse osmosis, which is then subjected to an electrochemical gradient generated by high voltage and sodium chloride. In this way, the reactive species that form in the multiple chambers where the electrochemical gradient is generated are selected in a controlled way to create Microcyn. The result is a solution with a controlled content of free radicals that confer a high oxidation-reduction potential (+840 mV to +960 mV) and consequently high antimicrobial activity.

Hypochlorous acid and sodium hypochlorite are the most abundant elements contained in Microcyn, with others in minor concentration, such as hydrogen peroxide, ozone, chloride ions, hydride and sodium hydroxide, among others. Although applicants do not wish to be bound by a particular theory, it is believed that the disinfectant effect does not necessarily depend on the quantity of chlorine, but rather, in the content of free radicals, since the levels of sodium and chlorine in Microcyn are less than 50 and 60 parts per million, respectively. Also, and in contrast to other superoxidized solutions that have been reported in the literature, Microcyn has a neutral pH (6.4-7.8), is not corrosive and is stable in storage up to 2 years. All these characteristics have made it possible to produce a superoxidized solution that is effective as a high-level disinfectant and compatible for use both on inanimate surfaces and in tissues.

Accelerated stability tests have demonstrated that Microcyn can be stored in widely varying temperature conditions, from 4 to 65° C., without losing its disinfectant activity for a period of 2 years. This property of prolonged stability on the shelf is also the difference from superoxidized solutions reported previously that are only effective if they are used immediately after being produced. In other words, while Microcyn can be stored and distributed even in extreme conditions without losing its antimicrobial activity, other solutions would have to be produced by a specialized and costly machine in every hospital that tried to use that solution. Nevertheless, the manufacturer recommends that, once the container of Microcyn is opened, it be used within 30 days for the purpose of guaranteeing uniform activity and consistent results.

Because Microcyn is produced in only one concentration, the dose of Microcyn can be changed only by changes in the volume applied per unit area of the skin. In the toxicological studies, the doses of Microcyn applied topically to the intact skin varied between 0.05 and 0.07 mL/cm$^2$; in the study of acute dermatological toxicity and in the investigation of skin irritation, they were up to 8.0 mL/cm$^2$, and in those that investigated its application in deep wounds, Microcyn was applied in a dose of 0.09 mL/cm$^2$.

Toxicological studies were carried out that applied Microcyn topically to the intact skin, using a single application with exposure of 4 to 24 h. Multiple applications of Microcyn, one or two times a day, during a period of 7 days were assessed for deep wounds in rats.

Two studies were carried out on the intact skin of rabbits to evaluate the effect of Microcyn as to acute irritation and dermal toxicity. No clinical signs, dermal irritation, or abnormalities in the skin at autopsy were found in any of the animals exposed to Microcyn.

The characterization of local and systemic toxicity from topically applied Microcyn to a deep wound was evaluated in rats. No abnormalities, significant differences in the parameters of the blood chemistry or hematic cytology were observed, nor anomalies in the autopsies. The skin irritation gradings and the histopathology of the wounds and the tissues around the place of application did not reveal any difference between the wounds treated with Microcyn and those of the control group treated with saline solution.

The systemic toxicity of Microcyn was also evaluated by means of an intraperitoneal injection in mice. For this, five mice were injected with a single dose (50 mL/kg) of Microcyn by the intraperitoneal route. In the same way, five control mice were injected with a single dose (50 mL/kg) of saline solution (sodium chloride at 0.9%). In this investigation, neither mortality nor any evidence of systemic toxicity was observed in any of the animals that received the single intraperitoneal dose of Microcyn, for which the $LD_{50}$ is above 50 mL/kg.

Microcyn was administered by the oral route to rats to allow its absorption and to characterize any inherent toxic effect of the product. For this a single dose (4.98 mL/kg) was administered by esophageal tube to three albino rats of the Sprague-Dawley strain. There was no mortality, nor were there clinical signs or abnormalities in the autopsies of any of the animals exposed to the single oral dose of Microcyn.

The potential of topically applied Microcyn for ocular irritation was also evaluated in rabbits. Ocular irritation was not observed nor any other clinical sign in any animal exposed to Microcyn by topical administration through the ocular route.

Microcyn was applied by the inhalatory route to rats to determine potential acute toxicity by inhalation. All the animals showed a very slight or slight reduction in activity and piloerection after the exposure, but they were all asymptomatic on the following day. Mortality or abnormalities were not observed at autopsy of the animals exposed to Microcyn by inhalation.

Evaluation of the potential for sensitization of the skin with Microcyn was carried out in guinea pigs using a modified occlusion patch method (Buehler). Irritation was not observed in the animals of the control group after a simple treatment challenge, nor in the animals evaluated (treated by induction) after challenge with the treatment. Therefore, Microcyn does not provoke a sensitizing reaction.

Thus, when it has been applied to the intact skin, deep open dermal wounds, in the conjunctival sac, by oral and inhalation routes or by means of intraperitoneal injection, Microcyn has not shown adverse effects related to the product. There is also experience in having treated more than 500 patients with wounds of very diverse nature in the skin and mucosae, with excellent antiseptic and cosmetic results. Accordingly, topically applied Microcyn should be effective and well-tolerated in this clinical trial.

Microcyn is packaged in transparent 240 mL PET bottles. This product is stored at ambient temperature and remains stable for up to 2 years on the shelf if the bottle is not opened. On having been opened, it is recommended that all of the product be used in less than 90 days. From its profile of high biological safety, Microcyn can be emptied into the sink without risk of contamination or corrosion.

Multiple microbial trials have been run with Microcyn, both in the United States and in Mexico. Eradication of more than 90% of the bacteria occurs in the first few seconds of exposure. The antibacterial and antimycotic activity that Microcyn exhibits in accordance with this standard is summarized in Table 5.

TABLE 5

Microcyn Antibacterial and Antimycotic Activity

| Bacterium | Catalog | Time of action (reduction below 99.999%) |
|---|---|---|
| Ps. aeruginosa | ATCC 25619 | 1 min |
| St. aureus | ATCC 6538 | 1 min |
| E. coli | ATCC 11229 | 1 min |
| S. typhi | CDC 99 | 1 min |
| C. albicans | ATCC | 1 min |
| B. subtilis | 9372 | |
| Low spore ($10^4$) | | 10 min |
| High spore ($10^6$) | | 15 min |

The sporicidal activity trial was carried out in accordance with the PAHO [Pan-American Health Organization]/WHO protocol.

As for the virucidal activity, Microcyn was found to reduce the viral load of human immunodeficiency virus (strain SF33) by more than 3 logs in five minutes. This was verified by the absence of cytopathic effect and of the antigen Agp24 in the trials of virus treated with Microcyn. These trials were undertaken in accordance with the virucide protocols of the United States Environmental Protection Agency (DIS/TSS-7/Nov. 12, 1981).

The virucidal activity of Microcyn has recently been confirmed in studies carried out in the United States against HIV and polio virus, and its activity against *Listeria monocytogenes*, MRSA and *Mycobacterium tuberculosis* has also been documented. Thus, it has been demonstrated that Microcyn, when it is administered as recommended, can eradicate bacteria, fungi, viruses and spores from one to fifteen minutes of exposure.

EXAMPLE 13

This example demonstrates the use of an exemplary ORP water solution, Microcyn as an effective antimicrobial solution.

An In Vitro Time-Kill evaluation was performed using Microcyn oxidative reductive potential water. Microcyn was evaluated versus challenge suspensions of fifty different microorganism strains—twenty-five American Type Culture Collection (ATCC) strains and twenty-five Clinical Isolates of those same species—as described in the Tentative Final Monograph, Federal Register, 17 Jun. 1994, vol. 59:116, pg. 31444. The percent reductions and the Log 10 reductions from the initial population of each challenge strain were determined following exposures to Microcyn for thirty (30) seconds, one (1) minute, three (3) minutes, five (5) minutes, seven (7) minutes, nine (9) minutes, eleven (11) minutes, thirteen (13) minutes, fifteen (15) minutes, and twenty (20) minutes. All agar-plating was performed in duplicate and Microcyn was evaluated at a 99% (v/v) concentration. All testing was performed in accordance with Good Laboratory Practices, as specified in 21 C.F.R. Part 58.

The following table summarizes the results of the above-mentioned In Vitro Time-Kill evaluation at the thirty second exposure mark for all populations tested which were reduced by more than 5.0 $Log_{10}$:

TABLE 6

| | | In Vitro 30-second Kill | | | |
|---|---|---|---|---|---|
| No. | Microorganism Species | Initial Population (CFU/mL) | Post-Exposure Population (CFU/mL) | $Log_{10}$ Reduction | Percent Reduction |
| 1 | Acinetobacter baumannii (ATCC #19003) | $2.340 \times 10^9$ | $<1.00 \times 10^3$ | 6.3692 | 99.9999 |
| 2 | Acinetobacter baumannii Clinical Isolate BSLI #061901Ab3 | $1.8150 \times 10^9$ | $<1.00 \times 10^3$ | 6.2589 | 99.9999 |
| 3 | Bacteroides fragilis (ATCC #43858) | $4.40 \times 10^{10}$ | $<1.00 \times 10^3$ | 7.6435 | 99.9999 |
| 4 | Bacteroides fragilis Clinical Isolate BSLI #061901Bf6 | $2.70 \times 10^{10}$ | $<1.00 \times 10^3$ | 7.4314 | 99.9999 |
| 5 | Candida albicans (ATCC #10231) | $2.70 \times 10^{10}$ | $<1.00 \times 10^3$ | 6.3345 | 99.9999 |
| 6 | Candida albicans Clinical Isolate BSLI #042905Ca | $5.650 \times 10^9$ | $<1.00 \times 10^3$ | 6.7520 | 99.9999 |
| 7 | Enterobacter aerogenes (ATCC #29007) | $1.2250 \times 10^9$ | $<1.00 \times 10^3$ | 6.0881 | 99.9999 |
| 8 | Enterobacter aerogenes Clinical Isolate BSLI #042905Ea | $1.0150 \times 10^9$ | $<1.00 \times 10^3$ | 6.0065 | 99.9999 |
| 9 | Enterococcus faecalis (ATCC #29212) | $2.610 \times 10^9$ | $<1.00 \times 10^3$ | 6.4166 | 99.9999 |
| 10 | Enterococcus faecalis Clinical Isolate BSLI #061901Efs2 | $1.2850 \times 10^9$ | $<1.00 \times 10^3$ | 6.1089 | 99.9999 |
| 11 | Enterococcus faecium VRE, MDR (ATCC #51559) | $3.250 \times 10^9$ | $<1.00 \times 10^3$ | 6.5119 | 99.9999 |
| 12 | Enterococcus faecium Clinical Isolate BSLI #061901Efm1 | $1.130 \times 10^9$ | $<1.00 \times 10^3$ | 6.0531 | 99.9999 |
| 13 | Escherichia coli (ATCC #11229) | $5.00 \times 10^8$ | $<1.00 \times 10^3$ | 5.6990 | 99.9998 |
| 14 | Escherichia coli Clinical Isolate BSLI #042905Ec1 | $3.950 \times 10^8$ | $<1.00 \times 10^3$ | 5.5966 | 99.9997 |
| 15 | Escherichia coli (ATCC #25922) | $6.650 \times 10^8$ | $<1.00 \times 10^3$ | 5.8228 | 99.9998 |
| 16 | Escherichia coli Clinical Isolate BSLI #042905Ec2 | $7.40 \times 10^8$ | $<1.00 \times 10^3$ | 5.8692 | 99.9998 |
| 17 | Haemophilus influenzae (ATCC #8149) | $1.5050 \times 10^9$ | $<1.00 \times 10^4$ | 5.1775 | 99.9993 |
| 18 | Haemophilus influenzae Clinical Isolate BSLI #072605Hi | $1.90 \times 10^9$ | $<1.00 \times 10^4$ | 5.2788 | 99.9995 |
| 19 | Klebsiella oxytoca MDR (ATCC #15764) | $1.120 \times 10^9$ | $<1.00 \times 10^3$ | 6.0492 | 99.9999 |
| 20 | Klebsiella oxytoca Clinical Isolate BSLI #061901Ko1 | $1.810 \times 10^9$ | $<1.00 \times 10^3$ | 6.2577 | 99.9999 |
| 21 | Klebsiella pneumoniae subsp. ozaenae (ATCC #29019) | $1.390 \times 10^9$ | $<1.00 \times 10^3$ | 6.1430 | 99.9999 |
| 22 | Klebsiella pneumoniae Clinical Isolate BSLI #061901Kpn2 | $9.950 \times 10^8$ | $<1.00 \times 10^3$ | 5.9978 | 99.9999 |
| 23 | Micrococcus luteus (ATCC #7468) | $6.950 \times 10^8$ | $<1.00 \times 10^3$ | 5.8420 | 99.9999 |
| 24 | Micrococcus luteus Clinical Isolate BSLI #061901Ml2 | $1.5150 \times 10^9$ | $<1.00 \times 10^3$ | 6.1804 | 99.9999 |
| 25 | Proteus mirabilis (ATCC #7002) | $1.5950 \times 10^9$ | $<1.00 \times 10^3$ | 6.2028 | 99.9999 |
| 26 | Proteus mirabilis Clinical Isolate BSLI #061901Pm2 | $2.0950 \times 10^9$ | $<1.00 \times 10^3$ | 6.3212 | 99.9999 |
| 27 | Pseudomonas aeruginosa (ATCC #15442) | $6.450 \times 10^8$ | $<1.00 \times 10^3$ | 5.8096 | 99.9999 |
| 28 | Pseudomonas aeruginosa Clinical Isolate BSLI #072605Pa | $1.3850 \times 10^9$ | $<1.00 \times 10^3$ | 6.1414 | 99.9999 |

TABLE 6-continued

In Vitro 30-second Kill

| No. | Microorganism Species | Initial Population (CFU/mL) | Post-Exposure Population (CFU/mL) | $Log_{10}$ Reduction | Percent Reduction |
|---|---|---|---|---|---|
| 29 | *Pseudomonas aeruginosa* (ATCC #27853) | $5.550 \times 10^8$ | $<1.00 \times 10^3$ | 5.7443 | 99.9999 |
| 30 | *Pseudomonas aeruginosa* Clinical Isolate BSLI #061901Pa2 | $1.1650 \times 10^9$ | $<1.00 \times 10^3$ | 6.0663 | 99.9999 |
| 31 | *Serratia marcescens* (ATCC #14756) | $9.950 \times 10^8$ | $<1.00 \times 10^3$ | 5.9978 | 99.9999 |
| 32 | *Serratia marcescens* Clinical Isolate BSLI #042905Sm | $3.6650 \times 10^9$ | $<1.00 \times 10^3$ | 6.5641 | 99.9999 |
| 33 | *Staphylococcus aureus* (ATCC #6538) | $1.5050 \times 10^9$ | $<1.00 \times 10^3$ | 6.1775 | 99.9999 |
| 34 | *Staphylococcus aureus* Clinical Isolate BSLI #061901Sa1 | $1.250 \times 10^9$ | $<1.00 \times 10^3$ | 6.0969 | 99.9999 |
| 35 | *Staphylococcus aureus* (ATCC #29213) | $1.740 \times 10^9$ | $<1.00 \times 10^3$ | 6.2405 | 99.9999 |
| 36 | *Staphylococcus aureus* Clinical Isolate BSLI #061901Sa2 | $1.1050 \times 10^9$ | $<1.00 \times 10^3$ | 6.0434 | 99.9999 |
| 37 | *Staphylococcus epidermidis* (ATCC #12228) | $1.0550 \times 10^9$ | $<1.00 \times 10^3$ | 6.0233 | 99.9999 |
| 38 | *Staphylococcus epidermidis* Clinical Isolate BSLI #072605Se | $4.350 \times 10^8$ | $<1.00 \times 10^3$ | 5.6385 | 99.9998 |
| 39 | *Staphylococcus haemolyticus* (ATCC #29970) | $8.150 \times 10^8$ | $<1.00 \times 10^3$ | 5.9112 | 99.9999 |
| 40 | *Staphylococcus haemolyticus* Clinical Isolate BSLI #042905Sha | $8.350 \times 10^8$ | $<1.00 \times 10^3$ | 5.9217 | 99.9999 |
| 41 | *Staphylococcus hominis* (ATCC #27844) | $2.790 \times 10^8$ | $<1.00 \times 10^3$ | 5.4456 | 99.9996 |
| 42 | *Staphylococcus hominis* Clinical Isolate BSLI #042905Sho | $5.20 \times 10^8$ | $<1.00 \times 10^3$ | 5.7160 | 99.9998 |
| 43 | *Staphylococcus saprophyticus* (ATCC #35552) | $9.10 \times 10^8$ | $<1.00 \times 10^3$ | 5.9590 | 99.9999 |
| 44 | *Staphylococcus saprophyticus* Clinical Isolate BSLI #042905Ss | $1.4150 \times 10^9$ | $<1.00 \times 10^3$ | 6.1508 | 99.9999 |
| 45 | *Streptococcus pneumoniae* (ATCC #33400) | $2.1450 \times 10^9$ | $<1.00 \times 10^4$ | 5.3314 | 99.9995 |
| 46 | *Streptococcus pyogenes* (ATCC #19615) | $5.20 \times 10^9$ | $<1.00 \times 10^3$ | 6.7160 | 99.9999 |
| 47 | *Streptococcus pyogenes* Clinical Isolate BSLI #061901Spy7 | $2.5920 \times 10^9$ | $<1.00 \times 10^3$ | 6.4141 | 99.9999 |

While their microbial reductions were measured at less than 5.0 $Log_{10}$, Microcyn also demonstrated antimicrobial activity against the remaining three species not included in Table 6. More specifically, a thirty second exposure to Microcyn reduced the population of *Streptococcus pneumoniae* (Clinical Isolate; BSLI #072605Spn1) by more than 4.5 $Log_{10}$, which was the limit of detection versus this species. Further, when challenged with *Candida tropicalis* (ATCC #750), Microcyn demonstrated a microbial reduction in excess of 3.0 $Log_{10}$ following a thirty second exposure. Additionally, when challenged with *Candida tropicalis* (BSLI #042905Ct), Microcyn demonstrated a microbial reduction in excess of 3.0 $Log_{10}$ following a twenty minute exposure.

The exemplary results of this In Vitro Time-Kill evaluation demonstrate that Microcyn oxidative reductive potential water exhibits rapid (i.e., less than 30 seconds in most cases) antimicrobial activity versus a broad spectrum of challenging microorganisms. Microbial populations of forty-seven out of the fifty Gram-positive, Gram-negative, and yeast species evaluated were reduced by more than 5.0 $Log_{10}$ within thirty seconds of exposure to the product.

EXAMPLE 14

This example demonstrates a comparison of the antimicrobial activity of an exemplary ORP water solution, Microcyn, versus HIBICLENS® chlorhexidine gluconate solution 4.0% (w/v) and 0.9% sodium chloride irrigation (USP).

An In Vitro Time-Kill evaluation was performed as described in Example 13 using HIBICLENS® chlorhexidine gluconate solution 4.0% (w/v) and a sterile 0.9% sodium chloride irrigation solution (USP) as reference products. Each reference product was evaluated versus suspensions of the ten American Type Culture Collection (ATCC) strains specifically denoted in the Tentative Final Monograph. The data collected was then analyzed against the Microcyn microbial reduction activity recorded in Example 13.

Microcyn oxidative reductive potential water reduced microbial populations of five of the challenge strains to a level comparable to that observed for the HIBICLENS® chlorhexidine gluconate solution. Both Microcyn and HIBICLENS® provided a microbial reduction of more than 5.0 $Log_{10}$ following a thirty second exposure to the following species: *Escherichia coli* (ATCC #11229 and ATCC #25922), *Pseudomonas aeruginosa* (ATCC #15442 and ATCC #27853), and *Serratia marcescens* (ATCC #14756). Further, as shown above in Table 5, Microcyn demonstrated excellent antimicrobial activity against *Micrococcus luteus* (ATCC #7468) by providing a 5.8420 $Log_{10}$ reduction after a thirty second exposure. However, a direct *Micrococcus luteus* (ATCC #7468) activity comparison to HIBICLENS® was not possible because after a thirty second exposure, HIBICLENS® reduced the population by the detection limit of the test (in this specific case, by more than 4.8 $Log_{10}$). It is noted that the sterile 0.9% sodium chloride irrigation solution reduced microbial populations of each of the six challenge strains discussed above by less than 0.3 $Log_{10}$ following a full twenty minute exposure.

Microcyn oxidative reductive potential water provided greater antimicrobial activity than both HIBICLENS® and the sodium chloride irrigation for four of the challenge strains tested: *Enterococcus faecalis* (ATCC #29212), *Staphylococcus aureus* (ATCC #6538 and ATCC #29213), and *Staphylococcus epidermidis* (ATCC #12228). The following table summarizes the microbial reduction results of the In Vitro Time-Kill evaluation for these four species:

TABLE 7

Comparative Kill Results

| Microorganism Species | Exposure Time | $Log_{10}$ Reduction | | |
|---|---|---|---|---|
| | | Microcyn | HIBI-CLENS® | NaCl Irrigation |
| *Enterococcus faecalis* (ATCC #29212) | 30 seconds | 6.4166 | 1.6004 | 0.3180 |
| | 1 minute | 6.4166 | 2.4648 | 0.2478 |
| | 3 minutes | 6.4166 | 5.2405 | 0.2376 |
| | 5 minutes | 6.4166 | 5.4166 | 0.2305 |
| | 7 minutes | 6.4166 | 5.4166 | 0.2736 |
| | 9 minutes | 6.4166 | 5.4166 | 0.2895 |
| | 11 minutes | 6.4166 | 5.4166 | 0.2221 |
| | 13 minutes | 6.4166 | 5.4166 | 0.2783 |
| | 15 minutes | 6.4166 | 5.4166 | 0.2098 |
| | 20 minutes | 6.4166 | 5.4166 | 0.2847 |
| *Staphylococcus aureus* (ATCC #6538) | 30 seconds | 6.1775 | 1.1130 | 0.0000 |
| | 1 minute | 6.1775 | 1.7650 | 0.0191 |
| | 3 minutes | 6.1775 | 4.3024 | 0.0000 |
| | 5 minutes | 6.1775 | 5.1775 | 0.0000 |
| | 7 minutes | 6.1775 | 5.1775 | 0.0000 |
| | 9 minutes | 6.1775 | 5.1775 | 0.0000 |
| | 11 minutes | 6.1775 | 5.1775 | 0.0267 |
| | 13 minutes | 6.1775 | 5.1775 | 0.0000 |
| | 15 minutes | 6.1775 | 5.1775 | 0.0191 |
| | 20 minutes | 6.1775 | 5.1775 | 0.0000 |
| *Staphylococcus aureus* (ATCC #29213) | 30 seconds | 6.2405 | 0.9309 | 0.0000 |
| | 1 minute | 6.2405 | 1.6173 | 0.0000 |
| | 3 minutes | 6.2405 | 3.8091 | 0.0460 |
| | 5 minutes | 6.2405 | 5.2405 | 0.0139 |
| | 7 minutes | 6.2405 | 5.2405 | 0.0000 |
| | 9 minutes | 6.2405 | 5.2405 | 0.0113 |
| | 11 minutes | 6.2405 | 5.2405 | 0.0283 |
| | 13 minutes | 6.2405 | 5.2405 | 0.0000 |
| | 15 minutes | 6.2405 | 5.2405 | 0.0000 |
| | 20 minutes | 6.2405 | 5.2405 | 0.0615 |
| *Staphylococcus epidermidis* (ATCC #12228) | 30 seconds | 5.6385 | 5.0233 | 0.0456 |
| | 1 minute | 5.6385 | 5.0233 | 0.0410 |
| | 3 minutes | 5.6385 | 5.0233 | 0.0715 |
| | 5 minutes | 5.6385 | 5.0233 | 0.0888 |
| | 7 minutes | 5.6385 | 5.0233 | 0.0063 |
| | 9 minutes | 5.6385 | 5.0233 | 0.0643 |
| | 11 minutes | 5.6385 | 5.0233 | 0.0211 |
| | 13 minutes | 5.6385 | 5.0233 | 0.1121 |
| | 15 minutes | 5.6385 | 5.0233 | 0.0321 |
| | 20 minutes | 5.6385 | 5.0233 | 0.1042 |

The results of this comparative In Vitro Time-Kill evaluation demonstrate that Microcyn oxidative reductive potential water not only exhibits comparable antimicrobial activity to HIBICLENS® against *Escherichia coli* (ATCC #11229 and ATCC #25922), *Pseudomonas aeruginosa* (ATCC #15442 and ATCC #27853), *Serratia marcescens* (ATCC #14756), and *Micrococcus luteus* (ATCC #7468), but provides more effective treatment against *Enterococcus faecalis* (ATCC #29212), *Staphylococcus aureus* (ATCC #6538 and ATCC #29213), and *Staphylococcus epidermidis* (ATCC #12228). As shown in Table 7, Microcyn exemplifies a more rapid antimicrobial response (i.e., less than 30 seconds) in some species. Moreover, exposure to Microcyn results in a greater overall microbial reduction in all species listed in Table 7.

EXAMPLE 15

This example provides a formulation of the invention suitable for topical administration to a patient. The formulation contains the following:

| Component | Quantity |
|---|---|
| ORP water solution | 250 mL |
| Carbopol ® polymer powder (thickening agent) | 15 g |
| Triethanolamine (neutralizing agent) | 80 mL |

EXAMPLE 16

This example provides a formulation of the invention suitable for topical administration to a patient. The formulation contains the following:

| Component | Quantity |
|---|---|
| ORP water solution | 1000 mL |
| Carbopol ® polymer powder (thickening agent) | 15 g |
| Triethanolamine (neutralizing agent) | 80 mL |

EXAMPLE 17

This example provides a formulation of the invention suitable for topical administration to a patient. The formulation contains the following:

| Component | Quantity |
|---|---|
| ORP water solution | 250 mL |
| Carbopol ® polymer powder (thickening agent) | 7 g |
| Triethanolamine (neutralizing agent) | 12 mL |

EXAMPLE 18

This example describes the manufacture of a formulation of the invention comprising an ORP water solution and a thickening agent.

An ORP water solution is put into a suitable container, such as a glass beaker or jar. Carbopol® 974P polymer is passed through a coarse sieve (or strainer), which permits rapid sprinkling, whilst at the same time breaking up any large agglomerates. The polymer Carbopol® 974P is then added as the thickening agent. The Carbopol® polymer is added slowly to prevent the formation of clumps and, thus, avoid an excessively long mixing cycle.

The solution is mixed rapidly during the addition of the Carbopol® polymer so that the powder dissolves at room temperature. The neutralizing agent triethanolamine is then added to the solution and mixed by means of an electric mixer or other suitable device, until a homogeneous gel is obtained. The addition of the neutralizing agent to the Carbopol® polymer composition converts the formulation into a gel.

EXAMPLE 19

This example describes the treatment of periodontal disease when using ORP water.

A study of 14 patients with gingivitis and incipient periodontitis was conducted. The patients were treated with ultrasonic scaling using oxidative reductive potential water solution as the irrigant in the Cavitron. After the ultrasonic scaling procedures, the patients used oxidative reductive potential water as a mouth rinse. Patients rinsed with oxidative reductive potential water solution for 2 minutes, three times a day, preferably after meals. No antibiotics or other medications were administered.

The patients were evaluated weekly for 12 weeks after scaling. The period of resolution of gingivitis in the patients was 2 to 4 weeks. Bleeding upon brushing was resolved within 24 hours to 4 days. None of the patients exhibited adverse effects from the use of oxidative reductive potential water solution. Within two weeks of treatment, all of the patients exhibited evidence of bone regeneration.

EXAMPLE 20

This example demonstrates the effect of an exemplary ORP water solution versus hydrogen peroxide (HP) on the viability of human diploid fibroblasts (HDFs). To study this potential toxicity, HDFs were exposed in vitro to ORP water solution and hydrogen peroxide (HP). HP is known to be toxic to eukaryotic cells, increasing apoptosis and necrosis and reducing cellular viability. In this example, cell viability, apoptosis and necrosis were measured in HDFs exposed to pure ORP water solution and 880 mM HP (a concentration employed for antiseptic uses of HP) for 5 and 30 minutes.

Figure 4B:
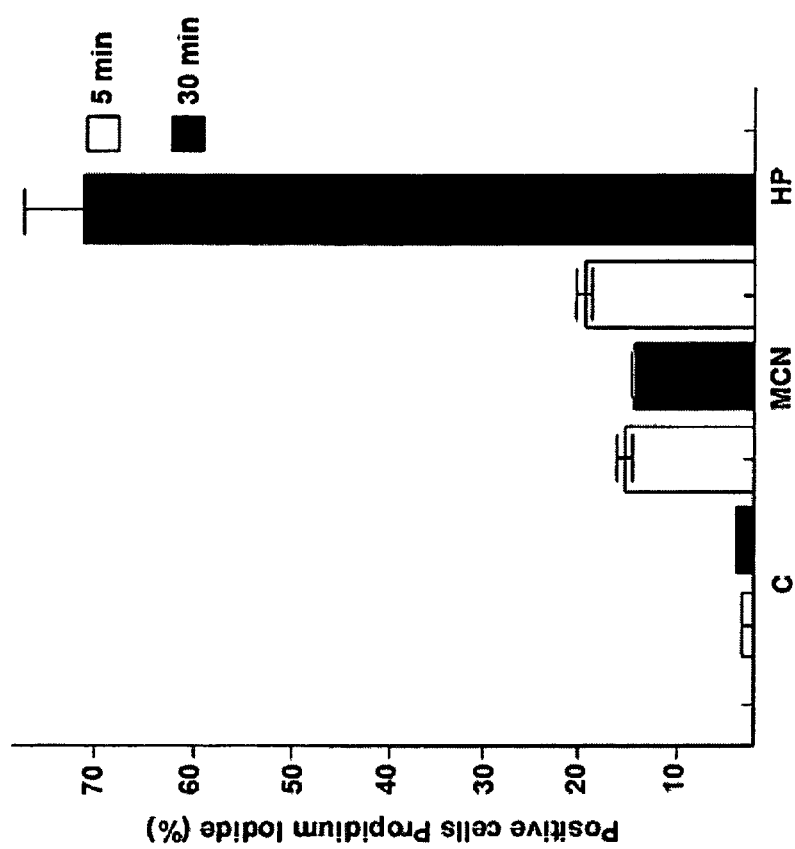
Figure 4C:
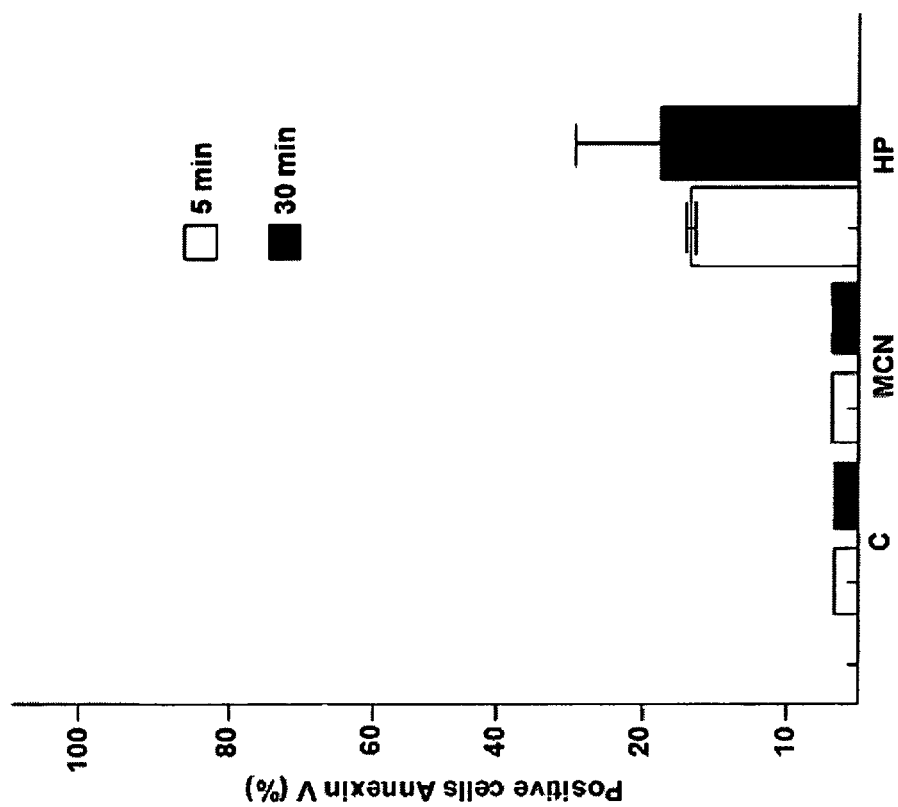

HDF cultures were obtained from three different foreskins, which were pooled and cryopreserved together for the purpose of this study. Only diploid cells were used for all experiments. On cell cycle analysis, DNA diploidy was defined as the presence of a single G0-G1 peak with a $CV \leq 7\%$ and a corresponding G2/M peak collected from at least 20,000 total events. FIGS. 4A-4C (FIG. 4A-4C) discloses the results with exposure times of 5 and 30 minutes are depicted in white and black bars, respectively. Simultaneous analyses of these parameters were performed in the same cell populations by flow cytometry using: FIG. 4A) 7-aminoactinomycin D (7AAD); FIG. 4B) Annexin V-FITC and FIG. 4C) Propidium iodide. FIGS. 8A-8C disclose percentage values expressed as mean±SD (n=3).

Cell viability was 75% and 55% after a 5 minute exposure to ORP water solution and HP, respectively (FIG. 4A). If the exposure was prolonged to 30 min, cell viability further decreased to 60% and 5%, respectively. Apparently, the ORP water solution induced cell death through necrosis because 15% of the cells incorporated propidium iodide in the flow cytometry analysis at both times (FIG. 4C). While not wanting to be bound by any particular theory, this result could be due to an osmotic effect induced by the hypotonicity of Microcyn (13mOsm) since the cells were kept in the ORP water solution only, without added growth factors or ions. Apoptosis does not seem to be the mechanism by which the ORP water solution induces cell death because only 3% of ORP water solution-treated cells exposed Annexin-V in the cellular surface (a marker of apoptosis) (FIG. 4B). This percentage was actually similar to the one measured in the control group. On the contrary, HP induced necrosis in 20% and 75% of treated cells and apoptosis in 15% and 20% after 5 and 30 min of exposure, respectively. Altogether these results show that the (undiluted) ORP water solution is far less toxic for HDFs than an antiseptic concentration of HP.

EXAMPLE 21

This example demonstrates the effect of an exemplary ORP water solution relative to hydrogen peroxide (HP) on oxidative DNA damage and formation of the DNA adduct 8-hydroxy-2'-deoxiguanosine (8-OHdG) in HDFs. It is known that the production of 8-OHdG adducts in a cell is a marker of oxidative damage at specific residues of DNA. In addition, high cellular levels of this adduct correlate with mutagenesis, carcinogenesis and cellular aging.

Figure 5:
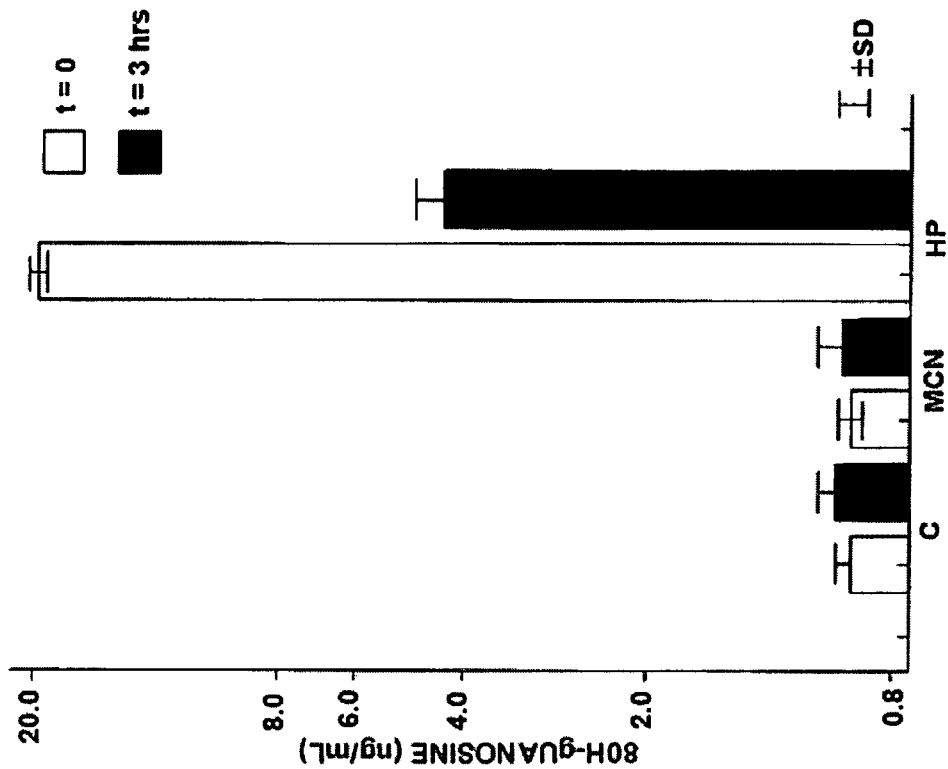
FIG. 5 is a graphical comparison of the levels of 8-hydroxy-2'-deoxiguanosine (8-OHdG) adducts in HDFs treated with an exemplary ORP water solution (MCN) versus 500 µM hydrogen peroxide (HP).

FIG. 5 (FIG. 5) shows the levels of 8-OHdG adducts present in DNA samples from HDFs after control treatments, ORP water solution treatments and HP-treatments for 30 minutes. DNA was extracted right after the exposure (T0, white bars) or three hours after the challenge period (T3, black bars). DNA was digested and the 8-OHdG adducts were measured by ELISA kit as per the manufacturer's instructions. Values are shown (ng/mL) as mean±SD (n=3). The exposure to ORP water solution for 30 minutes did not increase the formation of adducts in the treated cells in comparison to control cells after incubation for 30 minutes. In contrast, the treatment with highly diluted HP—down to sublethal and nontherapeutic HP concentrations (500 µM HP)—the treatment with 500 µM HP for 30 minutes increased the number of 8-OHdG adducts by about 25 fold relative to the control-treated or ORP water solution-treated cells.

The ORP water solution-treated cells were able to decrease the levels of 8-OHdG adducts if left in supplemented DMEM for 3 hours after exposure to the ORP water solution. Despite being allowed the same 3 hour recovery period, HP-treated cells still presented about 5 times more adducts than control-treated or ORP water solution treated cells. Altogether, these results demonstrate that acute exposure to the ORP water solution does not induce significant DNA oxidative damage. These results also indicate that the ORP water solution will not likely induce mutagenesis or carcinogenesis in vitro or in vivo.

EXAMPLE 22

Figure 6B:
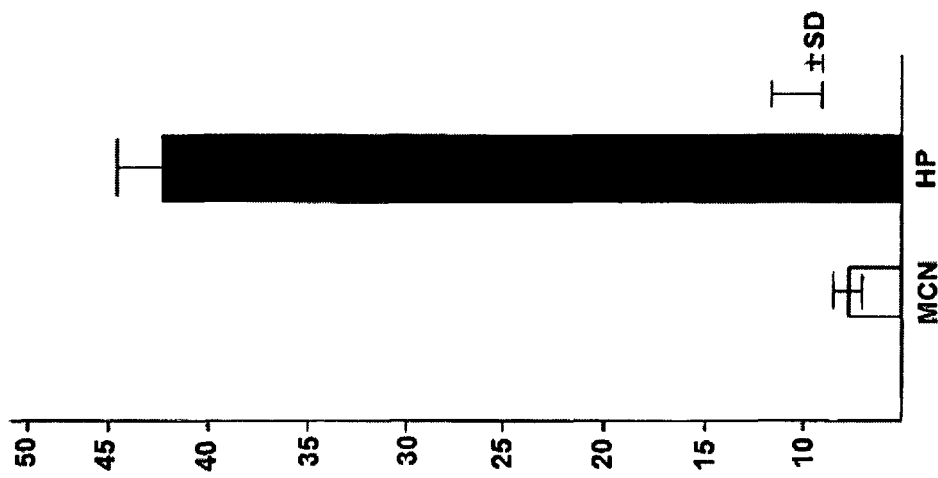

This example demonstrates the effects on HDFs of chronic exposure to low concentrations of an exemplary ORP water solution versus HP. It is known that chronic oxidative stress induces premature aging of cells. In order to mimic a prolonged oxidative stress, primary HDF cultures were chronically exposed to a low concentration of the ORP water solution (10%) or a non lethal-HP concentration (5 µM) during 20 population doublings. The expression and activity of the SA-β-galactosidase enzyme has previously been associated with the senescence process in vivo and in vitro. In this example the expression of the SA-β-galactosidase enzyme was analyzed after one month of continuous exposure of HDF to the ORP water solution or HP. The results are depicted in FIG. 6. The expression of the enzyme SA-β-galactosidase was analyzed by counting the number of blue cells in 20 microscopic fields. (For an example staining pattern, see Panel A.) Panel B shows that only HP treatment accelerated the aging of cells as indicated by the number of cells over-expressing SA-β-galactosidase (n=3). Chronic treatment with a low dose of HP increased the SA-β-Gal expression in 86% of cells while the treatment with the ORP water solution did not induce the overexpression of this protein. It can be concluded from this example that ORP water solution is not an inducer of premature cellular aging.

EXAMPLE 23

This example demonstrates the results of a toxicity study using an exemplary ORP water solution.

An acute systemic toxicity study was performed in mice to determine the potential systemic toxicity of Microcyn 60, an exemplary ORP water solution. A single dose (50 mL/kg) of Microcyn 60 was injected intraperitoneally in five mice. Five control mice were injected with a single dose (50 mL/kg) of saline (0.9% sodium chloride). All animals were observed for mortality and adverse reactions immediately following the injection, at 4 hours after injection, and then once daily for 7 days. All animals were also weighed prior to the injection and again on Day 7. There was no mortality during the study. All animals appeared clinically normal throughout the study. All animals gained weight. The estimated Microcyn 60 acute intraperitoneal LD50 from this study is greater than 50 mL/kg. This example demonstrates that Microcyn 60 lacks significant toxicity and should be safe for therapeutic use accordance with the invention.

EXAMPLE 24

This example illustrates a study conducted to determine the potential cytogenetic toxicity of an exemplary ORP water solution.

A micronucleus test was performed using an exemplary ORP water solution (Microcyn 10%) to evaluate the mutagenic potential of intraperitoneal injection of an ORP water solution into mice. The mammalian in vivo micronucleus test is used for the identification of substances which cause damage to chromosomes or the mitotic apparatus of murine polychromatic erythrocytes. This damage results in the formation of "micronuclei," intracellular structures containing lagging chromosome fragments or isolated whole chromosomes. The ORP water solution study included 3 groups of 10 mice each (5 males/5 females): a test group, dosed with the ORP water solution; a negative control group, dosed with a 0.9% NaCl solution; and a positive control group, dosed with a mutagenic cyclophosphamide solution. The test and the negative control groups received an intraperitoneal injection (12.5 ml/kg) of the ORP water solution or 0.9% NaCl solution, respectively, for two consecutive days (days 1 and 2). The positive control mice received a single intraperitoneal injection of cyclophosphamide (8 mg/mL, 12.5 ml/kg) on day 2. All mice were observed immediately after injection for any adverse reactions. All animals appeared clinically normal throughout the study and no sign of toxicity was noted in any group. On day 3, all mice were weighed and terminated.

The femurs were excised from the terminated mice, the bone marrow was extracted, and duplicate smear preparations were performed for each mouse. The bone marrow slides for each animal were read at 40× magnification. The ratio of polychromatic erythrocytes (PCE) to normochromatic erythrocytes (NCE), an index of bone marrow toxicity, was determined for each mouse by counting a total of at least 200 erythrocytes. Then a minimum of 2000 scoreable PCE per mouse were evaluated for the incidence of micronucleated polychromatic erythrocytes. Statistical analysis of the data were done using the Mann and Whitney test (at 5% risk threshold) from a statistical software package (Statview 5.0, SAS Institute Inc., USA).

The positive control mice had statistically significant lower PCE/NCE ratios when compared to their respective negative controls (males: 0.77 vs. 0.90 and females: 0.73 vs. 1.02), showing the toxicity of the cyclophosphamide on treated bone marrow. However, there was no statistically significant difference between the PCE/NCE ratios for the ORP water solution-treated mice and negative controls. Similarly, positive control mice had a statistically significant higher number of polychromatic erythrocytes bearing micronuclei as compared to both the ORP water solution-treated mice (males: 11.0 vs. 1.4/females: 12.6 vs. 0.8) and the negative controls (males: 11.0 vs. 0.6/females: 12.6 vs. 1.0). There was no statistically significant difference between the number of polychromatic erythrocytes bearing micronculei in ORP water solution-treated and negative control mice.

This example demonstrates that Microcyn 10% did not induce toxicity or mutagenic effects after intraperitoneal injections into mice.

EXAMPLE 25

This study demonstrates the lack of toxicity of an exemplary ORP water solution, Dermacyn.

This study was done in accordance with ISO 10993-5: 1999 standard to determine the potential of an exemplary ORP water solution, Dermacyn, to cause cytotoxicity. A filter disc with 0.1 mL of Dermacyn was placed onto an agarose surface, directly overlaying a monolayer of mouse fibroblast cells (L-929). The prepared samples were observed for cytotoxic damage after 24 hours of incubation at 37° C. in the presence of 5% $CO_2$. Observations were compared to positive and negative control samples. The Dermacyn containing samples did not reveal any evidence of cell lysis or toxicity, while positive and negative control performed as anticipated.

Based on this study Dermacyn was concluded not to generate cytotoxic effects on murine fibroblasts.

EXAMPLE 26

This study was conducted with 16 rats to evaluate the local tolerability of an exemplary ORP water solution, Dermacyn, and its effects on the histopathology of wound beds in a model of full-thickness dermal wound healing. Wounds were made on both sides of the subject rat. During the healing process skin sections were taken on either the left or the right sides (e.g., Dermacyn-treated and saline-treated, respectively).

Masson's trichrome-stained sections and Collagen Type II stained sections of the Dermacyn and saline-treated surgical wound sites were evaluated by a board-certified veterinary pathologist. The sections were assessed for the amount of Collogen Type 2 expression as a manifestation of connective tissue proliferation, fibroblast morphology and collagen formation, presence of neoepidermis in cross section, inflammation and extent of dermal ulceration.

The findings indicate that Dermacyn was well tolerated in rats. There were no treatment-related histopathologic lesions in the skin sections from either sides' wounds (Dermacyn-treated and saline-treated, respectively). There were no relevant histopathologic differences between the saline-treated and the Dermacyn-treated wound sites, indicating that the Dermacyn-treatement was well tolerated. There were no significant differences between Collagen Type 2 expression between the saline-treated and the Dermacyn-treated wound sites indicating that the Dermacyn does not have an adverse effect on fibroblasts or on collagen elaboration during wound healing.

EXAMPLE 27

This study can be done to demonstrate the safety and efficacy of an exemplary ORP water solution, Dermacyn, used in accordance with the invention as a replacement solution for the Versajet™ (Smith & Nephew) jet lavage system in the treatment of necrotic tissue (ulcers) distal to the malleoli, as compared to the standard regimen.

This will be a prospective randomized, double-blind, controlled study. Approximately 30 patients (about 20 in the Dermacyn group/about 10 in the Control group) will be enrolled in the study. The population for this study will be patients with lower extremity ulcers (e.g., diabetic foot ulcers, venous stasis ulcers). All of the study's inclusion and exclusion criteria must be satisfied by the Day 0 for the patient to be eligible for enrollment into the study. The inclusion criteria are: patient is 18 years old or older; patient's lower extremity ulcer has necrotic tissue present and is a candidate for mechanical debridement by the jet lavage system; patient's ulcer is located distal to the malleoli; patient's ulcer surface area is greater than or equal to 1.0 $cm^2$; patient's ulcer extends through the dermis and into subcutaneous tissue (granulation tissue may be present), with possible exposure of muscle, or tendon, but without bone, and/or joint capsule involvement; and patient's Ankle-Arm Index by Doppler is an ABI of greater than or equal to 0.8 or patient's toe pressure is greater than or equal to 40 mmHg.

The exclusion criteria are: patient has clinical evidence of gangrene on any part of the treatment limb; patient's ulcer is expected to be resected or amputated during the study period; patient's has the following signs of a systemic inflammatory response syndrome (SIRS); patient's ulcer has a total surface area that is less than 1 $cm^2$; patient has one or more medical condition(s) (including renal, hepatic, hematologic, neurologic, or immune disease) that in the opinion of the investigator would make the patient an inappropriate candidate for this study; patient has known active alcohol or drug abuse; patient is receiving oral or parenteral corticosteroids, immunosuppressive or cytotoxic agents, or is anticipated to require such agents during the course of the study; patient has known allergies to chlorine; patient's ulcer is accompanied by osteomyelitis; and patient has any condition(s) which seriously compromises the patient's ability to complete this study.

After the informed consent has been obtained, inclusion and exclusion criteria met, the patient will be randomized (2:1 randomization) into one of the following treatments: Treatment—Dermacyn with the jet lavage system, plus the use of a hydrogel wound dressing regimen; Control—Saline (standard treatment with the jet lavage systems), plus the use of a hydrogel wound dressing regimen.

Each patient randomized to Dermacyn will receive applications of the study product Dermacyn, with the Versajet jet lavage system during mechanical debridement of the patient's wound. A standard pressure setting on the Versajet will be used for diabetic foot ulcers, which will be distal to the malleoli. After debridement, Dermacyn will be applied onto the wound in sufficient quantities to rinse the wound bed free of debris. The wound will be covered with a hydrogel dressing. At every dressing change, the wound will be rinsed out with Dermacyn and covered with a new hydrogel dressing. The dressings will be changed every 3 days, unless otherwise specified by the investigator. The clinical response factors (CFRs) ((1) reduction of bacteria in the wound, (2) reduction in wound area, and (3) development of granulation tissue) will be determined during the weekly visits.

Each Control patient will receive applications of the Control product (saline solution) with the Versajet jet lavage system during mechanical debridement of the patient's wound. After debridement, saline will be applied onto the wound in sufficient quantities to rinse the wound bed free of debris. The wound will be covered with a hydrogel dressing. At every dressing change, the wound will be rinsed out with saline and covered with a new hydrogel dressing. The dressings will be changed every 3 days, unless otherwise specified by the investigator. The clinical response factors will be determined during the weekly visits.

Debridement of the wound may be performed at each weekly visit. Any necrotic tissue will be debrided with jet lavage prior to the wound assessments. Debris from the ulcer will be rinsed with either Dermacyn or saline (dependent upon the randomization). Between visits the patient will rinse the wound with Dermacyn or saline (dependent upon randomization) at every dressing change. Photographs of the wound will be taken at every visit after debridement.

The primary efficacy endpoints will be: (1) reduction of bacteria in the wound, (2) reduction in wound area, and (3) development of granulation tissue. Safety will be assessed in all patients who are randomized in the study. The treatment of emergent and serious adverse events will be recorded.

EXAMPLE 28

This study will demonstrate the safety and efficacy of an exemplary ORP water solution, Dermacyn, as a replacement solution for the Jet-Ox ND lavage system in the treatment of necrotic tissue in lower extremity ulcers as compared to the standard regimen used by the Jet-Ox ND system.

The Jet-Ox ND system removes necrotic tissue from chronic wounds via a controlled spray lavage of sterile saline, without damage to underlying healthy tissues. This study will replace saline with Dermacyn, which is expected to provide the same spray lavage effect and additionally reduce the bacterial load of the wound that may be inhibiting wound closure.

Twenty patients will be studied (randomized to yield 10 Dermacyn patients and 10 Control patients). The inclusion criteria will be: patient is older than 18 years; patient has a lower extremity below-the-knee ulcer with necrotic tissue present and is a candidate for mechanical debridement with the Jet-Ox ND lavage system; patients ulcer has been present >30 days prior to the screening visit; the ulcer surface area is >1 cm2 the ulcer extends through the dermis and into subcutaneous tissue (granulation tissue may be present) with possible exposure of muscle, tendon but, without exposed bone or capsule; patients ankle/arm index by doppler is >0.8 and/or patients toe pressure is >40 mmHg; and the patient has a palpable pulse at the dorsalis pedis and/or posterior tibial artery.

There will be the following exclusion criteria: renal, hepatic, hematologic, neurologic or immuno-compromised patients, including having Human Immunodeficiency virus (HIV) or Acquired Immunodeficiency Syndrome (AIDS); that in the opinion of the investigator would make the patient an inappropriate candidate for the study; wounds with the following clinical signs of infection; gangrene on any part of the treatment limb; ulcer exhibits exposed bone (positive probe to bone) or has other evidence of underlying osteomyelitis at the ulcer site; expectation that the infected ulcer will be amputated or resected during the study period; severe malnutrition as evidenced by an albumin of <2.0; known alcohol or drug abuse; patients receiving oral or parenteral corticosteroids, immunosuppressive or cytotoxic agents, coumadin, heparin, or is anticipated to require such agents during the course of the study; and patient has known allergy to chlorine.

Each individual will be randomized into one of two treatment arms; Dermacyn or saline. The target ulcer will receive mechanical debridement, followed by irrigation of the wound with either Dermacyn or saline and bandaging with a hydrogel dressing. A central wound biopsy for quantitive culture will be taken, along with laboratory studies (hematology, serum chemistry and pregnancy testing as appropriate), non-invasive peripheral vascular studies, medical history and physical examination, ulcer tracings, and ulcer photographs.

A Jet-Ox ND lavage system will be dispensed along with Dermacyn or saline, hydrogel and bandaging materials. Directions for home use will be provided. Visits will include screening, enrollment [day 0] with randomization, weekly visits with debridement, photographs and assessments. Efficacy will be determined by (1) reduction of bacteria in the wound, (2) reduction in wound area, and (3) development of granulation tissue during the course of the study. Safety will be assessed in all patients who are randomized in the study. Treatment emergent and serious adverse events will be recorded.

EXAMPLE 28

This example demonstrates the use of an exemplary ORP water solution as part of a root canal procedure.

Infection due to a canal not being cleaned or filled completely is a complication that can occur from 10 to 30% of the cases undergoing root canal treatment. This may be due to the complexity of the root canal system, for example some root canals may be very narrow or curved. Infection can also be due to a canal not being cleaned or filled at all, if the X-ray did not show all of a tooth's canals. Additionally, certain bacteria may not respond to root canal therapy. Since ORP water solution exerts a wide antimicrobial activity without sensitizing or irriting skin and mucosas, ORP water solution was assessed for it utility in the prevention of acute reactions after root canal therapy.

Figure 7A:
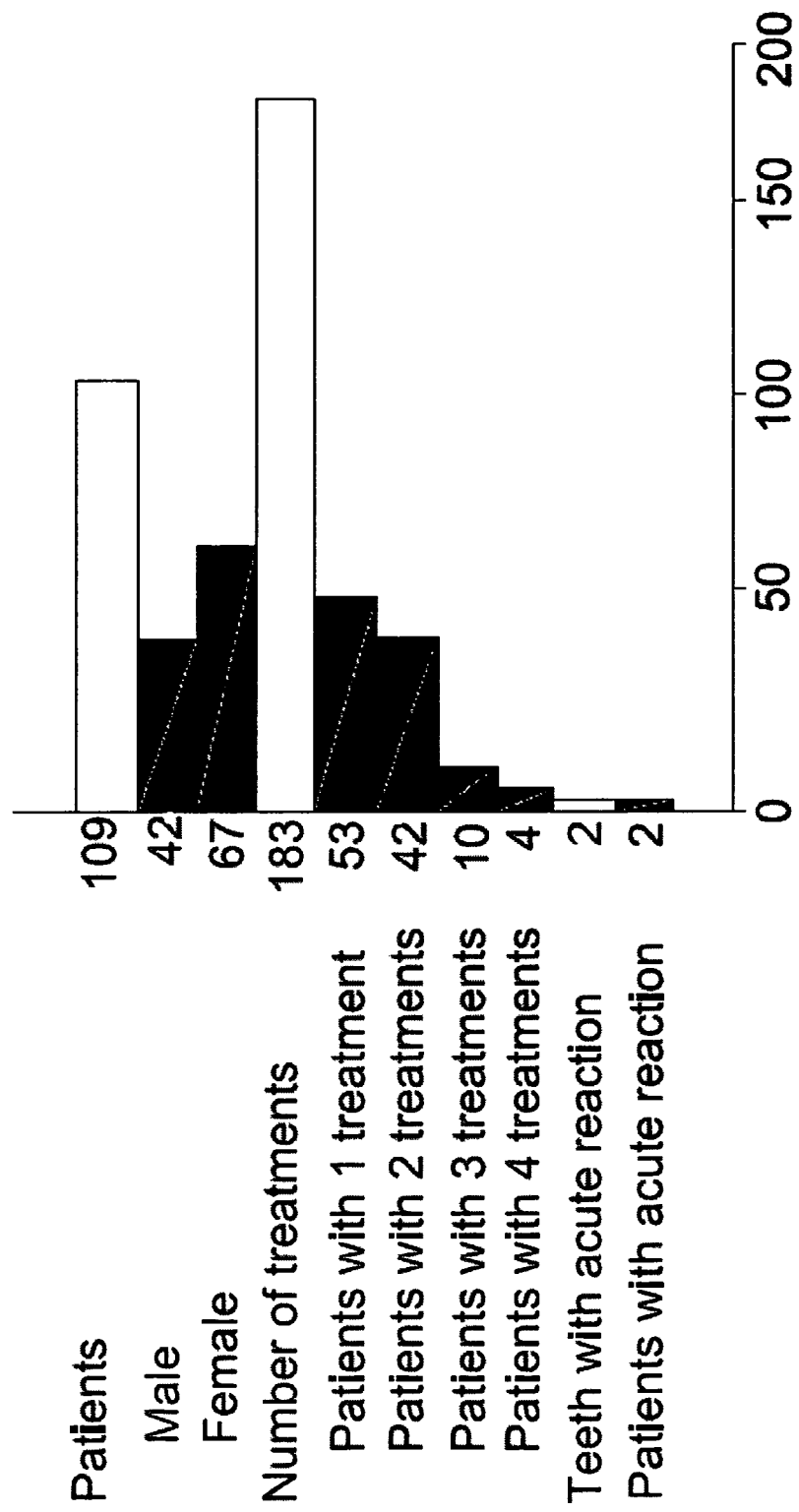
FIGS. 7A-B are graphical depictions of the patient groups and outcomes in the root canal study.
Figure 7B:
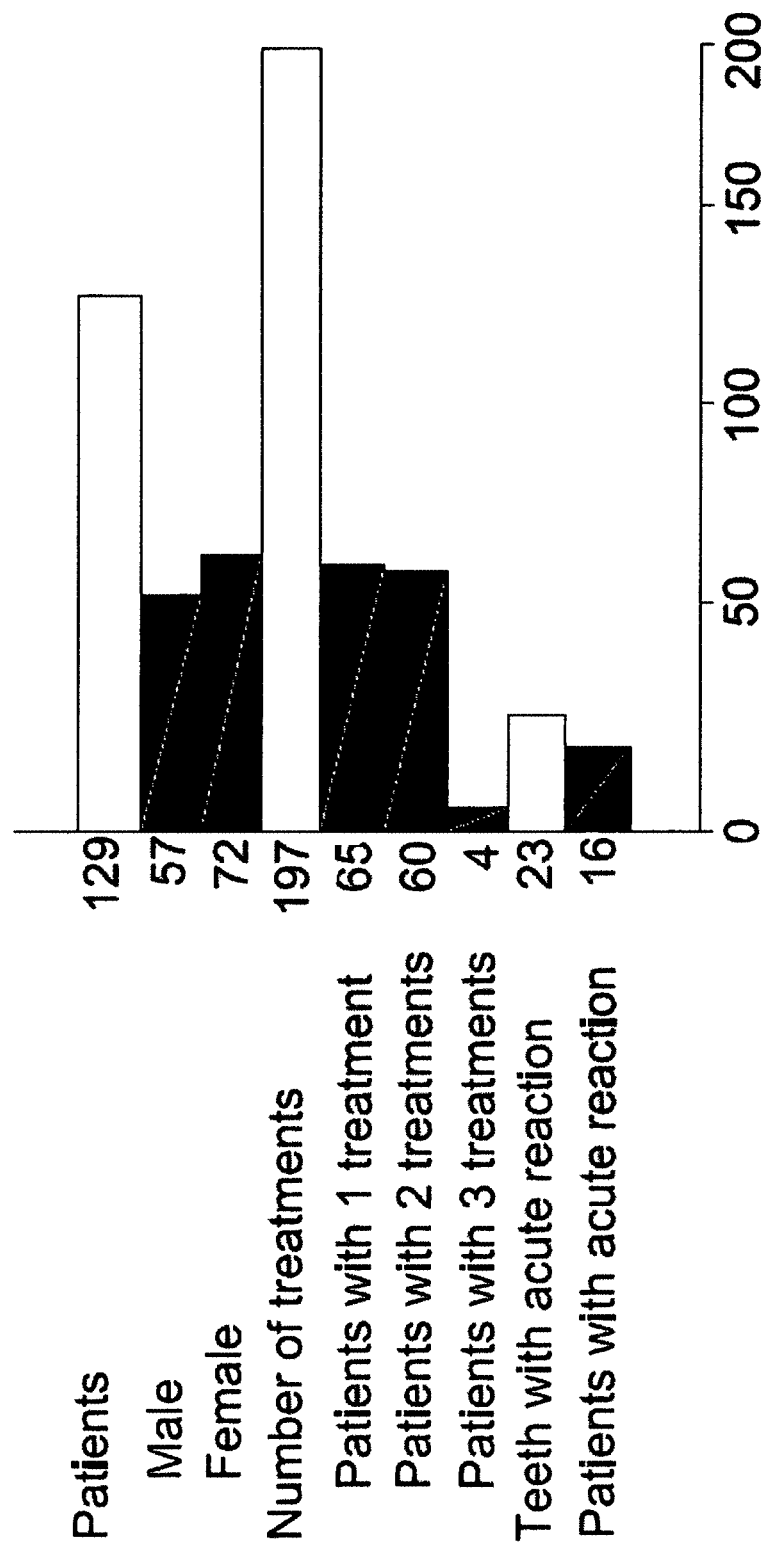

All consecutive patients seen at the Universidad Michoacana de San Nicolás de Hidalgo in Morelia, Mexico, from October 2003 to April 2005 and with a diagnosis of root canal infection were included in the ORP water solution group. Acute root canal was defined as an X-ray image showing a periapical lesion in addition to negative vitality and positive percussion clinical tests. Retrospective analysis of paired-cases presenting similar root canal infections between 2002 and 2003 at the same Institution was undertaken for the control group (the "SH" group) (see FIGS. 7A-B).

During the process the ducts were isolated to avoid contamination. The cavity was opened and the root drilled. ORP water solution flush started with the drilling process instead of using water or saline solution. Instrumentation was conducted according to the crown down technique using rotatory NiTi instruments. Instrumentation was done according to the extension of the duct as measured by the X ray. Duct irrigation was conducted with the ORP water solution after using each instrument. A final irrigation with ORP water solution of the root cavity was conducted for up to 15 minute (contact time); injection of ORP water solution with a hypodermic needle to infiltrate the soft tissue surrounding the root with ORP water solution was done alternatively to fully decontaminate the duct. The duct was dried out with dental paper and occlusion done by lateral condensation with calcium hydroxide and epoxy resin. Outpatient treatments consisted of oral rinses with ORP water solution for 30 days, 3 times daily for 2 minutes (exchange 15 mL every 30 seconds). After 30 days, oral rinse once daily indefinitely was recommended. None of the patients treated with ORP water solution therapy received antibiotics or analgesics.

A standard art-known treatment procedure with sodium hypochlorite (SH) was conducted for root canal treatment in control patients. Particular care was paid to avoid infiltration of the solution to the periapical region during the manipulation. All patients in the control group received ampicilin (500 mg tid) or cephalexin (500 mg bid) for 7 days as well as anti-inflammatory drugs (naproxen 500 mg bid) as necessary.

The study included 238 patients with root canal treatment with either, 2.5% SH (129 pts) (control or "SH" group) or ORP water solution (109 pts). The demographic characteristics were similar for both groups (FIGS. 7 A & B). The average age was 42.5 (range 17-68) and 40 years (range 13-67) for the control and ORP water solution groups, respectively. The male:female ratio was also similar for the control and ORP water solution groups (44:56 vs 39:61, respectively).

Only 2 patients had an acute local reaction after the root canal treatment with ORP water solution, whereas 16 patients did it with 2.5% SH. However, the results were more significant considering the total number of affected teeth in ORP water solution group (2) versus those in the SH group (23). Dental losses only occurred in the SH control group.

Pain resolved within 24 hours in most cases. Patients could also chew within 24 hrs, when it usually takes 72 hrs with the use of other antiseptics.

Ten patients out of 109 in the ORP water solution group experienced a slight burning sensation on the tongue when gargling with ORP water solution. In these cases, the burning sensation occurred only in the first two days of application and it was only necessary to instruct the patients to spit out the solution without further rinsing. The burning then dissipated without any other secondary effect. There were no contraindications noted for the use of ORP water solution.

Thus, this example demonstrates that ORP water solution therapy was superior in reducing the incidence of acute reactions after root canal therapy in comparison to 2.5% sodium hypochlorite solution. In addition, patients with failures in the ORP water solution therapy group could be successfully re-treated with the solution. Therefore, none of the subjects in the SOS group lost teeth. Furthermore, the aggressive irrigation and infiltration procedures conducted with SOS could not have been done with any other antiseptic currently in use due to possible necrosis of surrounding tissues.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating periodontal diseases in a patient comprising administering an oxidative reductive potential water solution to the patient in an amount sufficient to treat the periodontal diseases, wherein the solution has a pH of 7.4 to 7.6 and is stable for at least two months, and wherein the solution comprises anode water and cathode water, wherein the solution has a total amount of free chlorine species from 50 ppm to 80 ppm, wherein the free chlorine species comprises from 15 ppm to 35 ppm hypochlorous acid and from 25 ppm to 50 ppm sodium hypochlorite, wherein the solution causes no more than 3% of cells contacted to expose Annexin-V on their cellular surfaces when contacted with the ORP water solution for up to about thirty minutes.

2. The method of claim 1, wherein the solution is stable for at least one year.

3. The method of claim 1, wherein the cathode water is present in an amount of from about 10% by volume to about 50% by volume of the solution.

4. The method of claim 3, wherein the cathode water is present in an amount of from about 20% by volume to about 40% by volume of the solution.

5. The method of claim 3, wherein the anode water is present in an amount of from about 50% by volume to about 90% by volume of the solution.

6. The method of claim 1, wherein the solution is administered to the patient by rinsing the oral cavity with the solution.

7. The method of claim 6, wherein the solution is administered to the patient for at least 30 seconds.

8. The method of claim 7, wherein the solution is administered to the patient for at least 2 minutes.

9. The method of claim 6, wherein the solution is administered to the patient at least once a day.

10. The method of claim 9, wherein the solution is administered to the patient at least three times a day.

* * * * *